(12) United States Patent
Korenberg et al.

(10) Patent No.: US 7,070,954 B1
(45) Date of Patent: Jul. 4, 2006

(54) ISOLATED SH3 GENES ASSOCIATES WITH MYELOPROLIFERATIVE DISORDERS AND LEUKEMIA AND USES THEREOF

(75) Inventors: Julie R. Korenberg, 8125 Skyline Dr., Los Angeles, CA (US) 90048-1865; Xiao-Ning Chen, 723 Nicholas La., Arcadia, CA (US) 91006

(73) Assignees: Julie R. Korenberg, Los Angeles, CA (US); Xiao-Ning Chen, Los Angeles, CA (US)

( * ) Notice: Subject to any disclaimer, the term of this patent is extended or adjusted under 35 U.S.C. 154(b) by 0 days.

(21) Appl. No.: 09/720,934

(22) PCT Filed: Apr. 16, 1999

(86) PCT No.: PCT/US99/08371

§ 371 (c)(1),
(2), (4) Date: Jan. 2, 2001

(87) PCT Pub. No.: WO99/53062

PCT Pub. Date: Oct. 21, 1999

Related U.S. Application Data

(60) Provisional application No. 60/082,007, filed on Apr. 16, 1998.

(51) Int. Cl.
*C12N 15/00* (2006.01)

(52) U.S. Cl. .................. 435/69.1; 536/23.1; 435/320.1; 435/325; 435/252.3; 435/254.2

(58) Field of Classification Search ............... 536/23.1, 536/24.33, 24.5; 435/69.1, 320.1, 325, 252.3, 435/254.2; 530/350
See application file for complete search history.

(56) References Cited

FOREIGN PATENT DOCUMENTS

WO    WO-96/31625    * 10/1996

OTHER PUBLICATIONS

Scott et al (Nature Genetics, 1999, 21:440-443).*
Skolnick et al. (2000, Trends in Biotech. 18:34-39).*
Bork (2000, Genome Research 10:398-400).*
Doerks et al. (1998, Trends in Genetics 14:248-250).*
Smith et al. (1997, Nature Biotechnology 15:1222-1223).*
Brenner (1999, Trends in Genetics 15:132-133).*
Bork et al. (1996, Trends in Genetics 12:425-427).*
Bowie et al. (1990, Science 247:1306-1310).*
Song et al., (Oct. 1999, Nature Genetics, vol. 23, pp. 166-175).*
Guipponi et al., (1998, Genomics, vol. 53, pp. 369-376).*
OMIM (Online Mendelian Inheritance in Men) with update history of 2002 (with the accession No. #601399 downloaded on Jul. 28, 2004 from url>>ncbi.nlm.nih.gov.*
Friedmann (Scientific American, Jun. 1997, pp. 96-101).*
Verma and Somia (1997, Nature, vol. 389, pp. 239-242).*
Rubanyi (2001, Molecular Aspects of Medicine 22, pp. 113-142).*
Chen and Antonarakis (1997, Cytogenetics and Cell Genetics, vol. 78, pp. 213-215).*
Definitation of "fluor" in Merriam-Webster Online Dictionary downloaded from url>>m-w.com on Aug. 9, 2004.*
Definitation of "-phore" in Merriam-Webster Online Dictionary downloaded from url>>m-w.com on Aug. 9, 2004.*
Because Voet et al., (Biochemistry, 1994, p. 815 only).*
Voet et al., (Biochemistry, 1994, p. 815 only).*
Pucharcós, Carles et al., Alu-splice cloning of human *Intersectin* (ITSN), a putative multivalent binding protein expressed in proliferating and differentiating neurons and overexpressed in Down syndrome, European Journal of Human Genetics (1999) 7, 704-712.

* cited by examiner

*Primary Examiner*—Misook Yu

(57) ABSTRACT

The present invention relates generally to the field of human genetics. Specifically, the present invention relates to methods and materials used to isolate and detect a human gene (SH3D1A), some polymorphic alleles of which cause susceptibility to cancers hematopoietic disorders and in particular platelet disorders, Down Syndrome, megakaryocytic disorders and leukemia. More specifically, the invention relates to isolated nucleic acid of the human SH3D1A gene, products, and their use in diagnosis and treatments. The invention further relates to the screening of drugs for cancer therapy. Finally, the invention relates to the screening of the SH3D1A gene for mutations, which are useful for diagnosing the predisposition to hematopoietic disorders.

17 Claims, 30 Drawing Sheets

SH3D1A

```
   1  CAAAAGAATT CCGGGTACGG CGGCTCGCGA GGAAGAATCC CGAGCGGGCT
  51  CCGGGACGGA CAGAGAGGCG GGCGGGGATG GTGTGCGGGG CTGCGGCTCC
 101  TGCGTCCCTC CCAGCGGCGC GTGAGCGGCA CTGATTTGTC CCTGGGGCGG
 151  CAGCGCGGAC CCGCCCGGAG ATGAGGCGTC GATTAGCAAG GTAAAAGTAA
 201  CAGAACCATG GCTCAGTTTC CAACACCTTT TGGTGGCAGC CTGGATATCT
 251  GGGCCATAAC TGTAGAGGAA AGAGCGAAGC ATGATCAGCA GTTCCATAGT
 301  TTAAAGCCAA TATCTGGATT CATTACTGGT GATCAAGCTA GAAACTTTTT
 351  TTTTCAATCT GGGTTACCTC AACCTGTTTT AGCACAGATA TGGGCACTAG
 401  CTGACATGAA TAATGATGGA AGAATGGATC AAGTGGAGTT TTCCATAGCT
 451  ATGAAACTTA TCAAACTGAA GCTACAAGGA TATCAGCTAC CCTCTGCACT
 501  TCCCCCTGTC ATGAAACAGC AACCAGTTGC TATTTCTAGC GCACCAGCAT
 551  TTGGTATGGG AGGTATCGCC AGCATGCCAC CGCTTACAGC TGTTGCTCCA
 601  GTGCCAATGG GATCCATTCC AGTTGTTGGA ATGTCTCCAA CCCTAGTATC
 651  TTCTGTTCCC ACAGCAGCTG TGCCCCCCCT GGCTAACGGG GCTCCCCCTG
 701  TTATACAACC TCTGCCTGCA TTTGCTCATC CTGCAGCCAC ATTGCCAAAG
 751  AGTTCTTCCT TTAGTAGATC TGGTCCAGGG TCACAACTAA ACACTAAATT
 801  ACAAAAGGCA CAGTCATTTG ATGTGGCCAG TGTCCCACCA GTGGCAGAGT
 851  GGGCTGTTCC TCAGTCATCA AGACTGAAAT ACAGGCAATT ATTCAATAGT
 901  CATGACAAAA CTATGAGTGG ACACTTAACA GGTCCCCAAG CAAGAACTAT
 951  TCTTATGCAG TCAAGTTTAC CACAGGCTCA GCTGGCTTCA ATATGGAATC
1001  TTTCTGACAT TGATCAAGAT GGAAAACTTA CAGCAGAGGA ATTTATCCTG
```

Figure 4

1051 GCAATGCACC TCATTGATGT AGCTATGTCT GGCCAACCAC TGCCACCTGT
1101 CCTGCCTCCA GAATACATTC CACCTTCTTT TAGAAGAGTT CGATCTGGCA
1151 GTGGTATATC TGTCATAAGC TCAACATCTG TAGATCAGAG GCTACCAGAG
1201 GAACCAGTTT TAGAAGATGA ACAACAACAA TTAGAAAAGA AATTACCTGT
1251 AACGTTTGAA GATAAGAAGC GGGAGAACTT TGAACGTGGC AACCTGGAAC
1301 TGGAGAAACG AAGGCAAGCT CTCCTGGAAC AGCAGCGCAA GGAGCAGGAG
1351 CGCCTGGCCC AGCTGGAGCG GGCGGAGCAG GAGAGGAAGG AGCGTGAGCG
1401 CCAGGAGCAA GAGCGCAAAA GACAACTGGA ACTGGAGAAG CAACTGGAAA
1451 AGCAGCGGGA GCTAGAACGG CAGAGAGAGG AGGAGAGGAG GAAAGAAATT
1501 GAGAGGCGAG AGGCTGCAAA ACGGGAACTT GAAAGGCAAC GACAACTTGA
1551 GTGGGAACGG AATCGAAGGC AAGAACTACT AAATCAAAGA AACAAAGAAC
1601 AAGAGGACAT AGTTGTACTG AAAGCAAAGA AAAAGACTTT GGAATTTGAA
1651 TTAGAAGCTC TAAATGATAA AAAGCATCAA CTAGAAGGGA AACTTCAAGA
1701 TATCAGATGT CGATTGACCA CCCAAAGGCA AGAAATTGAG AGCACAAACA
1751 AATCTAGAGA GTTGAGAATT GCCGAAATCA CCCATCTACA GCAACAATTA
1801 CAGGAATCTC AGCAAATGCT TGGAAGACTT ATTCCAGAAA AACAGATACT
1851 CAATGACCAA TTAAAACAAG TTCAGCAGAA CAGTTTGCAC AGAGATTCAC
1901 TTGTTACACT TAAAAGAGCC TTAGAAGCAA AAGAACTAGC TCGGCAGCAC
1951 CTACGAGACC AACTGGATGA AGTGGAGAAA GAAACTAGAT CAAAACTACA
2001 GGAGATTGAT ATTTTCAATA ATCAGCTGAA GGAACTAAGA GAAATACACA
2051 ATAAGCAACA ACTCCAGAAG CAAAAGTCCA TGGAGGCTGA ACGACTGAAA
2101 CAGAAAGAAC AAGAACGAAA GATCATAGAA TTAGAAAAAC AAAAGAAGA
2151 AGCCCAAAGA CGAGCTCAGG AAAGGGACAA GCAGTGGCTG GAGCATGTGC
2201 AGCAGGAGGA CGAGCATCAG AGACCAAGAA AACTCCACGA AGAGGAAAAA
2251 CTGAAAAGGG AGGAGAGTGT CAAAAAGAAG GATGGCGAGG AAAAAGGCAA

Figure 4

```
2301  ACAGGAAGCA CAAGACAAGC TGGGTCGGCT TTTCCATCAA CACCAAGAAC
2351  CAGCTAAGCC AGCTGTCCAG GCACCCTGGT CCACTGCAGA AAAAGGTCCA
2401  CTTACCATTT CTGCACAGGA AAATGTAAAA GTGGTGTATT ACCGGGCACT
2451  GTACCCCTTT GAATCCAGAA GCCATGATGA AATCACTATC CAGCCAGGAG
2501  ACATAGTCAT GGTGGATGAA AGCCAAACTG GAGAACCCGG CTGGCTTGGA
2551  GGAGAATTAA AAGGAAAGAC AGGGTGGTTC CCTGCAAACT ATGCAGAGAA
2601  AATCCCAGAA AATGAGGTTC CCGCTCCAGT GAAACCAGTG ACTGATTCAA
2651  CATCTGCCCC TGCCCCCAAA CTGGCCTTGC GTGAGACCCC CGCCCCTTTG
2701  GCAGTAACCT CTTCAGAGCC CTCCACGACC CCTAATAACT GGGCCGACTT
2751  CAGCTCCACG TGGCCCACCA GCACGAATGA GAAACCAGAA ACGGATAACT
2801  GGGATGCATG GGCAGCCCAG CCCTCTCTCA CCGTTCCAAG TGCCGGCCAG
2851  TTAAGGCAGA GGTCCGCCTT TACTCCAGCC ACGGCCACTG GCTCCTCCCC
2901  GTCTCCTGTG CTAGGCCAGG GTGAAAAGGT GGAGGGGCTA CAAGCTCAAG
2951  CCCTATATCC TTGGAGAGCC AAAAAAGACA ACCACTTAAA TTTTAACAAA
3001  AATGATGTCA TCACCGTCCT GGAACAGCAA GACATGTGGT GGTTTGGAGA
3051  AGTTCAAGGT CAGAAGGGTT GGTTCCCCAA GTCTTACGTG AAACTCATTT
3101  CAGGGCCCAT AAGGAAGTCT ACAAGCATGG ATTCTGGTTC TTCAGAGAGT
3151  CCTGCTAGTC TAAAGCGAGT AGCCTCTCCA GCAGCCAAGC CGGTCGTTTC
3201  GGGAGAAGAA ATTGCCCAGG TTATTGCCTC ATACACCGCC ACCGGCCCCG
3251  AGCAGCTCAC TCTCGCCCCT GGTCAGCTGA TTTTGATCCG AAAAAAGAAC
3301  CCAGGTGGAT GGTGGGAAGG AGAGCTGCAA GCACGTGGGA AAAAGCCGCCA
3351  GATAGGCTGG TTCCCAGCTA ATTATGTAAA GCTTCTAAGC CCTGGGACGA
3401  GCAAAATCAC TCCAACAGAG CCACCTAAGT CAACAGCATT AGCGGCAGTG
3451  TGCCAGGTGA TTGGGATGTA CGACTACACC GCGCAGAATG ACGATGAGCT
```

Figure 4

```
3501  GGCCTTCAAC AAGGGCCAGA TCATCAACGT CCTCAACAAG GAGGACCCTG
3551  ACTGGTGGAA AGGAGAAGTC AATGGACAAG TGGGGCTCTT CCCATCCAAT
3601  TATGTGAAGC TGACCACAGA CATGGACCCA AGCCAGCAAT GAATCATATG
3651  TTGTCCATCC CCCCCTCAGG CTTGAAAGTC CTCAAAGAGA CCCACTATCC
3701  CATATCACTG CCCAGAGGGA TGATGGGAGA TGCAGCCTTG ATCATGTGAC
3751  TTCCAGCATG ATCACCTACT GCCTTCTGAG TAGAAGAACT CACTGCAGAG
3801  CAGTTTACCT CATTTTACCT TAGTTGCATG TGATCGCAAT GTTTGAGTTA
3851  TTACTTGCAG AGATAGGAGC AAAAATTACA AAAACACACA GGGTAGTGGG
3901  TCCTTTTGTG GCTTTCCTAG TTACTCAAAT TGACTTTCCC CCACCTTTGC
3951  ACAGGTGCTT TCAATAGTTT TAAAATTATT TTTAAATATA TATTTTAGCT
4001  TTTTAATAAA CAAAATAAAT AAATGACTTC TTTGCTATTT TGGTTTTGCA
4051  AAAAGACCCA CTATCAAGGA ATGCTGCATG TGCTATTAAA AATTGTTCCA
4101  AATGTCCATA AATCTGAGAC TTGATGTATT TTTTCATTTT GTCCAGTGTT
4151  ACCAACTAAA TTGCTGCAGT TTGGGCTTT TCCCCCTTAC CATAGAAGTG
4201  CAGAGGAGTT CAGTATCTCT GTTTTAAAGA CGTATAGAAT GAGCCCAATT
4251  AAAGCGAAGG TGATTGTGCT TGTTTGTGTG TATCAGCTGT ACCTTGTTGA
4301  GCATGTAATA CATCCTGTAC ATAAGAAATT AGTTCTTTCC ATGGCAAAGC
4351  TATTACCTTG TACGATGCTC TAATCATATT GCATTTAATT TTATTTTGCA
4401  aCAGTGACCT TGTAGCCACA TGAGAAAGCA CTCTGTGTTT TGTTCGGTC
4451  TCAGATTTAT CTGGTTGAGT TGGTGTTTTG TTTGGGGTTT TTAATTTTGC
4501  GTGTTTGCAT AGCATAAAAT CAGTAGACAA CACCACTGAG GTCGTTACGA
4551  TCAACGATAT CCACAGTCTC TTTTAGTCT CTGTTACATG AAGTTTTATT
4601  CCAGTTACTT TTCATGGAAT GACCTATTTT GAACAAGTAA TTTCTTGAC
4651  AAGAAAGAAT GTATAGAAGT CTCCCTGCAA TTAATTTCCA ATGTTTACAT
4701  TTTTTAACTA GGACTGTGGA ATTTCTACAG ATTAATATGA AATGGAGCTC
```

Figure 4

```
4751  ATGGTCCGTT TGTGTGTTAG ATATGCTGTA GCTGAAGCCC TGTTTGTCTT

4801  TTAAACACTA GTTGGAAGCT CTCAATAAAA ATGCCTGCTG CTCACAGCAC

4851  AGAAAATGGG GCAGGGGGAG CCTCAAGCAC AATCTAGCTG TCCTCCTAAA

4901  GACTCTGTAA TGCTCAATCC CCTTGCGTTC TCCCGCGCT GTCGGGAGGC

4951  TGTGCTGGTG GTCGTGTAGA GGTCCTTTTC CTTTCAAATG GTGCAGAGAG

5001  AGAGGACCTT TCCTCCTTGT TCAGTTGCAA TTCAGTATTT TCACGGATAT

5051  GAATGTAAAA TATATAAATA TATAAACCTG AGGATTTAAC AAATGTAAAA

5101  CAACCTTTTG AATTAGTTCC GAGTATAGAT AATTAAATTT TTAAAACAAA

5151  AGTAAAAAAA AAAAAAAAAA AAAAAAAAA AAAAGTCGAC GCGGCCGCG
```

Figure 4

SH3D1A Translated Protein Sequence:

```
  1  MAQFPTPFGG SLDIWAITVE ERAKHDQQFH SLKPISGFIT GDQARNFFFQ
 51  SGLPQPVLAQ IWALADMNND GRMDQVEFSI AMKLIKLKLQ GYQLPSALPP
101  VMKQQPVAIS SAPAFGMGGI ASMPPLTAVA PVPMGSIPVV GMSPILVSSV
151  PTAAVPPLAN GAPPVIQPLP AFAHPAATLP KSSSFSRSGP GSQLNIKLQK
201  AQSFDVASVP PVAEWAVPQS SRLKYRQLFN SHDKIMSGHL TGPQARTILM
251  QSSLPQAQLA SIWNLSDIDQ DGKLTAEEFI LAMHLIDVAM SGQPLPPVLP
301  PEYIPPSFRR VRSGSGISVI SSTSVDQRLP EEPVLEDEQQ QLEKKLPVTF
351  EDKKRENFER GNLELEKRRQ ALLEQQRKEQ ERLAQLERAE QERKERERQE
401  QERKRQLELE KQLEKQRELE RQREEERRKE IERREAAKRE LERQRQLEWE
451  RNRRQELLNQ RNKEQEDIVV LKAKKKTLEF ELEAINDKKH QLEGKLQDIR
501  CRLTTQRQEI ESTNKSRELR IAEITHLQQQ LQESQQMLGR LIPEKQILND
551  QLKQVQQNSL HRDSLVTLKR ALEAKELARQ HLRQQLDEVE KETRSKLQEI
601  DIFNNQLKEL REIHNKQQLQ KQKSMEAERL KQKEQERKII ELEKQKEEAQ
```

Figure 5

```
651  RRAQERDKQW LEHVQQEDEH QRPRKLHEEE KLKREESVKK KDGEEKGKQE
701  AQDKLGRLFH QHQEPAKPAV QAPWSTAEKG PLTISAQENV KVVYYRALYP
751  FESRSHDEIT IQPGDIVMVD ESQIGEPGWL GGELKGKTGW FPANYAEKIP
801  ENEVPAPVKP VIDSTSAPAP KLALRETPAP LAVTSSEPST TPNNWADFSS
851  TWPTSTNEKP EIDNWDAWAA QPSLIVPSAG QLRQRSAFTP ATATGSSPSP
901  VLGQGEKVEG LQACALYPWR AKKDNHLNFN KNDVITVLEQ QDMWWFGEVQ
951  GQKGWFPKSY VKLISGPIRK STSMDSGSSE SPASLKRVAS PAAKPVVSGE
1001 EIAQVIASYT ATGPEQLTLA PGQLILIRKK NPGGWWEGEL QARGKKRQIG
1051 WFPANYVKLL SPGTSKITPT EPPKSTALAA VCQVIGMYDY TAQNDDELAF
1101 NKGQIINVLN KEDPDWWKGE VNGQVGLFPS NYVKLTIDMD PSQ
```

Figure 5

```
   1 GCACGAGAGG GAGCGAAGGA GGTAGAGAAG AGTGGAGGCG CCAGGGGAGG
  51 GAGCGTAGCT TGGTTGCTCC GTAGTACGGC GGCTCGCGAG GAAGAATCCC
 101 GAGCGGGCTC CGGGACGGAC AGAGAGGCGG GCGGGGATGG TGTGCGGGGC
 151 TGCGGCTCCT GCGTCCCTCC CAGCGGCGCG TGAGCGGCAC TGATTTGTCC
 201 CTGGGGCGGC AGCGCGGACC CGCCCGGAGA TGAGGCGTCG ATTAGCAAGG
 251 TAAAAGTAAC AGAACCATGG CTCAGTTTCC AACACCTTTT GGTGGCAGCC
 301 TGGATATCTG GCCATAACT GTAGAGGAAA GAGCGAAGCA TGATCAGCAG
 351 TTCCATAGTT TAAAGCCAAT ATCTGGATTC ATTACTGGTG ATCAAGCTAG
 401 AAACTTTTTT TTTCAATCTG GGTTACCTCA ACCTGTTTTA GCACAGATAT
 451 GGGCACTAGC TGACATGAAT AATGATGGAA GAATGGATCA AGTGGAGTTT
 501 TCCATAGCTA TGAAACTTAT CAAACTGAAG CTACAAGGAT ATCAGCTACC
 551 CTCTGCACTT CCCCCTGTCA TGAAACAGCA ACCAGTTGCT ATTTCTAGCG
 601 CACCAGCATT TGGTATGGGA GGTATCGCCA GCATGCCACC GCTTACAGCT
 651 GTTGCTCCAG TGCCAATGGG ATCCATTCCA GTTGTTGGAA TGTCTCCAAC
 701 CCTAGTATCT TCTGTTCCCA CAGCAGCTGT GCCCCCCCTG CTAACGGGG
 751 CTCCCCCTGT TATACAACCT CTGCCTGCAT TTGCTCATCC TGCAGCCACA
 801 TTGCCAAAGA GTTCTTCCTT TAGTAGATCT GGTCCAGGGT CACAACTAAA
 851 CACTAAATTA CAAAAGGCAC AGTCATTTGA TGTGGCCAGT GTCCCACCAG
 901 TGGCAGAGTG GGCTGTTCCT CAGTCATCAA GACTGAAATA CAGGCAATTA
 951 TTCAATAGTC ATGACAAAAC TATGAGTGGA CACTTAACAG TCCCCAAGC
1001 AAGAACTATT CTTATGCAGT CAAGTTTACC ACAGGCTCAG CTGGCTTCAA
1051 TATGGAATCT TTCTGACATT GATCAAGATG GAAAACTTAC AGCAGAGGAA
1101 TTTATCCTGG CAATGCACCT CATTGATGTA GCTATGTCTG GCCAACCACT
1151 GCCACCTGTC CTGCCTCCAG AATACATTCC ACCTTCTTTT AGAAGAGTTC
1201 GATCTGGCAG TGGTATATCT GTCATAAGCT CAACATCTGT AGATCAGAGG
1251 CTACCAGAGG AACCAGTTTT AGAAGATGAA CAACAACAAT AGAAAAGAA
1301 ATTACCTGTA ACGTTTGAAG ATAAGAAGCG GGAGAACTTT GAACGTGGCA
1351 ACCTGGAACT GGAGAAACGA AGGCAAGCTC TCCTGGAACA GCAGCGCAAG
1401 GAGCAGGAGC GCCTGGCCCA GCTGGAGCGG GCGGAGCAGG AGAGGAAGGA
1451 GCGTGAGCGC CAGGAGCAAG AGCGCAAAAG ACAACTGGAA CTGGAGAAGC
1501 AACTGGAAAA GCAGCGGGAG CTAGAACGGC AGAGAGAGGA GGAGAGGAGG
1551 AAAGAAATTG AGAGGCGAGA GGCTGCAAAA CGGGAACTTG AAAGGCAACG
1601 ACAACTTGAG TGGGAACGGA ATCGAAGGCA AGAACTACTA AATCAAAGAA
1651 ACAAAGAACA AGAGGACATA GTTGTACTGA AAGCAAAGAA AAAGACTTTG
1701 GAATTTGAAT TAGAAGCTCT AAATGATAAA AAGCATCAAC TAGAAGGGAA
1751 ACTTCAAGAT ATCAGATGTC GATTGACCAC CCAAAGGCAA GAAATTGAGA
1801 GCACAAACAA ATCTAGAGAG TTGAGAATTG CCGAAATCAC CCATCTACAG
1851 CAACAATTAC AGGAATCTCA GCAAATGCTT GGAAGACTTA TTCCAGAAAA
1901 ACAGATACTC AATGACCAAT TAAAACAAGT TCAGCAGAAC AGTTTGCACA
1951 GAGATTCACT TGTTACACTT AAAAGAGCCT TAGAAGCAAA GAACTAGCT
2001 CGGCAGCACC TACGAGACCA ACTGGATGAA GTGGAGAAAG AAACTAGATC
2051 AAAACTACAG GAGATTGATA TTTTCAATAA TCAGCTGAAG GAACTAAGAG
2101 AAATACACAA TAAGCAACAA CTCCAGAAGC AAAAGTCCAT GGAGGCTGAA
```

Figure 8

2151 CGACTGAAAC AGAAAGAACA AGAACGAAAG ATCATAGAAT TAGAAAAACA
2201 AAAAGAAGAA GCCCAAAGAC GAGCTCAGGA AAGGGACAAG CAGTGGCTGG
2251 AGCATGTGCA GCAGGAGGAC GAGCATCAGA GACCAAGAAA ACTCCACGAA
2301 GAGGAAAAAC TGAAAAGGGA GGAGAGTGTC AAAAAGAAGG ATGGCGAGGA
2351 AAAAGGCAAA CAGGAAGCAC AAGACAAGCT GGGTCGGCTT TTCCATCAAC
2401 ACCAAGAACC AGCTAAGCCA GCTGTCCAGG CACCCTGGTC CACTGCAGAA
2451 AAAGGTCCAC TTACCATTTC TGCACAGGAA AATGTAAAAG TGGTGTATTA
2501 CCGGGCACTG TACCCCTTTG AATCCAGAAG CCATGATGAA ATCACTATCC
2551 AGCCAGGAGA CATAGTCATG GTTAAAGGGG AATGGGTGGA TGAAAGCCAA
2601 ACTGGAGAAC CCGGCTGGCT TGGAGGAGAA TTAAAAGGAA AGACAGGGTG
2651 GTTCCCTGCA AACTATGCAG AGAAAATCCC AGAAAATGAG GTTCCCGCTC
2701 CAGTGAAACC AGTGACTGAT TCAACATCTG CCCCTGCCCC CAAACTGGCC
2751 TTGCGTGAGA CCCCCGCCCC TTTGGCAGTA ACCTCTTCAG AGCCCTCCAC
2801 GACCCCTAAT AACTGGGCCG ACTTCAGCTC CACGTGGCCC ACCAGCACGA
2851 ATGAGAAACC AGAAACGGAT AACTGGGATG CATGGGCAGC CCAGCCCTCT
2901 CTCACCGTTC CAAGTGCCGG CCAGTTAAGG CAGAGGTCCG CCTTTACTCC
2951 AGCCACGGCC ACTGGCTCCT CCCCGTCTCC TGTGCTAGGC CAGGGTGAAA
3001 AGGTGGAGGG GCTACAAGCT CAAGCCCTAT ATCCTTGGAG AGCCAAAAAA
3051 GACAACCACT TAAATTTTAA CAAAAATGAT GTCATCACCG TCCTGGAACA
3101 GCAAGACATG TGGTGGTTTG GAGAAGTTCA AGGTCAGAAG GGTTGGTTCC
3151 CCAAGTCTTA CGTGAAACTC ATTTCAGGGC CATAAGGAA GTCTACAAGC
3201 ATGGATTCTG GTTCTTCAGA GAGTCCTGCT AGTCTAAAGC GAGTAGCCTC
3251 TCCAGCAGCC AAGCCGGTCG TTTCGGGAGA AGAATTTATT GCCATGTACA
3301 CTTACGAGAG TTCTGAGCAA GGAGATTTAA CCTTTCAGCA AGGGGATGTG
3351 ATTTTGGTTA CCAAGAAAGA TGGTGACTGG TGGACAGGAA CAGTGGGCGA
3401 CAAGGCCGGA GTCTTCCCTT CTAACTATGT GAGGCTTAAA GATTCAGAGG
3451 GCTCTGGAAC TGCTGGGAAA ACAGGGAGTT TAGGAAAAAA ACCTGAAATT
3501 GCCCAGGTTA TTGCCTCATA CACCGCCACC GGCCCCGAGC AGCTCACTCT
3551 CGCCCCTGGT CAGCTGATTT TGATCCGAAA AAAGAACCCA GGTGGATGGT
3601 GGGAAGGAGA GCTGCAAGCA CGTGGGAAAA AGCGCCAGAT AGGCTGGTTC
3651 CCAGCTAATT ATGTAAAGCT TCTAAGCCCT GGGACGAGCA AAATCACTCC
3701 AACAGAGCCA CCTAAGTCAA CAGCATTAGC GGCAGTGTGC AGGTGATTG
3751 GGATGTACGA CTACACCGCG CAGAATGACG ATGAGCTGGC CTTCAACAAG
3801 GGCCAGATCA TCAACGTCCT CAACAAGGAG GACCCTGACT GGTGGAAAGG
3851 AGAAGTCAAT GGACAAGTGG GGCTCTTCCC ATCCAATTAT GTGAAGCTGA
3901 CCACAGACAT GGACCCAAGC CAGCAATGAA TCATATGTTG TCCATCCCCC
3951 CCTCAGGCTT GAAAGTCCTC AAAGAGACCC ACTATCCCAT ATCACTGCCC
4001 AGAGGGATGA TGGGAGATGC AGCCTTGATC ATGTGACTTC CAGCATGATC
4051 ACCTACTGCC TTCTGAGTAG AAGAACTCAC TGCAGAGCAG TTTACCTCAT
4101 TTTACCTTAG TTGCATGTGA TCGCAATGTT TGAGTTATTA CTTGCAGAGA
4151 TAGGAGCAAA AATTACAAAA ACACACAGGG TAGTGGGTCC TTTTGTGGCT
4201 TTCCTAGTTA CTCAAATTGA CTTTCCCCCA CCTTTGCACA GGTGCTTTCA
4251 ATAGTTTTAA AATTATTTTT AAATATATAT TTTAGCTTTT TAATAAACAA
4301 AATAAATAAA TGACTTCTTT GCTATTTTGG TTTTGCAAAA AGACCCACTA
4351 TCAAGGAATG CTGCATGTGC TATTAAAAAT TGTTCCAAAT GTCCATAAAT

Figure 8

```
4401 CTGAGACTTG ATGTATTTTT TCATTTTGTC CAGTGTTACC AACTAAATTG
4451 TGCAGTTTGG GGCTTTTCCC CCTTACCATA GAAGTGCAGA GGAGTTCAGT
4501 ATCTCTGTTT TAAAGACGTA TAGAATGAGC CCAATTAAAG CGAAGGTGTT
4551 TGTGCTTGTT TGTGTGTATC AGCTGTACCT TGTTGAGCAT GTAATACATC
4601 CTGTACATAA GAAATTAGTT CTTTCCATGG CAAAGCTATT ACCTTGTACG
4651 ATGCTCTAAT CATATTGCAT TTAATTTTAT TTTGCACAGT GACCTTGTAG
4701 CCACATGAGA AGCACTCTG TGTTTTTGTT CGGTCTCAGA TTTATCTGGT
4751 TGAGTTGGTG TTTTGTTTGG GGTTTTTAAT TTTGCGTGTT TGCATAGCAT
4801 AAAATCAGTA GACAACACCA CTGAGGTCGT TACGATCAAC GATATCCACA
4851 GTCTCTTTTT AGTCTCTGTT ACATGAAGTT TTATTCCAGT TACTTTTCAT
4901 GGAATGACCT ATTTTGAACA AGTAATTTTC TTGACAAGAA AGAATGTATA
4951 GAAGTCTCCC TGCAATTAAT TTCCAATGTT TACATTTTTT AACTAGACTG
5001 TGGAATTTCT ACAGATTAAT ATGAAATGGA GCTCATGGTC CGTTTGTGTG
5051 TTAGATATGC TGTAGCTGAA GCCCTGTTTG TCTTTTAAAC ACTAGTTGGA
5101 AGCTCTCAAT AAAAATGCCT GCTGCTCACA GCACAGAAAA TGGGGCAGGG
5151 GGAGCCTCAA GCACAATCTA GCTGTCCTCC TAAAGACTCT GTAATGCTCA
5201 CTCCCCTCGC GTTCTCCCGG CGCTGTCGGG AGGCTGTGCT GGTGGTCGTG
5251 TAGAGGTCCT TCTCCTTTCA CATGGTGCAG AGAGCGAGGA CCTCTCCTCC
5301 TCGTTCAGTT GCACTTCAGT ATTTTCACGG ATATGAATGT AAAATATATA
5351 AATATATAAA CCTGCGGCTT TAACAACTGT AATACAACCT TTTGAATTAG
5401 TTCCGTGTAT AGATAATTAA ATTCTTCATA CAAAAGTTAA AAAAAAAAA
5451 AAAAAAAA
```

Figure 8

21 translated protein sequence:

```
   1 MAQFPTPFGG SLDIWAITVE ERAKHDQQFH SLKPISGFIT GDQARNFFFQ
  51 SGLPQPVLAQ IWALADMNND GRMDQVEFSI AMKLIKLKLQ GYQLPSALPP
 101 VMKQQPVAIS SAPAFGMGGI ASMPPLTAVA PVPMGSIPVV GMSPTLVSSV
 151 PTAAVPPLAN GAPPVIQPLP AFAHPAATLP KSSSFSRSGP GSQLNTKLQK
 201 AQSFDVASVP PVAEWAVPQS SRLKYRQLFN SHDKTMSGHL TGPQARTILM
 251 QSSLPQAQLA SIWNLSDIDQ DGKLTAEEFI LAMHLIDVAM SGQPLPPVLP
 301 PEYIPPSFRR VRSGSGISVI SSTSVDQRLP EEPVLEDEQQ QLEKKLPVTF
 351 EDKKRENFER GNLELEKRRQ ALLEQQRKEQ ERLAQLERAE QERKERERQE
 401 QERKRQLELE KQLEKQRELE RQREEERRKE IERREAAKRE LERQRQLEWE
 451 RNRRQELLNQ RNKEQEDIVV LKAKKKTLEF ELEALNDKKH QLEGKLQDIR
 501 CRLTTQRQEI ESTNKSRELR IAEITHLQQQ LQESQQMLGR LIPEKQILND
 551 QLKQVQQNSL HRDSLVTLKR ALEAKELARQ HLRDQLDEVE KETRSKLQEI
 601 DIFNNQLKEL REIHNKQQLQ KQKSMEAERL KQKEQERKII ELEKQKEEAQ
 651 RRAQERDKQW LEHVQQEDEH QRPRKLHEEE KLKREESVKK KDGEEKGKQE
 701 AQDKLGRLFH QHQEPAKPAV QAPWSTAEKG PLTISAQENV KVVYYRALYP
 751 FESRSHDEIT IQPGDIVMVK GEWVDESQTG EPGWLGGELK GKTGWFPANY
 801 AEKIPENEVP APVKPVTDST SAPAPKLALR ETPAPLAVTS SEPSTTPNNW
 851 ADFSSTWPTS TNEKPETDNW DAWAAQPSLT VPSAGQLRQR SAFTPATATG
 901 SSPSPVLGQG EKVEGLQAQA LYPWRAKKDN HLNFNKNDVI TVLEQQDMWW
 951 FGEVQGQKGW FPKSYVKLIS GPIRKSTSMD SGSSESPASL KRVASPAAKP
1001 VVSGEEFIAM YTYESSEQGD LTFQQGDVIL VTKKDGDWWT GTVGDKAGVF
1051 PSNYVRLKDS EGSGTAGKTG SLGKKPEIAQ VIASYTATGP EQLTLAPGQL
1101 ILIRKKNPGG WWEGELQARG KKRQIGWFPA NYVKLLSPGT SKITPTEPPK
1151 STALAAVCQV IGMYDYTAQN DDELAFNKGQ IINVLNKEDP DWWKGEVNGQ
1201 VGLFPSNYVK LTTDMDPSQQ *
```

Figure 9

Whole protein sequence

```
   1 TRGSEGGREE WRRQGRERSL VAP*YGGSRG RIPSGLRDGQ RGGRGWCAGL
  51 RLLRPSQRRV SGTDLSLGRQ RGPARR*GVD *QGKSNRTMA QFPTPFGGSL
 101 DIWAITVEER AKHDQQFHSL KPISGFITGD QARNFFFQSG LPQPVLAQIW
 151 ALADMNNDGR MDQVEFSIAM KLIKLKLQGY QLPSALPPVM KQQPVAISSA
 201 PAFGMGGIAS MPPLTAVAPV PMGSIPVVGM SPTLVSSVPT AAVPPLANGA
 251 PPVIQPLPAF AHPAATLPKS SSFSRSGPGS QLNTKLQKAQ SFDVASVPPV
 301 AEWAVPQSSR LKYRQLFNSH DKTMSGHLTG PQARTILMQS SLPQAQLASI
 351 WNLSDIDQDG KLTAEEFILA MHLIDVAMSG QPLPPVLPPE YIPPSFRRVR
 401 SGSGISVISS TSVDQRLPEE PVLEDEQQQL EKKLPVTFED KKRENFERGN
 451 LELEKRRQAL LEQQRKEQER LAQLERAEQE RKERERQEQE RKRQLELEKQ
 501 LEKQRELERQ REEERRKEIE RREAAKRELE RQRQLEWERN RRQELLNQRN
 551 KEQEDIVVLK AKKKTLEFEL EALNDKKHQL EGKLQDIRCR LTTQRQEIES
 601 TNKSRELRIA EITHLQQQLQ ESQQMLGRLI PEKQILNDQL KQVQQNSLHR
 651 DSLVTLKRAL EAKELARQHL RDQLDEVEKE TRSKLQEIDI FNNQLKELRE
 701 IHNKQQLQKQ KSMEAERLKQ KEQERKIIEL EKQKEEAQRR AQERDKQWLE
 751 HVQQEDEHQR PRKLHEEEKL KREESVKKKD GEEKGKQEAQ DKLGRLFHQH
 801 QEPAKPAVQA PWSTAEKGPL TISAQENVKV VYYRALYPFE SRSHDEITIQ
 851 PGDIVMVKGE WVDESQTGEP GWLGGELKGK TGWFPANYAE KIPENEVPAP
 901 VKPVTDSTSA PAPKLALRET PAPLAVTSSE PSTTPNNWAD FSSTWPTSTN
 951 EKPETDNWDA WAAQPSLTVP SAGQLRQRSA FTPATATGSS PSPVLGQGEK
1001 VEGLQAQALY PWRAKKDNHL NFNKNDVITV LEQQDMWWFG EVQGQKGWFP
1051 KSYVKLISGP IRKSTSMDSG SSESPASLKR VASPAAKPVV SGEEFIAMYT
1101 YESSEQGDLT FQQGDVILVT KKDGDWWTGT VGDKAGVFPS NYVRLKDSEG
1151 SGTAGKTGSL GKKPEIAQVI ASYTATGPEQ LTLAPGQLIL IRKKNPGGWW
1201 EGELQARGKK RQIGWFPANY VKLLSPGTSK ITPTEPPKST ALAAVCQVIG
1251 MYDYTAQNDD ELAFNKGQII NVLNKEDPDW WKGEVNGQVG LFPSNYVKLT
1301 TDMDPSQQ*I ICCPSPPQA* KSSKRPTIPY HCPEG*WEMQ P*SCDFQHDH
1351 LLPSE*KNSL QSSLPHFTLV ACDRNV*VIT CRDRSKNYKN TQGSGSFCGF
1401 PSYSN*LSPT FAQVLSIVLK LFLNIYFSFL INKINK*LLC YFGFAKRPTI
1451 KECCMCY*KL FQMSINLRLD VFFHFVQCYQ LNCAVWGFSP LP*KCRGVQY
1501 LCFKDV*NEP N*SEGVCACL CVSAVPC*AC NTSCT*EISS FHGKAITLYD
1551 ALIILHLILF CTVTL*PHEK ALCVFVRSQI YLVELVFCLG FLILRVCIA*
1601 NQ*TTPLRSL RSTISTVSF* SLLHEVLFQL LFME*PILNK *FS*QERMYR
1651 SLPAINFQCL HFLTRLWNFY RLI*NGAHGP FVC*ICCS*S PVCLLNTSWK
1701 LSIKMPAAHS TENGAGGASS TI*LSS*RLC NAHSPRVLPA LSGGCAGGRV
1751 EVLLLSHGAE SEDLSSSFSC TSVFSRI*M* NI*IYKPAAL TTVIQPFELV
1801 PCIDN*ILHT KVKKKKKK
```

Figure 9

```
   1 AGAGTGGAGG CGCCAGGGGA GGGAGCGTAG CTTGGTTGCT CCGTAGTACG
  51 GCGGCTCGCG AGGAAGAATC CCGAGCGGGC TCCGGGACGG ACAGAGAGGC
 101 GGGCGGGGAT GGTGTGCGGG GCTGCGGCTC CTGCGTCCCT CCCAGCGGCG
 151 CGTGAGCGGC ACTGATTTGT CCCTGGGGCG GCAGCGCGGA CCCGCCCGGA
 201 GATGAGGCGT CGATTAGCAA GGTAAAAGTA ACAGAACCAT GGCTCAGTTT
 251 CCAACACCTT TTGGTGGCAG CCTGGATATC TGGGCCATAA CTGTAGAGGA
 301 AAGAGCGAAG CATGATCAGC AGTTCCATAG TTTAAAGCCA ATATCTGGAT
 351 TCATTACTGG TGATCAAGCT AGAAACTTTT TTTTTCAATC TGGGTTACCT
 401 CAACCTGTTT TAGCACAGAT ATGGGCACTA GCTGACATGA ATAATGATGG
 451 AAGAATGGAT CAAGTGGAGT TTTCCATAGC TATGAAACTT ATCAAACTGA
 501 AGCTACAAGG ATATCAGCTA CCCTCTGCAC TTCCCCCTGT CATGAAACAG
 551 CAACCAGTTG CTATTTCTAG CGCACCAGCA TTTGGTATGG GAGGTATCGC
 601 CAGCATGCCA CCGCTTACAG CTGTTGCTCC AGTGCCAATG GGATCCATTC
 651 CAGTTGTTGG AATGTCTCCA ACCCTAGTAT CTTCTGTTCC CACAGCAGCT
 701 GTGCCCCCCC TGGCTAACGG GGCTCCCCCT GTTATACAAC CTCTGCCTGC
 751 ATTTGCTCAT CCTGCAGCCA CATTGCCAAA GAGTTCTTCC TTTAGTAGAT
 801 CTGGTCCAGG GTCACAACTA AACACTAAAT TACAAAAGGC ACAGTCATTT
 851 GATGTGGCCA GTGTCCCACC AGTGGCAGAG TGGGCTGTTC CTCAGTCATC
 901 AAGACTGAAA TACAGGCAAT TATTCAATAG TCATGACAAA ACTATGAGTG
 951 GACACTTAAC AGGTCCCCAA GCAAGAACTA TTCTTATGCA GTCAAGTTTA
1001 CCACAGGCTC AGCTGGCTTC AATATGGAAT CTTTCTGACA TTGATCAAGA
1051 TGGAAAACTT ACAGCAGAGG AATTTATCCT GGCAATGCAC CTCATTGATG
1101 TAGCTATGTC TGGCCAACCA CTGCCACCTG TCCTGCCTCC AGAATACATT
1151 CCACCTTCTT TTAGAAGAGT TCGATCTGGC AGTGGTATAT CTGTCATAAG
1201 CTCAACATCT GTAGATCAGA GGCTACCAGA GGAACCAGTT TTAGAAGATG
1251 AACAACAACA ATTAGAAAAG AAATTACCTG TAACGTTTGA AGATAAGAAG
1301 CGGGAGAACT TTGAACGTGG CAACCTGGAA CTGGAGAAAC GAAGGCAAGC
1351 TCTCCTGGAA CAGCAGCGCA AGGAGCAGGA GCGCCTGGCC CAGCTGGAGC
1401 GGGCGGAGCA GGAGAGGAAG GAGCGTGAGC GCCAGGAGCA AGAGCGCAAA
1451 AGACAACTGG AACTGGAGAA GCAACTGGAA AAGCAGCGGG AGCTAGAACG
1501 GCAGAGAGAG GAGGAGAGGA GGAAAGAAAT TGAGAGGCGA GAGGCTGCAA
1551 AACGGGAACT TGAAAGGCAA CGACAACTTG AGTGGGAACG GAATCGAAGG
1601 CAAGAACTAC TAAATCAAAG AAACAAAGAA CAAGAGGACA TAGTTGTACT
1651 GAAAGCAAAG AAAAAGACTT TGGAATTTGA ATTAGAAGCT CTAAATGATA
1701 AAAAGCATCA ACTAGAAGGG AAACTTCAAG ATATCAGATG TCGATTGACC
1751 ACCCAAAGGC AAGAAATTGA GAGCACAAAC AAATCTAGAG AGTTGAGAAT
1801 TGCCGAAATC ACCCATCTAC AGCAACAATT ACAGGAATCT CAGCAAATGC
1851 TTGGAAGACT TATTCCAGAA AAACAGATAC TCAATGACCA ATTAAAACAA
1901 GTTCAGCAGA ACAGTTTGCA CAGAGATTCA CTTGTTACAC TTAAAAGAGC
1951 CTTAGAAGCA AAAGAACTAG CTCGGCAGCA CCTACGAGAC CAACTGGATG
2001 AAGTGGAGAA AGAAACTAGA TCAAAACTAC AGGAGATTGA TATTTTCAAT
2051 AATCAGCTGA AGGAACTAAG AGAAATACAC AATAAGCAAC AACTCCAGAA
```

Figure 10

2101 GCAAAAGTCC ATGGAGGCTG AACGACTGAA ACAGAAAGAA CAAGAACGAA
2151 AGATCATAGA ATTAGAAAAA CAAAAAGAAG AAGCCCAAAG ACGAGCTCAG
2201 GAAAGGGACA AGCAGTGGCT GGAGCATGTG CAGCAGGAGG ACGAGCATCA
2251 GAGACCAAGA AAACTCCACG AAGAGGAAAA ACTGAAAAGG GAGGAGAGTG
2301 TCAAAAAGAA GGATGGCGAG GAAAAAGGCA AACAGGAAGC ACAAGACAAG
2351 CTGGGTCGGC TTTTCCATCA ACACCAAGAA CCAGCTAAGC CAGCTGTCCA
2401 GGCACCCTGG TCCACTGCAG AAAAAGGTCC ACTTACCATT TCTGCACAGG
2451 AAAATGTAAA AGTGGTGTAT TACCGGGCAC TGTACCCCTT TGAATCCAGA
2501 AGCCATGATG AAATCACTAT CCAGCCAGGA GACATAGTCA TGGTGGATGA
2551 AAGCCAAACT GGAGAACCCG GCTGGCTTGG AGGAGAATTA AAAGGAAAGA
2601 CAGGGTGGTT CCCTGCAAAC TATGCAGAGA AAATCCCAGA AAATGAGGTT
2651 CCCGCTCCAG TGAAACCAGT GACTGATTCA ACATCTGCCC CTGCCCCCAA
2701 ACTGGCCTTG CGTGAGACCC CCGCCCCTTT GGCAGTAACC TCTTCAGAGC
2751 CCTCCACGAC CCCTAATAAC TGGGCCGACT TCAGCTCCAC GTGGCCCACC
2801 AGCACGAATG AGAAACCAGA AACGGATAAC TGGGATGCAT GGGCAGCCCA
2851 GCCCTCTCTC ACCGTTCCAA GTGCCGGCCA GTTAAGGCAG AGGTCCGCCT
2901 TTACTCCAGC CACGGCCACT GGCTCCTCCC CGTCTCCTGT GCTAGGCCAG
2951 GGTGAAAAGG TGGAGGGGCT ACAAGCTCAA GCCCTATATC CTTGGAGAGC
3001 CAAAAAAGAC AACCACTTAA ATTTTAACAA AAATGATGTC ATCACCGTCC
3051 TGGAACAGCA AGACATGTGG TGGTTTGGAG AAGTTCAAGG TCAGAAGGGT
3101 TGGTTCCCCA AGTCTTACGT GAAACTCATT TCAGGGCCCA TAAGGAAGTC
3151 TACAAGCATG GATTCTGGTT CTTCAGAGAG TCCTGCTAGT CTAAAGCGAG
3201 TAGCCTCTCC AGCAGCCAAG CCGGTCGTTT CGGGAGAAGA ATTTATTGCC
3251 ATGTACACTT ACGAGAGTTC TGAGCAAGGA GATTTAACCT TTCAGCAAGG
3301 GGATGTGATT TTGGTTACCA AGAAAGATGG TGACTGGTGG ACAGGAACAG
3351 TGGGCGACAA GGCCGGAGTC TTCCCTTCTA ACTATGTGAG GCTTAAAGAT
3401 TCAGAGGGCT CTGGAACTGC TGGGAAAACA GGGAGTTTAG GAAAAAAACC
3451 TGAAATTGCC CAGGTTATTG CCTCATACAC CGCCACCGGC CCCGAGCAGC
3501 TCACTCTCGC CCCTGGTCAG CTGATTTTGA TCCGAAAAAA GAACCCAGGT
3551 GGATGGTGGG AAGGAGAGCT GCAAGCACGT GGGAAAAAGC GCCAGATAGG
3601 CTGGTTCCCA GCTAATTATG TAAAGCTTCT AAGCCCTGGG ACGAGCAAAA
3651 TCACTCCAAC AGAGCCACCT AAGTCAACAG CATTAGCGGC AGTGTGCCAG
3701 GTGATTGGGA TGTACGACTA CACCGCGCAG AATGACGATG AGCTGGCCTT
3751 CAACAAGGGC CAGATCATCA ACGTCCTCAA CAAGGAGGAC CCTGACTGGT
3801 GGAAAGGAGA AGTCAATGGA CAAGTGGGGC TCTTCCCATC CAATTATGTG
3851 AAGCTGACCA CAGACATGGA CCCAAGCCAG CAATGAATCA TATGTTGTCC
3901 ATCCCCCCCT CAGGCTTGAA AGTCCTTTTG TGGCTTTCCT AGTTACTCAA
3951 ATTGACTTTC CCCCACCTTT GCACAGGTGC TTTCAATAGT TTTAAAATTA
4001 TTTTTAAATA TATATTTTAG CTTTTTAATA AACAAAATAA ATAAATGACT
4051 TCTTTGCTAT TTTGGTTTTG CAAAAAGACC CACTATCAAG GAATGCTGCA
4101 TGTGCTATTA AAAATTGTTC CAAATGTCCA TAAATCTGAG ACTTGATGTA
4151 TTTTTTCATT TTGTCCAGTG TTACCAACTA AATTGTGCAG TTTGGGGCTT
4201 TTCCCCCTTA CCATAGAAGT GCAGAGGAGT TCAGTATCTC TGTTTTAAAG

Figure 10

```
4251 ACGTATAGAA TGAGCCCAAT TAAAGCGAAG GTGTTTGTGC TTGTTTGTGT
4301 GTATCAGCTG TACCTTGTTG AGCATGTAAT ACATCCTGTA CATAAGAAAT
4351 TAGTTCTTTC CATGGCAAAG CTATTACCTT GTACGATGCT CTAATCATAT
4401 TGCATTTAAT TTTATTTTGC ACAGTGACCT TGTAGCCACA TGAGAAAGCA
4451 CTCTGTGTTT TTGTTCGGTC TCAGATTTAT CTGGTTGAGT TGGTGTTTTG
4501 TTTGGGGTTT TTAATTTTGC GTGTTTGCAT AGCATAAAAT CAGTAGACAA
4551 CACCACTGAG GTCGTTACGA TCAACGATAT CCACAGTCTC TTTTTAGTCT
4601 CTGTTACATG AAGTTTTATT CCAGTTACTT TCATGGAAT GACCTATTTT
4651 GAACAAGTAA TTTTCTTGAC AAGAAAGAAT GTATAGAAGT CTCCCTGCAA
4701 TTAATTTCCA ATGTTTACAT TTTTTAACTA GACTGTGGAA TTTCTACAGA
4751 TTAATATGAA ATGGAGCTCA TGGTCCGTTT GTGTGTTAGA TATGCTGTAG
4801 CTGAAGCCCT GTTTGTCTTT TAAACACTAG TTGGAAGCTC TCAATAAAAA
4851 TGCCTGCTGC TCACAGCACA GAAAATGGGG CAGGGGAGC CTCAAGCACA
4901 ATCTAGCTGT CCTCCTAAAG ACTCTGTAAT GCTCACTCCC CTCGCGTTCT
4951 CCCGGCGCTG TCGGGAGGCT GTGCTGGTGG TCGTGTAGAG GTCCTTCTCC
5001 TTTCACATGG TGCAGAGAGC GAGGACCTCT CCTCCTCGTT CAGTTGCACT
5051 TCAGTATTTT CACGGATATG AATGTAAAAT ATATAAATAT ATAAACCTGC
5101 GGCTTTAACA ACTGTAATAC AACCTTTTGA ATTAGTTCCG TGTATAGATA
5151 ATTAAATTCT TCATACAAAA GTTAAAAAAA AAAAAAAAA AAAAA
```

Figure 10

Translated Protein Sequence #11

```
   1 MAQFPTPFGG SLDIWAITVE ERAKHDQQFH SLKPISGFIT GDQARNFFFQ
  51 SGLPQPVLAQ IWALADMNND GRMDQVEFSI AMKLIKLKLQ GYQLPSALPP
 101 VMKQQPVAIS SAPAFGMGGI ASMPPLTAVA PVPMGSIPVV GMSPTLVSSV
 151 PTAAVPPLAN GAPPVIQPLP AFAHPAATLP KSSSFSRSGP GSQLNTKLQK
 201 AQSFDVASVP PVAEWAVPQS SRLKYRQLFN SHDKTMSGHL TGPQARTILM
 251 QSSLPQAQLA SIWNLSDIDQ DGKLTAEEFI LAMHLIDVAM SGQPLPPVLP
 301 PEYIPPSFRR VRSGSGISVI SSTSVDQRLP EEPVLEDEQQ QLEKKLPVTF
 351 EDKKRENFER GNLELEKRRQ ALLEQQRKEQ ERLAQLERAE QERKERERQE
 401 QERKRQLELE KQLEKQRELE RQREEERRKE IERREAAKRE LERQRQLEWE
 451 RNRRQELLNQ RNKEQEDIVV LKAKKKTLEF ELEALNDKKH QLEGKLQDIR
 501 CRLTTQRQEI ESTNKSRELR IAEITHLQQQ LQESQQMLGR LIPEKQILND
 551 QLKQVQQNSL HRDSLVTLKR ALEAKELARQ HLRDQLDEVE KETRSKLQEI
 601 DIFNNQLKEL REIHNKQQLQ KQKSMEAERL KQKEQERKII ELEKQKEEAQ
 651 RRAQERDKQW LEHVQQEDEH QRPRKLHEEE KLKREESVKK KDGEEKGKQE
 701 AQDKLGRLFH QHQEPAKPAV QAPWSTAEKG PLTISAQENV KVVYYRALYP
 751 FESRSHDEIT IQPGDIVMVD ESQTGEPGWL GGELKGKTGW FPANYAEKIP
 801 ENEVPAPVKP VTDSTSAPAP KLALRETPAP LAVTSSEPST TPNNWADFSS
 851 TWPTSTNEKP ETDNWDAWAA QPSLTVPSAG QLRQRSAFTP ATATGSSPSP
 901 VLGQGEKVEG LQAQALYPWR AKKDNHLNFN KNDVITVLEQ QDMWWFGEVQ
 951 GQKGWFPKSY VKLISGPIRK STSMDSGSSE SPASLKRVAS PAAKPVVSGE
1001 EFIAMYTYES SEQGDLTFQQ GDVILVTKKD GDWWTGTVGD KAGVFPSNYV
1051 RLKDSEGSGT AGKTGSLGKK PEIAQVIASY TATGPEQLTL APGQLILIRK
1101 KNPGGWWEGE LQARGKKRQI GWFPANYVKL LSPGTSKITP TEPPKSTALA
1151 AVCQVIGMYD YTAQNDDELA FNKGQIINVL NKEDPDWWKG EVNGQVGLFP
1201 SNYVKLTTDM DPSQQ*
``` whole protein sequence:

```
   1 EWRRQGRERS LVAP*YGGSR GRIPSGLRDG QRGGRGWCAG LRLLRPSQRR
  51 VSGTDLSLGR QRGPARR*GV D*QGKSNRTM AQFPTPFGGS LDIWAITVEE
 101 RAKHDQQFHS LKPISGFITG DQARNFFFQS GLPQPVLAQI WALADMNNDG
 151 RMDQVEFSIA MKLIKLKLQG YQLPSALPPV MKQQPVAISS APAFGMGGIA
 201 SMPPLTAVAP VPMGSIPVVG MSPTLVSSVP TAAVPPLANG APPVIQPLPA
 251 FAHPAATLPK SSSFSRSGPG SQLNTKLQKA QSFDVASVPP VAEWAVPQSS
 301 RLKYRQLFNS HDKTMSGHLT GPQARTILMQ SSLPQAQLAS IWNLSDIDQD
 351 GKLTAEEFIL AMHLIDVAMS GQPLPPVLPP EYIPPSFRRV RSGSGISVIS
 401 STSVDQRLPE EPVLEDEQQQ LEKKLPVTFE DKKRENFERG NLELEKRRQA
 451 LLEQQRKEQE RLAQLERAEQ ERKERERQEQ ERKRQLELEK QLEKQRELER
 501 QREEERRKEI ERREAAKREL ERQRQLEWER NRRQELLNQR NKEQEDIVVL
 551 KAKKKTLEFE LEALNDKKHQ LEGKLQDIRC RLTTQRQEIE STNKSRELRI
 601 AEITHLQQQL QESQQMLGRL IPEKQILNDQ LKQVQQNSLH RDSLVTLKRA
 651 LEAKELARQH LRDQLDEVEK ETRSKLQEID IFNNQLKELR EIHNKQQLQK
 701 QKSMEAERLK QKEQERKIIE LEKQKEEAQR RAQERDKQWL EHVQQEDEHQ
 751 RPRKLHEEEK LKREESVKKK DGEEKGKQEA QDKLGRLFHQ HQEPAKPAVQ
 801 APWSTAEKGP LTISAQENVK VVYYRALYPF ESRSHDEITI QPGDIVMVDE
 851 SQTGEPGWLG GELKGKTGWF PANYAEKIPE NEVPAPVKPV TDSTSAPAPK
 901 LALRETPAPL AVTSSEPSTT PNNWADFSST WPTSTNEKPE TDNWDAWAAQ
 951 PSLTVPSAGQ LRQRSAFTPA TATGSSPSPV LGQGEKVEGL QAQALYPWRA
1001 KKDNHLNFNK NDVITVLEQQ DMWWFGEVQG QKGWFPKSYV KLISGPIRKS
1051 TSMDSGSSES PASLKRVASP AAKPVVSGEE FIAMYTYESS EQGDLTFQQG
1101 DVILVTKKDG DWWTGTVGDK AGVFPSNYVR LKDSEGSGTA GKTGSLGKKP
1151 EIAQVIASYT ATGPEQLTLA PGQLILIRKK NPGGWWEGEL QARGKKRQIG
1201 WFPANYVKLL SPGTSKITPT EPPKSTALAA VCQVIGMYDY TAQNDDELAF
1251 NKGQIINVLN KEDPDWWKGE VNGQVGLFPS NYVKLTTDMD PSQQ*IICCP
1301 SPPQA*KSFC GFPSYSN*LS PTFAQVLSIV LKLFLNIYFS FLINKINK*L
1351 LCYFGFAKRP TIKECCMCY* KLFQMSINLR LDVFFHFVQC YQLNCAVWGF
1401 SPLP*KCRGV QYLCFKDV*N EPN*SEGVCA CLCVSAVPC* ACNTSCT*EI
1451 SSFHGKAITL YDALIILHLI LFCTVTL*PH EKALCVFVRS QIYLVELVFC
1501 LGFLILRVCI A*NQ*TTPLR SLRSTISTVS F*SLLHEVLF QLLFME*PIL
1551 NK*FS*QERM YRSLPAINFQ CLHFLTRLWN FYRLI*NGAH GPFVC*ICCS
1601 *SPVCLLNTS WKLSIKMPAA HSTENGAGGA SSTI*LSS*R LCNAHSPRVL
1651 PALSGGCAGG RVEVLLLSHG AESEDLSSSF SCTSVFSRI* M*NI*IYKPA
1701 ALTTVIQPFE LVPCIDN*IL HTKVKKKKKK K
```

Figure 11

```
   1 CGGGGATGGT GTGCGGGGCT GCGGCTCCTG CGTCCCTCCC AGCGGCGCGT
  51 GAGCGGCACT GATTTGTCCC TGGGGCGGCA GCGCGGACCC GCCCGGAGAT
 101 GAGGCGTCGA TTAGCAAGGT AAAAGTAACA GAACCATGGC TCAGTTTCCA
 151 ACACCTTTTG GTGGCAGCCT GGATATCTGG GCCATAACTG TAGAGGAAAG
 201 AGCGAAGCAT GATCAGCAGT TCCATAGTTT AAAGCCAATA TCTGGATTCA
 251 TTACTGGTGA TCAAGCTAGA AACTTTTTTT TTCAATCTGG GTTACCTCAA
 301 CCTGTTTTAG CACAGATATG GCACTAGCT GACATGAATA ATGATGGAAG
 351 AATGGATCAA GTGGAGTTTT CCATAGCTAT GAAACTTATC AAACTGAAGC
 401 TACAAGGATA TCAGCTACCC TCTGCACTTC CCCCTGTCAT GAAACAGCAA
 451 CCAGTTGCTA TTTCTAGCGC ACCAGCATTT GGTATGGGAG GTATCGCCAG
 501 CATGCCACCG CTTACAGCTG TTGCTCCAGT GCCAATGGGA TCCATTCCAG
 551 TTGTTGGAAT GTCTCCAACC CTAGTATCTT CTGTTCCCAC AGCAGCTGTG
 601 CCCCCCCTGG CTAACGGGGC TCCCCCTGTT ATACAACCTC TGCCTGCATT
 651 TGCTCATCCT GCAGCCACAT TGCCAAAGAG TTCTTCCTTT AGTAGATCTG
 701 GTCCAGGGTC ACAACTAAAC ACTAAATTAC AAAAGGCACA GTCATTTGAT
 751 GTGGCCAGTG TCCCACCAGT GGCAGAGTGG GCTGTTCCTC AGTCATCAAG
 801 ACTGAAATAC AGGCAATTAT CAATAGTCA TGACAAAACT ATGAGTGGAC
 851 ACTTAACAGG TCCCCAAGCA AGAACTATTC TTATGCAGTC AAGTTTACCA
 901 CAGGCTCAGC TGGCTTCAAT ATGGAATCTT TCTGACATTG ATCAAGATGG
 951 AAAACTTACA GCAGAGGAAT TTATCCTGGC AATGCACCTC ATTGATGTAG
1001 CTATGTCTGG CCAACCACTG CCACCTGTCC TGCCTCCAGA ATACATTCCA
1051 CCTTCTTTTA GAAGAGTTCG ATCTGGCAGT GGTATATCTG TCATAAGCTC
1101 AACATCTGTA GATCAGAGGC TACCAGAGGA ACCAGTTTTA GAAGATGAAC
1151 AACAACAATT AGAAAAGAAA TTACCTGTAA CGTTTGAAGA TAAGAAGCGG
1201 GAGAACTTTG AACGTGGCAA CCTGGAACTG GAGAAACGAA GGCAAGCTCT
1251 CCTGGAACAG CAGCGCAAGG AGCAGGAGCG CCTGGCCCAG CTGGAGCGGG
1301 CGGAGCAGGA GAGGAAGGAG CGTGAGCGCC AGGAGCAAGA GCGCAAAAGA
1351 CAACTGGAAC TGGAGAAGCA ACTGGAAAAG CAGCGGGAGC TAGAACGGCA
1401 GAGAGAGGAG GAGAGGAGGA AAGAAATTGA GAGGCGAGAG GCTGCAAAAC
1451 GGGAACTTGA AAGGCAACGA CAACTTGAGT GGGAACGGAA TCGAAGGCAA
1501 GAACTACTAA ATCAAAGAAA CAAAGAACAA GAGGACATAG TTGTACTGAA
1551 AGCAAAGAAA AAGACTTTGG AATTTGAATT AGAAGCTCTA AATGATAAAA
1601 AGCATCAACT AGAAGGGAAA CTTCAAGATA TCAGATGTCG ATTGACCACC
1651 CAAAGGCAAG AAATTGAGAG CACAAACAAA TCTAGAGAGT TGAGAATTGC
1701 CGAAATCACC CATCTACAGC AACAATTACA GGAATCTCAG CAAATGCTTG
1751 GAAGACTTAT TCCAGAAAAA CAGATACTCA ATGACCAATT AAAACAAGTT
1801 CAGCAGAACA GTTTGCACAG AGATTCACTT GTTACACTTA AAAGAGCCTT
1851 AGAAGCAAAA GAACTAGCTC GGCAGCACCT ACGAGACCAA CTGGATGAAG
1901 TGGAGAAAGA AACTAGATCA AAACTACAGG AGATTGATAT TTTCAATAAT
1951 CAGCTGAAGG AACTAAGAGA AATACACAAT AAGCAACAAC TCCAGAAGCA
2001 AAAGTCCATG GAGGCTGAAC GACTGAAACA GAAAGAACAA GAACGAAAGA
2051 TCATAGAATT AGAAAAAAAA AAAAAAAA
```

Figure 12

5 translated Protein sequence:

```
  1 MAQFPTPFGG SLDIWAITVE ERAKHDQQFH SLKPISGFIT GDQARNFFFQ
 51 SGLPQPVLAQ IWALADMNND GRMDQVEFSI AMKLIKLKLQ GYQLPSALPP
101 VMKQQPVAIS SAPAFGMGGI ASMPPLTAVA PVPMGSIPVV GMSPTLVSSV
151 PTAAVPPLAN GAPPVIQPLP AFAHPAATLP KSSSFSRSGP GSQLNTKLQK
201 AQSFDVASVP PVAEWAVPQS SRLKYRQLFN SHDKTMSGHL TGPQARTILM
251 QSSLPQAQLA SIWNLSDIDQ DGKLTAEEFI LAMHLIDVAM SGQPLPPVLP
301 PEYIPPSFRR VRSGSGISVI SSTSVDQRLP EEPVLEDEQQ QLEKKLPVTF
351 EDKKRENFER GNLELEKRRQ ALLEQQRKEQ ERLAQLERAE QERKERERQE
401 QERKRQLELE KQLEKQRELE RQREEERRKE IERREAAKRE LERQRQLEWE
451 RNRRQELLNQ RNKEQEDIVV LKAKKKTLEF ELEALNDKKH QLEGKLQDIR
501 CRLTTQRQEI ESTNKSRELR IAEITHLQQQ LQESQQMLGR LIPEKQILND
551 QLKQVQQNSL HRDSLVTLKR ALEAKELARQ HLRDQLDEVE KETRSKLQEI
601 DIFNNQLKEL REIHNKQQLQ KQKSMEAERL KQKEQERKII ELEKKKKK
``` whole sequence

```
  1 RGWCAGLRLL RPSQRRVSGT DLSLGRQRGP ARR*GVD*QG KSNRTMAQFP
 51 TPFGGSLDIW AITVEERAKH DQQFHSLKPI SGFITGDQAR NFFFQSGLPQ
101 PVLAQIWALA DMNNDGRMDQ VEFSIAMKLI KLKLQGYQLP SALPPVMKQQ
151 PVAISSAPAF GMGGIASMPP LTAVAPVPMG SIPVVGMSPT LVSSVPTAAV
201 PPLANGAPPV IQPLPAFAHP AATLPKSSSF SRSGPGSQLN TKLQKAQSFD
251 VASVPPVAEW AVPQSSRLKY RQLFNSHDKT MSGHLTGPQA RTILMQSSLP
301 QAQLASIWNL SDIDQDGKLT AEEFILAMHL IDVAMSGQPL PPVLPPEYIP
351 PSFRRVRSGS GISVISSTSV DQRLPEEPVL EDEQQQLEKK LPVTFEDKKR
401 ENFERGNLEL EKRRQALLEQ QRKEQERLAQ LERAEQERKE RERQEQERKR
451 QLELEKQLEK QRELERQREE ERRKEIERRE AAKRELERQR QLEWERNRRQ
501 ELLNQRNKEQ EDIVVLKAKK KTLEFELEAL NDKKHQLEGK LQDIRCRLTT
551 QRQEIESTNK SRELRIAEIT HLQQQLQESQ QMLGRLIPEK QILNDQLKQV
601 QQNSLHRDSL VTLKRALEAK ELARQHLRDQ LDEVEKETRS KLQEIDIFNN
651 QLKELREIHN KQQLQKQKSM EAERLKQKEQ ERKIIELEKK KKK
```

Figure 13

```
   1 GACCACCCAA AGGCAAGAAA TTGAGAGCAC AAACAAATCT AGAGAGTTGA
  51 GAATTGCCGA AATCACCCAT CTACAGCAAC AATTACAGGA ATCTCAGCAA
 101 ATGCTTGGAA GACTTATTCC AGAAAAACAG ATACTCAATG ACCAATTAAA
 151 ACAAGTTCAG CAGAACAGTT TGCACAGAGA TTCACTTGTT ACACTTAAAA
 201 GAGCCTTAGA AGCAAAAGAA CTAGCTCGGC AGCACCTACG AGACCAACTG
 251 GATGAAGTGG AGAAAGAAAC TAGATCAAAA CTACAGGAGA TTGATATTTT
 301 CAATAATCAG CTGAAGGAAC TAAGAGAAAT ACACAATAAG CAACAACTCC
 351 AGAAGCAAAA GTCCATGGAG GCTGAACGAC TGAAACAGAA AGAACAAGAA
 401 CGAAAGATCA TAGAATTAGA AAAACAAAAA GAAGAAGCCC AAAGACGAGC
 451 TCAGGAAAGG GACAAGCAGT GGCTGGAGCA TGTGCAGCAG GAGGACGAGC
 501 ATCAGAGACC AAGAAAACTC CACGAAGAGG AAAAACTGAA AAGGGAGGAG
 551 AGTGTCAAAA AGAAGGATGG CGAGGAAAAA GGCAAACAGG AAGCACAAGA
 601 CAAGCTGGGT CGGCTTTTCC ATCAACACCA AGAACCAGCT AAGCCAGCTG
 651 TCCAGGCACC CTGGTCCACT GCAGAAAAAG GTCCACTTAC CATTTCTGCA
 701 CAGGAAAATG TAAAAGTGGT GTATTACCGG GCACTGTACC CCTTTGAATC
 751 CAGAAGCCAT GATGAAATCA CTATCCAGCC AGGAGACATA GTCATGGTGG
 801 ATGAAAGCCA AACTGGAGAA CCCGGCTGGC TTGGAGGAGA ATTAAAAGGA
 851 AAGACAGGGT GGTTCCCTGC AAACTATGCA GAGAAAATCC AGAAAATGA
 901 GGTTCCCGCT CCAGTGAAAC CAGTGACTGA TTCAACATCT GCCCCTGCCC
 951 CCAAACTGGC CTTGCGTGAG ACCCCCGCCC CTTTGGCAGT AACCTCTTCA
1001 GAGCCCTCCA CGACCCCTAA TAACTGGGCC GACTTCAGCT CCACGTGGCC
1051 CACCAGCACG AATGAGAAAC CAGAAACGGA TAACTGGGAT GCATGGGCAG
1101 CCCAGCCCTC TCTCACCGTT CCAAGTGCCG CCAGTTAAG GCAGAGGTCC
1151 GCCTTTACTC CAGCCACGGC CACTGGCTCC TCCCCGTCTC CTGTGCTAGG
1201 CCAGGGTGAA AAGGTGGAGG GGCTACAAGC TCAAGCCCTA TATCCTTGGA
1251 GAGCCAAAAA AGACAACCAC TTAAATTTTA ACAAAAATGA TGTCATCACC
1301 GTCCTGGAAC AGCAAGACAT GTGGTGGTTT GGAGAAGTTC AAGGTCAGAA
1351 GGGTTGGTTC CCCAAGTCTT ACGTGAAACT CATTTCAGGG CCCATAAGGA
1401 AGTCTACAAG CATGGATTCT GGTTCTTCAG AGAGTCCTGC TAGTCTAAAG
1451 CGAGTAGCCT CTCCAGCAGC CAAGCCGGTC GTTTCGGGAG AAGAAATTGC
1501 CCAGGTTATT GCCTCATACA CCGCCACCGG CCCCGAGCAG CTCACTCTCG
1551 CCCCTGGTCA GCTGATTTTG ATCCGAAAAA AGAACCCAGG TGGATGGTGG
1601 GAAGGAGAGC TGCAAGCACG TGGGAAAAAG CGCCAGATAG GCTGGTTCCC
1651 AGCTAATTAT GTAAAGCTTC TAAGCCCTGG GACGAGCAAA ATCACTCCAA
1701 CAGAGCCACC TAAGTCAACA GCATTAGCGG CAGTGTGCCA GGTGATTGGG
1751 ATGTACGACT ACACCGCGCA GAATGACGAT GAGCTGGCCT TCAACAAGGG
1801 CCAGATCATC AACGTCCTCA ACAAGGAGGA CCCTGACTGG TGGAAAGGAG
1851 AAGTCAATGG ACAAGTGGGG CTCTTCCCAT CCAATTATGT GAAGCTGACC
1901 ACAGACATGG ACCCAAGCCA GCAATGAATC ATATGTTGTC CATCCCCCCC
1951 TCAGGCTTGA AAGTCCTTTT GTGGCTTTCC TAGTTACTCA AATTGACTTT
2001 CCCCCACCTT TGCACAGGTG CTTTCAATAG TTTTAAAATT ATTTTTAAAT
```

Figure 14

```
2051 ATATATTTTA GCTTTTTAAT AAACAAAATA AATAAATGAC TTCTTTGCTA
2101 TTTTGGTTTT GCAAAAAGAC CCACTATCAA GGAATGCTGC ATGTGCTATT
2151 AAAAATTGTT CCAAATGTCC ATAAATCTGA GACTTGATGT ATTTTTTCAT
2201 TTTGTCCAGT GTTACCAACT AAATTGTGCA GTTTGGGGCT TTTCCCCCTT
2251 ACCATAGAAG TGCAGAGGAG TTCAGTATCT CTGTTTTAAA GACGTATAGA
2301 ATGAGCCCAA TTAAAGCGAA GGTGTTTGTG CTTGTTTGTG TGTATCAGCT
2351 GTACCTTGTT GAGCATGTAA TACATCCTGT ACATAAGAAA TTAGTTCTTT
2401 CCATGGCAAA GCTATTACCT TGTACGATGC TCTAATCATA TTGCATTTAA
2451 TTTTATTTTG CACAGTGACC TTGTAGCCAC ATGAGAAAGC ACTCTGTGTT
2501 TTTGTTCGGT CTCAGATTTA TCTGGTTGAG TTGGTGTTTT GTTTGGGGTT
2551 TTTAATTTTG CGTGTTTGCA TAGCATAAAA TCAGTAGACA ACACCACTGA
2601 GGTCGTTACG ATCAACGATA TCCACAGTCT CTTTTTAGTC TCTGTTACAT
2651 GAAGTTTTAT TCCAGTTACT TTTCATGGAA TGACCTATTT TGAACAAGTA
2701 ATTTTCTTGA CAAGAAAGAA TGTATAGAAG TCTCCCTGCA ATTAATTTCC
2751 AATGTTTACA TTTTTTAACT AGACTGTGGA ATTTCTACAG ATTAATATGA
2801 AATGGAGCTC ATGGTCCGTT TGTGTGTTAG ATATGCTGTA GCTGAAGCCC
2851 TGTTTGTCTT TTAAACACTA GTTGGAAGCT CTCAATAAAA ATGCCTGCTG
2901 CTCACAGCAC AGAAAATGGG GCAGGGGGAG CCTCAAGCAC AATCTAGCTG
2951 TCCTCCTAAA GACTCTGTAA TGCTCACTCC CCTCGCGTTC TCCCGGCGCT
3001 GTCGGGAGGC TGTGCTGGTG GTCGTGTAAG GTCCTTCTCC TTTCACATGG
3051 TGCAGAGAGC GAGGACCTCT CCTCCTCGTT CAGTTGCACT TCAGTATTTT
3101 CACGGATATG AATGTAAAAT ATATAAATAT ATAAACCTGC GGCTTTAACA
3151 ACTGTAATAC AACCTTTTGA ATTAGTTCCG TGTATAGATA ATTAAATTCT
3201 TCATACAAAA GTTAAAAAAA AAAAAAAAA A
```

Figure 14

9 translated protein sequence:

```
  1 TTQRQEIEST NKSRELRIAE ITHLQQQLQE SQQMLGRLIP EKQILNDQLK
 51 QVQQNSLHRD SLVTLKRALE AKELARQHLR DQLDEVEKET RSKLQEIDIF
101 NNQLKELREI HNKQQLQKQK SMEAERLKQK EQERKIIELE KQKEEAQRRA
151 QERDKQWLEH VQQEDEHQRP RKLHEEEKLK REESVKKKDG EEKGKQEAQD
201 KLGRLFHQHQ EPAKPAVQAP WSTAEKGPLT ISAQENVKVV YYRALYPFES
251 RSHDEITIQP GDIVMVDESQ TGEPGWLGGE LKGKTGWFPA NYAEKIPENE
301 VPAPVKPVTD STSAPAPKLA LRETPAPLAV TSSEPSTTPN NWADFSSTWP
351 TSTNEKPETD NWDAWAAQPS LTVPSAGQLR QRSAFTPATA TGSSPSPVLG
401 QGEKVEGLQA QALYPWRAKK DNHLNFNKND VITVLEQQDM WWFGEVQGQK
451 GWFPKSYVKL ISGPIRKSTS MDSGSSESPA SLKRVASPAA KPVVSGEEIA
501 QVIASYTATG PEQLTLAPGQ LILIRKKNPG GWWEGELQAR GKKRQIGWFP
551 ANYVKLLSPG TSKITPTEPP KSTALAAVCQ VIGMYDYTAQ NDDELAFNKG
601 QIINVLNKED PDWWKGEVNG QVGLFPSNYV KLTTDMDPSQ Q*
```

Whole protein sequence

```
  1 TTQRQEIEST NKSRELRIAE ITHLQQQLQE SQQMLGRLIP EKQILNDQLK
 51 QVQQNSLHRD SLVTLKRALE AKELARQHLR DQLDEVEKET RSKLQEIDIF
101 NNQLKELREI HNKQQLQKQK SMEAERLKQK EQERKIIELE KQKEEAQRRA
151 QERDKQWLEH VQQEDEHQRP RKLHEEEKLK REESVKKKDG EEKGKQEAQD
201 KLGRLFHQHQ EPAKPAVQAP WSTAEKGPLT ISAQENVKVV YYRALYPFES
251 RSHDEITIQP GDIVMVDESQ TGEPGWLGGE LKGKTGWFPA NYAEKIPENE
301 VPAPVKPVTD STSAPAPKLA LRETPAPLAV TSSEPSTTPN NWADFSSTWP
351 TSTNEKPETD NWDAWAAQPS LTVPSAGQLR QRSAFTPATA TGSSPSPVLG
401 QGEKVEGLQA QALYPWRAKK DNHLNFNKND VITVLEQQDM WWFGEVQGQK
451 GWFPKSYVKL ISGPIRKSTS MDSGSSESPA SLKRVASPAA KPVVSGEEIA
501 QVIASYTATG PEQLTLAPGQ LILIRKKNPG GWWEGELQAR GKKRQIGWFP
551 ANYVKLLSPG TSKITPTEPP KSTALAAVCQ VIGMYDYTAQ NDDELAFNKG
601 QIINVLNKED PDWWKGEVNG QVGLFPSNYV KLTTDMDPSQ Q*IICCPSPP
651 QA*KSFCGFP SYSN*LSPTF AQVLSIVLKL FLNIYFSFLI NKINK*LLCY
701 FGFAKRPTIK ECCMCY*KLF QMSINLRLDV FFHFVQCYQL NCAVWGFSPL
751 P*KCRGVQYL CFKDV*NEPN *SEGVCACLC VSAVPC*ACN TSCT*EISSF
801 HGKAITLYDA LIILHLILFC TVTL*PHEKA LCVFVRSQIY LVELVFCLGF
851 LILRVCIA*N Q*TTPLRSLR STISTVSF*S LLHEVLFQLL FME*PILNK*
901 FS*QERMYRS LPAINFQCLH FLTRLWNFYR LI*NGAHGPF VC*ICCS*SP
951 VCLLNTSWKL SIKMPAAHST ENGAGGASST I*LSS*RLCN AHSPRVLPAL
1001 SGGCAGGRVR SFSFHMVQRA RTSPPRSVAL QYFHGYECKI YKYINLRL*Q
1051 L*YNLLN*FR V*IIKFFIQK LKKKKK
```

ISOLATED SH3 GENES ASSOCIATES WITH MYELOPROLIFERATIVE DISORDERS AND LEUKEMIA AND USES THEREOF

This application claims the benefit of provisional application No. 60/082,007 filed Apr. 16, 1998.

RESEARCH SUPPORT

The research leading to the present invention was supported in part by the Clinical Molecular Core grant NICHD P01HD17449 from the National Institutes of Health. The government may have certain rights in the present invention.

FIELD OF THE INVENTION

The present invention relates to the isolated nucleic acids and corresponding amino acids of a series of SH3 genes, analogs, fragments, mutants, and variants thereof. The invention provides polypeptides, fusion proteins, chimerics, antisense molecules, antibodies, and uses thereof. Also, this invention is directed to diagnostic methods of determining whether a subject has a megakaryocytic abnormality, myeloproliferative disorder, platelet disorder, hematopoietic disorder, or leukemia, or disorders associated with abnormal neural development, and therapeutic treatments thereof.

BACKGROUND OF THE INVENTION

Down syndrome, caused by trisomy of human chromosome 21 (HSA21), is the most common autosomal form of mental retardation. The first report describing an association between Down syndrome (DS) and leukemia, which are an important cause of morbidity and mortality worldwide, was presented in 1930. Since that time, the increased incidence of acute leukemia in patients with DS has been clearly established. However, the M7 subtype, AMKL, acute megakaryoblastic leukemia has been found to be common in DS but relatively rare in non-DS. An instability in the control of bone marrow proliferation has been hypothesized as a predisposing factor. The incidence of acute myelogenous leukemia patients with DS has been noted by some to be similar to that in children without mongolism. Chromosome 21 is a model for the study of human chromosomal aneuploidy, and the construction of its physical and transcriptional maps is a necessary step in understanding the molecular basis of aneuploidy-dependent phenotypes.

Human chromosome 21 has a nearly complete physical map with a well-characterized contiguous set of overlapping YACs spanning most of its length (Chumakov et al., 1992; Shimizu et al., 1995; Korenberg et al., 1995). The demand for sequence-ready contigs and clones for gene isolation efforts has prompted the construction of numerous higher resolution contigs in cosmids (Patil et al., 1994; Soeda et al., 1995) and, more recently, in P1-derived artificial chromosomes (PACs; Oegawa et al. 1996 and Hubert et al. (1997) Genomics 41:218–226). Considerable mapping efforts exist in the region from CBR to D21S55 due to the common duplication of the region in partially trisomic individuals with several phenotypic features of DS, including mental retardation. However, the distal and adjacent, 4- to 5-Mb D21S55 to MX1 region is also associated with DS-CHD as well as other characteristic features of DS (Korenberg et al., 1992, 1994).

Although full monosomy of chromosome 21 is usually lethal in utero, there are rare cases of individuals with chromosome 21 deletions who survive. These individuals exhibit a characteristic subset of clinical features including psychomotor and growth retardation, congenital heart disease, holoprosencephaly, microphthalmia, skeletal malformations, and genital hypoplasia. Megakaryocytic abnormalities is added to this set and define a minimal "overlap" region for this feature through the clinical, cytogenetic, and molecular analysis of four patients with overlapping deletions of chromosome 21 and thrombocytopenia.

Nonchimeric YACs span this interval with a few gaps but higher resolution physical maps are not available for most of the D21S55 to MX1 region. DEL21RW carries two interstitial deletions, one in 21q21.3–22.1 defined by YAC 62G5 through YAC 760H5, and the second in 21q22.2, deleting IFNAR through CBR. DEL21LS carries an interstitial deletion of 21q22.1 from YAC 760H5 through the AML1 gene. Korenberg et al. reported that the deletion of patient DEL21HJ includes D21S93 through AML1. DEL21SV has a possible terminal deletion, 21q22.13-qter, extending from just proximal to D21S324 through D21S123. The common deleted region, or overlap region, is therefore from D21S324 through AML1, a region of less than 2 Mb that contains only three known genes, AML1, KCNE1, and UNO2. Bone marrow examination of two of the patients, DEL21HJ and Del 21RW, showed normocellular marrow with normal myelopoiesis, normal erythropoiesis, and small, dysplastic megakaryocytes with hypolobated nuclei. These two patients have decreased platelet activation by agonists with normal platelet ultrastructures. All four patients have platelet dysfunction characterized by low platelet counts in the range of 31–113×10$^9$/L. Further, all four subjects with chromosome 21 deletions that do not include this region have normal number of platelets.

A 3' fragment of SH3P17 gene was found in a study to isolate SH3 domain containing genes (Sparks et al. 1996, *Nature Biotechnology* 14:741). This was mapped to 21 or large sub-region of 21 by a number of groups by using database matches to the published sequence. Katsanis N, et al (Hum Genet 1997 September; 100(34):477480) utilized information generated by various EST sequencing projects to enrich the transcription map of chromosome 21 and report the mapping of SH3P17 to 21q22.1 and the localisation of two genes previously mapped to HSA21 by Nagase and colleagues, KIAA0136 and KIAA0179 to 21q22.2 and 21q22.3 respectively. Chen H, and Antonarakis SE (Cytogenet Cell Genet 1997;78(34):213–215) identified portions of genes on human chromosome 21 and mapped the gene to YACs and cosmids within 21q22.1—>q22.2 between DNA markers D21S319 and D21S65 using hybridization and PCR amplification. Lastly, Guipponi et. al. 1998, *Genomics* 53:369–376 reported that they identified two isoforms of the human homolog of *Xenopus* Intersectin (ITSN) produced from alternate transcripts, the first of which, a short transcript is reportedly ubiquitously expressed, while the second longer transcript is exclusively expressed in brain tissue. Later, Guipponi et. al. 1998 *Cytogenet Cell Genet.* 83:218–220 reported that they had identified the genomic structure, sequence and precise mapping of the human intersectin gene and speculated that it may play a role in the determination of certain of the phenotypic characteristics of Down syndrome. The authors did not present evidence and corresponding observations or speculation regarding the role of the discovered genes apart from a possible relation to Down syndrome, and as such, are distinguishable from the research and discoveries embodied in the present invention.

The present invention provides the complete nucleotide sequence of several SH3 genes, including the SH3D1A gene and clones thereof, their association with platelet dysfunction and leukemia, including a part of the increased risk of leukemia seen in Down Syndrome, and with dysfunctions associated with neural development and particularly development in the CNS.

SUMMARY OF THE INVENTION

In one embodiment, this invention provides isolated nucleic acids which encode human SH3 genes such as SH3D1A and cDNA clones thereof, including also analogs, fragments, variants, and mutants, thereof. This invention is directed to an isolated nucleic acid encoding an amino acid sequence which forms one or more myristoylation sites in the EH domain and SH3 domain. This invention provides an isolated nucleic acid encoding an amino acid sequence which forms one or more EH domains and one or more SH3 domains. In one embodiment the nucleic acid which encodes an amino acid sequence which forms two EH domains and four SH3 domains. As shown in FIG. 1 the nucleic acid encoding the amino acid sequence comprises one or more myristoylation sites in the EH domain and SH3 domain.

In one embodiment of this invention, the isolated nucleic acid encodes an amino acid sequence of the EH1 domain which is from amino acid sequence 15 to sequence 102. In another embodiment of this invention, the nucleic acid encodes an amino acid sequence of the EH2 domain which is from amino acid sequence 215 to sequence 310. In another embodiment of this invention, the nucleic acid encodes an amino acid sequence of the SH3-1 domain which is from amino acid sequence 740 to sequence 800. In another embodiment of this invention, the nucleic acid encodes an amino acid sequence of the SH3-2 domain which is from amino acid sequence 908 to sequence 966. In another embodiment of this invention, the nucleic acid encodes an amino acid sequence of the SH3-3 domain which is from amino acid sequence 999 to sequence 1062. In another embodiment of this invention, the nucleic acid encodes an amino acid sequence of the SH3-4 domain which is from amino acid sequence 1080 to sequence 1138. In another embodiment of this invention, the nucleic acid encodes an amino acid sequence of the SH3-1 domain which is from amino acid sequence 740 to sequence 800. In a preferred embodiment, the nucleic acid encodes an amino acid sequence as set forth in SEQ. ID. NO. 2, and as set forth in FIGS. 5, 9, 11, 13 and 15.

This invention provides for an isolated nucleic acid which encodes SH3D1A, and clones thereof as set forth herein. The isolated nucleic acid may be DNA or RNA, specifically cDNA or genomic DNA. This isolated nucleic acid also encodes mutant SH3D1A or the wildtype protein. The isolated nucleic acid may also encode a human SH3D1A having substantially the same amino acid sequence as the sequence designated FIG. 5. As used herein and in the claims, the terms nucleic acids encoding or expressing SH3D1A is intended to comprehend and include isolated nucleic acids that may have the sequence set forth in FIGS. 4, 8, 10, 12 or 14.

This invention is directed to a polypeptide comprising the amino acid sequence of a human SH3D1A or to a clone thereof. As used herein and in the claims, polypeptide or protein of SH3D1A is intended to comprehend and include polypeptides that comprise or otherwise correspond to those set forth in FIGS. 9, 11, 13, or 15 herein, or analogs or fragments thereof. Further, polyclonal and monoclonal antibodies which specifically bind to the polypeptide are disclosed and chimeric (bi-specific) antibodies are likewise contemplated.

This invention provides a method for determining whether a subject carries a mutation in the SH3D1A gene which comprises: (a) obtaining an appropriate nucleic acid sample from the subject; and (b) determining whether the nucleic acid sample from step (a) is, or is derived from, a nucleic acid which encodes mutant SH3D1A so as to thereby determine whether a subject carries a mutation in the SH3D1A gene.

This invention provides a method for determining whether a subject has a megakaryocytic abnormality, myeloproliferative disorder, platelet disorder, or leukemia, or a neural disorder which comprises: (a) obtaining an appropriate sample from the subject; and (b) contacting the sample with the antibody so as to thereby determine whether a subject has the megakaryocytic abnormality, myeloproliferative disorder, platelet disorder, leukemia or neural disorder.

This invention provides a method for determining whether a subject has a predisposition for a megakaryocytic abnormality, myeloproliferative disorder, platelet disorder, leukemia, or a neural disorder, which comprises: (a) obtaining an appropriate nucleic acid sample from the subject; and (b) determining whether the nucleic acid sample from step (a) is, or is derived from, a nucleic acid which encodes SH3D1A so as to thereby determine whether a subject has a predisposition for a megakaryocytic abnormality, myeloproliferative disorder, platelet disorder or leukemia, or a neural disorder.

This invention provides a method for determining whether a subject has a megakaryocytic abnormality, myeloproliferative disorder, platelet disorder, leukemia, or a neural disorder, which comprises: (a) obtaining an appropriate nucleic acid sample from the subject; and (b) determining whether the nucleic acid sample from step (a) is, or is derived from, a nucleic acid which encodes the human SH3D1A so as to thereby determine whether a subject has megakaryocytic abnormality, myeloproliferative disorder, platelet disorder, leukemia, or a neural disorder.

This invention provides a method for screening a tumor sample from a human subject for a somatic alteration in a SH3D1A gene in said tumor which comprises gene comparing a first sequence selected form the group consisting of a SH3D1A gene from said tumor sample, SH3D1A RNA from said tumor sample and SH3D1A cDNA made from mRNA from said tumor sample with a second sequence selected from the group consisting of SH3D1A gene from a nontumor sample of said subject, SH3D1A RNA from said nontumor sample and SH3D1A cDNA made from mRNA from said nontumor sample, wherein a difference in the sequence of the SH3D1A gene, SH3D1A RNA or SH3D1A cDNA from said tumor sample from the sequence of the SH3D1A gene, SH3D1A RNA or SH3D1A cDNA from said nontumor sample indicates a somatic alteration in the SH3D1A gene in said tumor sample.

This invention provides a method for monitoring the progress and adequacy of treatment in a subject who has received treatment for a megakaryocytic abnormality, myeloproliferative disorder, platelet disorder, leukemia or an abnormal neural condition which comprises monitoring the level of nucleic acid encoding the human SH3D1A at various stages of treatment.

The present invention provides the means necessary for production of gene-based therapies directed at cancer cells; diagnosis of the predisposition to, and diagnosis and treatment of megakaryocytic abnormality, hematopoietic disorders, myeloproliferative disorder, platelet disorder, Down Syndrome, leukemia, other disorders based in whole or in part from neural abnormalities or dysfunctions; and prenatal diagnosis and treatment of tumors. These therapeutic agents may take the form of polynucleotides comprising all or a portion of the SH3D1A gene placed in appropriate vectors or delivered to target cells in more direct ways such that the function of the SH3D1A protein is reconstituted. Therapeutic agents may also take the form of polypeptides based on either a portion of, or the entire protein sequence of SH3D1A.

This invention provides a pharmaceutical composition comprising an amount of the polypeptide of the human SH3D1A as defined herein, and a pharmaceutically effective carrier or diluent.

This invention provides a method of treating a subject having megakaryocytic abnormality, myeloproliferative disorder, platelet disorder, leukemia or neural abnormality or dysfunction, which comprises introducing the isolated nucleic acid into the subject under conditions such that the nucleic acid expresses SH3D1A, so as to thereby treat the subject.

This invention provides a method of treating a subject having megakaryocytic abnormality, myeloproliferative disorder, platelet disorder, leukemia, or neural abnormality or dysfunction, which comprises administration to the subject a therapeutically effective amount of the pharmaceutical composition to the subject.

Lastly, the present invention also provides kits for detecting in an analyte at least one oligonucleotide comprising the SH3D1A gene, or a portion thereof, the kits comprising polynucleotide complementary to the SH3D1A gene, a fragment, binding partner, analog or other portion thereof, gene packaged in a suitable container, and instructions for its use.

BRIEF DESCRIPTION OF THE DRAWINGS

FIG. 4. Nucleic acid sequence of human SH3D1A (SEQ ID NO:1).

FIG. 5. Amino acid sequence of human SH3D1A (SEQ ID NO:2).

FIG. 8. Nucleic acid sequence of cDNA clone also identified herein as Clone #21 (SEQ ID NO:3).

FIG. 9: Amino acid sequence of Clone #21. Upper part of Figure presents translated protein sequence (SEQ ID NO:4); lower portion of Figure presents whole protein sequence.

FIG. 10: Nucleic acid sequence of cDNA clone also identified herein as Clone #11 (SEQ ID NO:39).

FIG. 11: Amino acid sequence of Clone #11. Upper part of Figure presents translated protein sequence (SEQ ID NO:40); lower portion of Figure presents a whole protein sequence.

FIG. 12: Nucleic acid sequence of cDNA clone also identified herein as Clone #5 (SEQ ID NO:71).

FIG. 13: Amino acid sequence of Clone #5. Upper part of Figure presents translated protein sequence (SEQ ID NO:72); lower portion of Figure presents whole protein sequence.

FIG. 14: Nucleic acid sequence of cDNA clone also identified herein as Clone #9 (SEQ ID NO:76).

FIG. 15: Amino acid sequence of Clone #9. Upper part of Figure presents translated protein sequence (SEQ ID NO:77); lower portion of Figure presents whole protein sequence.

DETAILED DESCRIPTION OF THE INVENTION

The present invention discloses a family of SH3 genes, and particularly, a novel SH3D1A gene, and clones, and corresponding proteins, both translated and full length, which SH3D1A gene is on chromosome 21, and that contributes to the development of platelets and the pathogenesis of leukemias, both in general and in particular those involving the megakaryocytic lineage. The invention provides methods useful for diagnosing and treating the following: acute leukemias, thrombocytopenia, megakaryocytic abnormality, hematopoetic disorders, myeloproliferative disorder, platelet disorder, leukemia, leukemia in Down syndrome, leaukemia, platelet disorder on chromosome 21, low platelets in deletion for 21, association of gains in chromosome 21 with leukemias and disorders associated with associated with megakaryocytic dysfunction; and neural abnormalities, dysfunctions and disorders, including brain malformations and corresponding cognitive dysfunctions, microcephaly, lissencephaly, colpocephaly, holoprosencephaly.

Figure 1:
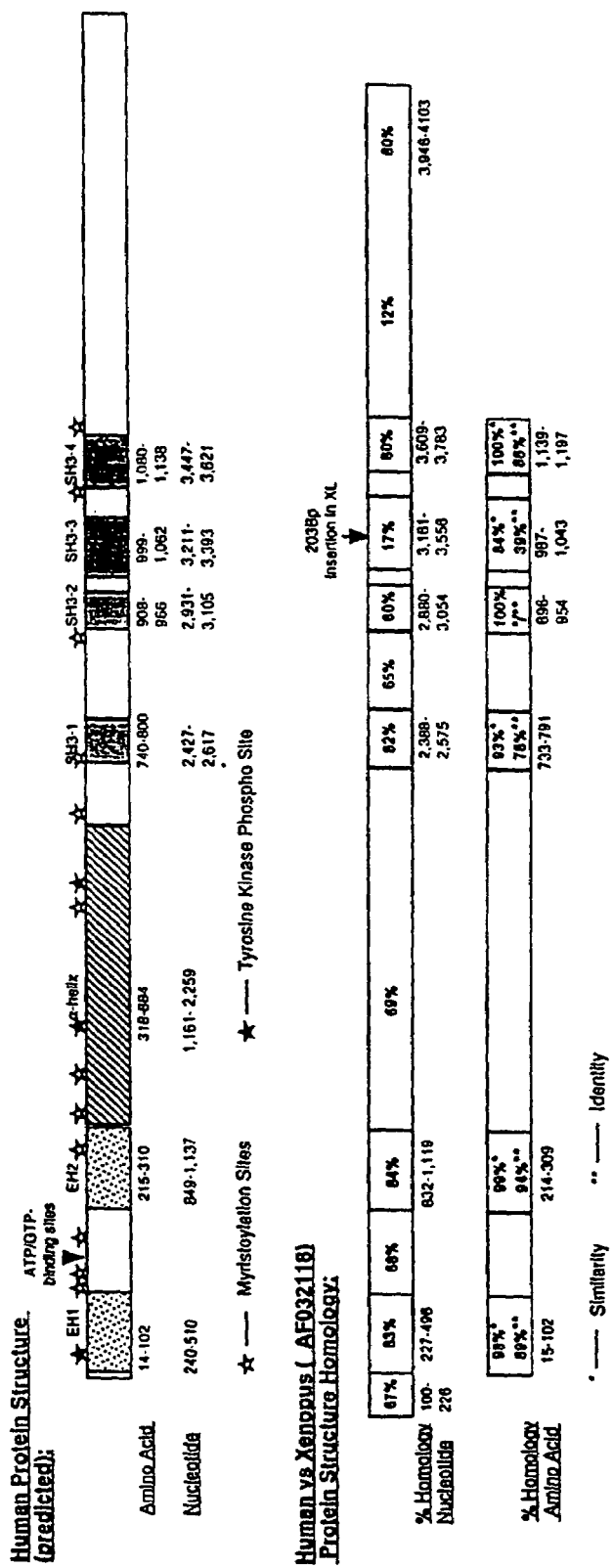
FIG. 1. Human SH3D1A structure and homology

This invention provides an isolated nucleic acid which encodes a human SH3D1A, as defined hereinabove, including analogs, such as the nucleic acids set forth in FIGS. 8, 10, 12 and 14, fragments, presented herein by way of non-limiting example, variants, and mutants, thereof. In one embodiment the nucleic acid has a nucleotide sequence having at least 85% similarity with the nucleic acid coding sequence of SEQ ID NO: 1. This invention is directed to an isolated nucleic acid encoding an amino acid sequence which forms one or more myristoylation sites in the EH domain and SH3 domain. This invention provides a isolated nucleic acid encoding an amino acid sequence which forms one or more EH domains and one or more SH3 domains. In one embodiment the nucleic acid which encodes an amino acid sequence which forms two EH domains and four SH3 domains. As show in FIG. 1 the nucleic acid encoding the amino acid sequence comprising one or more myristoylation sites in the EH domain and SH3 domain.

In one embodiment of this invention, the isolated nucleic acid encodes an amino acid sequence of the EH1 domain which corresponds to the following regions: amino acid sequence 15 to sequence 102. In another embodiment of this invention, the nucleic acid encodes an amino acid sequence of the EH2 domain which is from amino acid sequence 215 to sequence 310. In another embodiment of this invention, the nucleic acid encodes an amino acid sequence of the SH3-1 domain which is from amino acid sequence 740 to sequence 800. In another embodiment of this invention, the nucleic acid encodes an amino acid sequence of the SH3-2 domain which is from amino acid sequence 908 to sequence 966. In another embodiment of this invention, the nucleic acid encodes an amino acid sequence of the SH3-3 domain which is from amino acid sequence 999 to sequence 1062. In another embodiment of this invention, the nucleic acid encodes an amino acid sequence of the SH3-4 domain which is from amino acid sequence 1080 to sequence 1138. In another embodiment of this invention, the nucleic acid encodes an amino acid sequence of the SH3-1 domain which is from amino acid sequence 740 to sequence 800. In a preferred embodiment, the nucleic acid encodes an amino acid sequence as set forth in FIG. 5, or the corresponding analogs set forth in FIGS. 9, 11, 13 and 15, presented herein by way of non-limiting example. This invention contemplates nucleic acid or amino acid sequences which correspond to the SH3D1A gene, analogs, fragments, variants, mutants thereof. The corresponding nucleic acids or amino acids may be based on nucleic acid, or amino acid sequence as disclosed herein; or based on the structurally or functionally of the EH and SH3 domains which define the SH3D1A gene.

This invention provides for an isolated nucleic acid which encodes SH3D1A. This isolated nucleic acid may be DNA or RNA, specifically cDNA or genomic DNA. This isolated nucleic acid also encodes mutant SH3D1A or the wildtype protein. The isolated nucleic acid may also encode a human SH3D1A having substantially the same amino acid sequence as the sequence designated FIG. 5. Specifically the isolated nucleic acid has the sequence designated FIG. 4.

This invention provides for a replicable vector comprising the isolated nucleic acid molecule of the DNA virus. The vector includes, but is not limited to: a plasmid, cosmid, λ phage or yeast artificial chromosome (YAC) which contains at least a portion of the isolated nucleic acid molecule. As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

This invention provides a host cell containing the above vector. The host cell may contain the isolated DNA molecule artificially introduced into the host cell. The host cell may be a eukaryotic or bacterial cell (such as *E. coli*), yeast cells, fungal cells, insect cells and animal cells. Suitable animal cells include, but are not limited to Vero cells, HeLa cells, Cos cells, CV1 cells and various primary mammalian cells.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J Mol. Biol.* 48:443, by the search for similarity method of Pearson and Lipman (1988) *Proc. Natl. Acad. Sci. (USA)* 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

"Substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

This invention provides a nucleic acid having a sequence complementary to the sequence of the isolated nucleic acid of the human SH3D1A gene. Specifically, this invention provides an oligonucleotide of at least 15 nucleotides capable of specifically hybridizing with a sequence of nucleotides present within a nucleic acid which encodes the human SH3D1A. In one embodiment the nucleic acid is DNA or RNA. In another embodiment the oligonucleotide is labeled with a detectable marker. In another embodiment the oligonucleotide is a radioactive isotope, a fluorophor or an enzyme.

Oligonucleotides which are complementary may be obtained as follows: The polymerase chain reaction is then carried out using the two primers. See *PCR Protocols: A Guide to Methods and Applications* [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to the solid phase phosphoramidite triester method first described by Beaucage and Carruthers [19] using an automated synthesizer, as described in Needham-VanDevanter [69]. Purification of oligonucleotides is by either native acrylamide gel electrophoresis or by anion-exchange HPLC as described in Pearson, J. D. and Regnier, F. E. [75A]. The sequence of the synthetic oligonucleotide can be verified using the chemical degradation method of Maxam, A. M. and Gilbert, W. [63].

High stringency hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, including the clonal varients set forth herein, such that any such sequence variation corresponds to the nucleic acid sequence of the pathogenic organism or disease marker to which the relevant sequence listing relates.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, [19], or by the triester method according to Matteucci, et al., [62], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

Also, this invention provides an antisense molecule capable of specifically hybridizing with the isolated nucleic acid of the human SH3D1A gene. This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. In the cell, they hybridize to that mRNA, forming a double stranded molecule. The cell does not translate an mRNA in this double-stranded form. Therefore, antisense nucleic acids interfere with the expression of mRNA into protein.

Antisense nucleotides or polynucleotide sequences are useful in preventing or diminishing the expression of the SH3D1A gene, as will be appreciated by those skilled in the art. For example, polynucleotide vectors containing all or a portion of the SH3D1A gene or other sequences from the SH3D1A region (particularly those flanking the SH3D1A gene) may be placed under the control of a promoter in an antisense orientation and introduced into a cell. Expression of such an antisense construct within a cell will interfere with SH3D1A transcription and/or translation and/or replication. Oligomers of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention also provides a method of producing a polypeptide encoded by isolated DNA molecule, which comprises growing the above host vector system under suitable conditions permitting production of the polypeptide and recovering the polypeptide so produced.

This invention provides a polypeptide comprising the amino acid sequence of a human SH3D1A. In one embodiment, the amino acid sequence is set forth in FIG. 5. Further, the isolated polypeptide encoded by the isolated DNA molecule may be linked to a second polypeptide encoded by a nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated DNA molecule. In one embodiment the antibody is a monoclonal antibody. In another embodiment the antibody is a polyclonal antibody. The antibody or DNA molecule may be labelled with a detectable marker including, but not limited to: a radioactive label, or a calorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}Co$, $^{59}Fe$, 90Y, 125I, 131I, and $^{186}Re$. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detected by a second antibody which may be linked to an enzyme, such as alkaline phosphatase or horseradish peroxidase. Other enzymes which may be employed are well known to one of ordinary skill in the art.

"Specifically binds to an antibody" or "specifically immunoreactive with", when referring to a protein or peptide, refers to a binding reaction which is determinative of the presence of the SH3D1A of the invention in the presence of a heterogeneous population of proteins and other biologics including viruses other than the SH3D1A. Thus, under designated immunoassay conditions, the specified antibodies bind to the SH3D1A antigens and do not bind in a significant amount to other antigens present in the sample. Specific binding to an antibody under such conditions may require an antibody that is selected for its specificity for a particular protein. For example, antibodies raised to the human SH3D1A immunogen described herein can be selected to obtain antibodies specifically immunoreactive with the SH3D1A proteins and not with other proteins. These antibodies recognize proteins homologous to the human SH3D1A protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane [32] for a description of immunoassay formats and conditions that can be used to determine specific immunoreactivity.

This invention provides a method to select specific regions on the polypeptide encoded by the isolated DNA molecule of the DNA virus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. Also as set forth earlier herein, chimeric (bi-specific) antibodies may be prepared by techniques well known in the art, and are likewise contemplated herein. Any and all of these antibodies are useful to detect the expression of polypeptide encoded by the isolated DNA molecule of the DNA virus in living animals, in humans, or in biological tissues or fluids isolated from animals or humans.

The antibodies may be detectably labeled, utilizing conventional labeling techniques well-known to the art. Thus, the antibodies may be radiolabeled using, for example, radioactive isotopes such as $^3H$, $125I$, $^{131}I$, and $^{35}S$. The antibodies may also be labeled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, aequorin, and fluorescent proteins such as green fluorescent protein (GFP). Once labeled, the antibody may be employed to identify and quantify immunologic counterparts (antibody or antigenic polypeptide) utilizing techniques well-known to the art.

A description of a radioimmunoassay (RIA) may be found in Laboratory Techniques in Biochemistry and Molecular Biology [52], with particular reference to the chapter entitled "An Introduction to Radioimmune Assay and Related Techniques" by Chard, T., incorporated by reference herein. A description of general immunometric assays of various types can be found in the following U.S. Pat. No. 4,376,110 (David et al.) or U.S. Pat. No. 4,098,876 (Piasio).

One can use immunoassays to detect for the SH3D1A gene, specific peptides, or for antibodies to the virus or peptides. A general overview of the applicable technology is in Harlow and Lane [32], incorporated by reference herein.

In one embodiment, antibodies to the human SH3D1A can be used to detect the agent in the sample. In brief, to produce antibodies to the agent or peptides, the sequence being targeted is expressed in transfected cells, preferably bacterial cells, and purified. The product is injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane [32] at pages 567–573 and 584–589.

In a further embodiment of this invention, commercial test kits suitable for use by a medical specialist may be prepared to determine the presence or absence of predetermined binding activity or predetermined binding activity capability to suspected target cells. In accordance with the testing techniques discussed above, one class of such kits will contain at least the labeled polypeptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell (see, Kohler and Milstein [50], incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies. See for example: McCafferty, J et al. [64]; Hoogenboom, H. R. et al. [39]; and Marks, J. D. et al. [60].

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selection of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in *E. coli* is also useful. Examples of such markers include genes specifying resistance to antibiotics. See [81] supra, for details concerning selection markers and promoters for use in *E. coli*. Suitable eukaryote hosts may include plant cells, insect cells, mammalian cells, yeast, and filamentous fungi.

The peptides derived form the nucleic acids, peptide fragments are produced by recombinant technology may be purified by standard techniques well known to those of skill in the art. Recombinantly produced sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods, and others. See, for instance, Scopes, R. [84], incorporated herein by reference.

This invention is directed to analogs of the isolated nucleic acid and polypeptide which comprise the amino acid sequence as set forth above. The analog may have an N-terminal methionine or an N-terminal polyhistidine optionally attached to the N or COOH terminus of the polypeptide which comprise the amino acid sequence.

In another embodiment, this invention contemplates peptide fragments of the polypeptide which result from proteolytic digestion products of the polypeptide. In another embodiment, the derivative of the polypeptide has one or more chemical moieties attached thereto. In another embodiment the chemical moiety is a water soluble polymer. In another embodiment the chemical moiety is polyethylene glycol. In another embodiment the chemical moiety is mon-, di-, tri- or tetrapegylated. In another embodiment the chemical moiety is N-terminal monopegylated.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicty and antigenicity of heterologous compounds. For example, a PEG adduct of a human protein might be useful for the treatment of disease in other mammalian species without the risk of triggering a severe immune response. The compound of the present invention may be delivered in a microencapsulation device so as to reduce or prevent an host immune response against the compound or against cells which may produce the compound. The compound of the present invention may also be delivered microencapsulated in a membrane, such as a liposome.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment, the amino acid residues of the polypeptide described herein are preferred to be in the "L" isomeric form. In another embodiment, the residues in the "D" isomeric form can be substituted for any L-amino acid residue, as long as the desired functional property of lectin activity is retained by the polypeptide. $NH_2$ refers to the free amino group present at the amino terminus of a polypeptide. COOH refers to the free carboxy group present at the carboxy terminus of a polypeptide. Abbreviations used herein are in keeping with standard polypeptide nomenclature, *J. Biol. Chem.*, 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino-acid residue sequence indicates a peptide bond to a further sequence of one or more amino acid residues.

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Thus, polypeptide of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as γ-carboxylglutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110: 5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Mutations can be made in a nucleic acid encoding the polypeptide such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Synthetic DNA sequences allow convenient construction of genes which will express analogs or "muteins". A general method for site-specific incorporation of unnatural amino acids into proteins is described in Noren, et al. *Science,* 244:182–188 (April 1989). This method may be used to create analogs with unnatural amino acids.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutatamate, there will remain enough non-pyroglutamate peptide on the bead for sequencing. One of ordinary skill in would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

Chemical Moieties For Derivatization. Chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20:1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the—terminal amino acid residues; those having a free carboxyl group include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

This invention provides a method for determining whether a subject carries a mutation in the SH3D1A gene which comprises: a) obtaining an appropriate nucleic acid sample from the subject; and (b) determining whether the nucleic acid sample from step (a) is, or is derived from, a nucleic acid which encodes mutant SH3D1A so as to thereby determine whether a subject carries a mutation in the SH3D1A gene. In one embodiment, the nucleic acid sample in step (a) comprises mRNA corresponding to the transcript of DNA encoding a mutant SH3D1A, and wherein the determining of step (b) comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant SH3D1A. In another embodiment, the determining of step (b) comprises: i) contacting the nucleic acid sample of step (a), and the isolated nucleic acid with restriction enzymes under conditions permitting the digestion of the nucleic acid sample, and the isolated nucleic acid into distinct, distinguishable pieces of nucleic acid; (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant SH3D1A.

The present invention further provides methods of preparing a polynucleotide comprising polymerizing nucleotides to yield a sequence comprised of at least eight consecutive nucleotides of the SH3D1A gene; and methods of preparing a polypeptide comprising polymerizing amino acids to yield a sequence comprising at least five amino acids encoded within the SH3D1A gene.

The present invention further provides methods of screening the SH3D1A gene to identify mutations. Such methods may further comprise the step of amplifying a portion of the SH3D1A gene, and may further include a step of providing a set of polynucleotides which are primers for amplification of said portion of the SH3D1A gene. The method is useful for identifying mutations for use in either diagnosis of the predisposition to, and diagnosis and treatment of megakaryocytic abnormality, hematopoietic disorders, myeloproliferative disorder, platelet disorder, leukemia; neural abnormality or other disorder; and prenatal diagnosis and treatment of tumors. Useful diagnostic techniques include, but are not limited to fluorescent in situ hybridization (FISH), direct DNA sequencing, PFGE analysis, Southern blot analysis, single stranded conformation analysis (SSCA), Rnase protection assay, allele-specific oligonucleotide (ASO), dot blot analysis and PCR-SSCP, as discussed in detail further below.

There are several methods that can be used to detect DNA sequence variation. Direct DNA sequencing, either manual sequencing or automated fluorescent sequencing can detect sequence variation. For a gene as large as SH3D1A, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of tumors. Southern blots displaying hybridizing fragments (differing in length from control DNA when probed with sequences near or including the SH3D1A gene) indicate a possible mutation. If restriction enzymes which produce very large restriction fragments are used, then pulsed field gel electrophoresis (PFGE) is employed.

Detection of point mutations may be accomplished by molecular cloning of the SH3D1A allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined. There are six well known methods for a more complete, yet still indirect, test for confirming the presence of a susceptibility allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Rano & Kidd, 1989). For allele-specific PCR, primers are used which hybridize at their 3' ends to a particular SH3D1A mutation. If the particular SH3D1A mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the SH3D1A mutation found in that individual. Other techniques for detecting insertions and deletions as known in the art can be used.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the SH3D1A gene can also be detected using Southern hybridization, especially if the changes are gross rearrangements, such as deletions and insertions.

DNA sequences of the SH3D1A gene which have been amplified by use of PCR may also be screened using allele-specific probes. These probes are nucleic acid oligomers, each of which contains a region of the SH3D1A gene sequence harboring a known mutation. For example, one oligomer may be about 30 nucleotides in length, corresponding to a portion of the SH3D1A gene sequence. By use of a battery of such allele-specific probes, PCR amplification products can be screened to identify the presence of a previously identified mutation in the SH3D1A gene. Hybridization of allele-specific probes with amplified SH3D1A sequences can be performed, for example, on a nylon filter. Hybridization to a particular probe under stringent hybridization conditions indicates the presence of the same mutation in the tumor tissue as in the allele-specific probe.

Alteration of SH3D1A mRNA expression can be detected by any techniques known in the art. These include Northern blot analysis, PCR amplification and RNase protection. Diminished mRNA expression indicates an alteration of the wild-type SH3D1A gene. Alteration of wild-type SH3D1A genes can also be detected by screening for alteration of wild-type SH3D1A protein. For example, monoclonal antibodies immunoreactive with SH3D1A can be used to screen a tissue. Lack of cognate antigen would indicate a SH3D1A mutation. Antibodies specific for products of mutant alleles could also be used to detect mutant SH3D1A gene product. Such immunological assays can be done in any convenient formats known in the art. These include Western blots, immunohistochemical assays and ELISA assays. Any means for detecting an altered SH3D1A protein can be used to detect alteration of wild-type SH3D1A genes. Functional assays, such as protein binding determinations, can be used. In addition, assays can be used which detect SH3D1A biochemical function. Finding a mutant SH3D1A gene product indicates alteration of a wild-type SH3D1A gene. Mutant SH3D1A genes or gene products can also be detected in other human body samples, such as serum, stool, urine and sputum.

The present invention also provides for fusion polypeptides, comprising SH3D1A polypeptides and fragments. Homologous polypeptides may be fusions between two or more SH3D1A polypeptide sequences or between the sequences of SH3D1A and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor. See, e.g., Godowski et al., 1988. Fusion proteins will typically be made by either recombinant nucleic acid methods, as described below, or may be chemically synthesized. Techniques for the synthesis of polypeptides are described, for example, in Merrifield, 1963.

This invention provides a method for determining whether a subject has a megakaryocytic abnormality, myeloproliferative disorder, platelet disorder, or leukemia which comprises: (a) obtaining an appropriate sample from the subject; and (b) contacting the sample with the antibody so as to thereby determine whether a subject has the megakaryocytic abnormality, myeloproliferative disorder, platelet disorder, or leukemia.

This invention provides a method for determining whether a subject has a predisposition for a megakaryocytic abnormality, myeloproliferative disorder, platelet disorder, leukemia or a neural abnormality or other disorder, which comprises: (a) obtaining an appropriate nucleic acid sample from the subject; and (b) determining whether the nucleic acid sample from step (a) is, or is derived from, a nucleic acid which encodes SH3D1A so as to thereby determine whether a subject has a predisposition for a megakaryocytic abnormality, myeloproliferative disorder, platelet disorder, or leukemia.

This invention provides a method for determining whether a subject has a megakaryocytic abnormality, myeloproliferative disorder, platelet disorder, leukemia or a neural abnormality or other disorder, which comprises: (a) obtaining an appropriate nucleic acid sample from the subject; and (b) determining whether the nucleic acid sample from step (a) is, or is derived from, a nucleic acid which encodes the human SH3D1A so as to thereby determine whether a subject has megakaryocytic abnormality, myeloproliferative disorder, platelet disorder, leukemia or a neural abnormality or other disorder. In one embodiment the nucleic acid sample in step (a) comprises mRNA corresponding to the transcript of DNA encoding a human SH3D1A, and wherein the determining of step (b) comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes a human SH3D1A. A particular finding in accordance with the invention, is that such disorders as may occur in adult brain have been observed with respect to the present invention, and accordingly adult patients may be diagnosed, and if possible, treated by the application of the inventive subject matter hereof.

This invention provides a method of suppressing cells unable to regulate themselves which comprises introducing a purified human SH3D1A into the cells in an amount effective to suppress the cells.

This invention provides a method for identifying a chemical compound which is capable of suppressing cells unable to regulate themselves in a subject which comprises: (a) contacting the SH3D1A with a chemical compound under conditions permitting binding between the SH3D1A and the chemical compound; (b) detecting specific binding of the chemical compound to the SH3D1A; and (c) determining whether the chemical compound inhibits the SH3D1A so as to identify a chemical compound which is capable of suppressing cells unable to regulate themselves.

This invention provides a method for screening a tumor sample from a human subject for a somatic alteration in a SH3D1A gene in said tumor which comprises gene comparing a first sequence selected form the group consisting of a SH3D1A gene from said tumor sample, SH3D1A RNA from said tumor sample and SH3D1A cDNA made from mRNA from said tumor sample with a second sequence selected from the group consisting of SH3D1A gene from a nontumor sample of said subject, SH3D1A RNA from said nontumor sample and SH3D1A cDNA made from mRNA from said nontumor sample, wherein a difference in the sequence of the SH3D1A gene, SH3D1A RNA or SH3D1A cDNA from said tumor sample from the sequence of the SH3D1A gene, SH3D1A RNA or SH3D1A cDNA from said nontumor sample indicates a somatic alteration in the SH3D1A gene in said tumor sample.

This invention provides a method for screening a tumor sample from a human subject for the presence of a somatic alteration in a SH3D1A gene in said tumor which comprises comparing SH3D1A polypeptide from said tumor sample from said subject to SH3D1A polypeptide from a nontumor sample from said subject to analyze for a difference between the polypeptides, wherein said comparing is performed by (i) detecting either a full length polypeptide or a truncated polypeptide in each sample or (ii) contacting an antibody which specifically binds to either an epitope of an altered SH3D1A polypeptide or an epitope of a wild-type SH3D1A polypeptide to the SH3D1A polypeptide from each sample and detecting antibody binding, wherein a difference between the SH3D1A polypeptide from said tumor sample from the SH3D1A polypeptide from said nontumor sample indicates the presence of a somatic alteration in the SH3D1A gene in said tumor sample.

This invention provides a method for monitoring the progress and adequacy of treatment in a subject who has received treatment for a megakaryocytic abnormality, myeloproliferative disorder, platelet disorder, leukemia or a condition involving a neural abnormality or dysfunction, which comprises monitoring the level of nucleic acid encoding the human SH3D1A at various stages of treatment.

This invention provides a pharmaceutical composition comprising an amount of a polypeptide of the present invention, and a pharmaceutically effective carrier or diluent.

This invention provides a method of treating a subject having megakaryocytic abnormality, myeloproliferative disorder, platelet disorder, or leukemia which comprises introducing the isolated nucleic acid into the subject under conditions such that the nucleic acid expresses SH3D1A, so as to thereby treat the subject.

This invention provides a method of treating a subject having megakaryocytic abnormality, myeloproliferative disorder, platelet disorder, or leukemia which comprises administration to the subject a therapeutically effective amount of the pharmaceutical composition to the subject.

This invention is directed to diagnostic methods and therepeutic treatments relating to th e following: Wilms tumor, Li-Fraumcini syndrome, retinoblastoma, familiar colon cancer, and acute myelogenous leukemia (AML), and myelodysplastic syndromes (MDSs).

Further, it is contemplated by this invention that the disclosed invention is directed to diversified hereditary disorders of platelet production. Heredity disorders of platelet production include but is not limited to: clinical problems in these disorders range from mild cutaneous petechiae or occasional epistaxes to severe hemorrhage requiring red cell and platelet transfusions; and abnormalities of thrombocyte structure, function, and number have been found by laboratory evaluation of some of these patients. Deviations from normality in various components of the platelet response during hemostatis have been well characterized in a number of families and are known to those skilled in the art. These include defects of platelet adhesion, secretion from storage granules, and subsequent aggregation.

This invention provides a method of diagnosing megakaryocytic abnormality, myeloproliferative disorder, platelet disorder, or leukemia in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated DNA, under hybridizing conditions; and (c) determining the presence of the nucleic acid molecule hybridized, the presence of which is indicative of megakaryocytic abnormality, myeloproliferative disorder, platelet disorder, or leukemia in the subject, thereby diagnosing megakaryocytic abnormality, myeloproliferative disorder, platelet disorder, or leukemia in the subject.

In one embodiment the DNA molecule from the tumor lesion is amplified before step (b). In another embodiment PCR is employed to amplify the nucleic acid molecule. Methods of amplifying nucleic acid molecules are known to those skilled in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One example of such solid matrix is nitrocellulose paper.

This invention provides a method of diagnosing megakaryocytic abnormality, myeloproliferative disorder, platelet disorder, leukemia or a neural abnormality or dysfunction, in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated DNA, under hybridizing conditions; and (c) determining the presence of the nucleic acid molecule hybridized, the presence of which is indicative of megakaryocytic abnormality, myeloproliferative disorder, platelet disorder, leukemia or neural abnormality or dysfunction, in the subject, thereby diagnosing megakaryocytic abnormality, myeloproliferative disorder, platelet disorder, or leukemia in the subject.

This invention provides a method of diagnosing a DNA virus in a subject, which comprises (a) obtaining a suitable bodily fluid sample from the subject, (b) contacting the suitable bodily fluid of the subject to a support having already bound thereto a antibody, so as to bind the antibody to a specific antigen, (c) removing unbound bodily fluid from the support, and (d) determining the level of antibody bound by the antigen, thereby diagnosing the subject for megakaryocytic abnormality, myeloproliferative disorder, platelet disorder, leukemia or neural disorder.

This invention provides a method of diagnosing megakaryocytic abnormality, myeloproliferative disorder, platelet disorder, or leukemia in a subject, which comprises (a) obtaining a suitable bodily fluid sample from the subject, (b) contacting the suitable bodily fluid of the subject to a support having already bound thereto an antigen, so as to bind antigen to a specific antibody, (c) removing unbound bodily fluid from the support, and (d) determining the level of the antigen bound by the antibody, thereby diagnosing megakaryocytic abnormality, myeloproliferative disorder, platelet disorder, leukemia or neural disorder.

A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting.

The diagnostic assays of the invention can be nucleic acid assays such as nucleic acid hybridization assays and assays which detect amplification of specific nucleic acid to detect for a nucleic acid sequence of the human SH3D1A described herein.

Accepted means for conducting hybridization assays are known and general overviews of the technology can be had from a review of: *Nucleic Acid Hybridization: A Practical Approach [72]; Hybridization of Nucleic Acids Immobilized on Solid Supports [41]; Analytical Biochemistry [4]* and Innis et al., *PCR Protocols [74]*, supra, all of which are incorporated by reference herein.

Target specific probes may be used in the nucleic acid hybridization diagnostic. The probes are specific for or complementary to the target of interest. For precise allelic differentiations, the probes should be about 14 nucleotides long and preferably about 20–30 nucleotides. For more general detection of the human SH3D1A of the invention, nucleic acid probes are about 50 to about 1000 nucleotides, most preferably about 200 to about 400 nucleotides.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

An alternative means for determining the presence of the human SH3D1A is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in *Methods Enzymol. [67]* incorporated by reference herein. In an in situ hybridization, cells are fixed to a solid support, typically a glass slide. The cells are then contacted with a hybridization solution at a moderate temperature to permit annealing of target-specific probes that are labeled. The probes are preferably labelled with radio-isotopes or fluorescent reporters.

The above described probes are also useful for in-situ hybridization or in order to locate tissues which express this gene, or for other hybridization assays for the presence of this gene or its mRNA in various biological tissues. In-situ hybridization is a sensitive localization method which is not dependent on expression of antigens or native vs. denatured conditions.

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

used herein, "pharmaceutical composition" could mean therapeutically effective amounts of polypeptide products of the invention together with suitable diluents, preservatives, solubilizers, emulsifiers, adjuvant and/or carriers useful in SCF (stem cell factor) therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response.

Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 µg/kg to about 1000 mg/kg. The amount may be 10 mg/kg. The pharmaceutically acceptable form of the composition includes a pharmaceutically acceptable carrier.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host.

According to the invention, the component or components of a therapeutic composition of the invention may be introduced parenterally, transmucosally, e.g., orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer 1990, *Science* 249:1527–1533.

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

This invention is illustrated in the Experimental Details section which follows. These sections are set forth to aid in an understanding of the invention but are not intended to, and should not be construed to, limit in any way the invention as set forth in the claims which follow thereafter.

Experimental Details Section

The invention discloses a small candidate region of 50–200 kb for low platelets in deletion for chromosome 21. At present, the candidate region for the familial platelet disorder is greater than 3,000 kb, a region containing as many as 150 genes. The SH3D1A is mapped to the small candidate region for low platelets for chromosome 21. Northern analysis using new sequence from SH3D1A reveals an abnormal band with significantly higher expression in RNA from lymphoblastoid cells derived from an affected individual vs. normal controls. DNA sequence analyses reveal homologies to domains that suggest involvement in developmental and/or cell regulatory phenomena such as lead to cancers when disturbed. These include the SH3 domains as well as EH domains, both associated with protein—protein interactions and the latter associated with maintenance of the cytoskeleton. Therefore, mutations, or increased or decreased expression are ultimately responsible for familial platelet disorder and possibly also for DS leukemias, subsets of non-DS leukemias and the processes that ultimately lead to abnormal platelets associated with deletion of chromosome 21.

Materials and Methods

Genomic clone obtained by screening the BAC library with EST: In order to study the gene structure of SH3D1A, the genomic clones were obtained by screening a human BAC library B with a radio-labeled EST (cDNA) (dbEST#482496, Research Genetics, AL) according to the procedure described by Hurbet et al., 1997. Three positive clones were observed.

Fluorescence in situ hybridization (FISH) to confirm the cytogenetic location of BAC 119E16 on chromosomes 21q22,11–12: BAC DNAs were made as described in the previous publication (Hurbert et al., 1997). The BAC DNAs as probes were biotinylated and FISHed onto normal human chromosome preparations following the procedure described by Korenberg and Chen (1995). BAC 119E16 was confirmed to map on chromosome 21q22.11-12 by reviewing more than 50 cells. This was further confirmed as well by PCR using custom-designed primers for SH3D1A based on sequencing information.

Sequencing cDNA and part of the genomic DNA: The cDNA was sequenced using RT-PCR products templated on total brain cDNA or directly on BAC 119E 16 containing the gene.

Reverse transcription—polymerase chain reaction (RT-PCT): SH3D1A cDNA was amplified by RT-PCR using a standard method. Briefly, the control RNA was isolated from a normal male cell line using the TR1 reagent kit (Molecular Research Center, Inc. Cincinnati, Ohio). The first strand of cDNA was then produced using SuperScript Choice System (Pharmacia LKB Biotechnology). The PCR reaction was performed using custome designed primers with PCT-100 Programmable Thermal Controller by a standard PCR procedure. The PCR products for sequencing were prepared by purification with Geneclean Kit (BIO 101, Inc., Vista, Calif.) prior to sequencing. To produce clearer sequence, some PCR products were subcloned into pCR-2.1 Vector (CLONETECH Laboratory, Inc.) prior to sequencing.

PCR of genomic DNA: three genomic (exon) fragments were generated via PCR by using the BAC 119E16 DNA as template, and purified and sequenced as described above and below.

Sequencing SH3D1A:

The nucleotide sequence of both the coding and noncoding strands were determined in their entirety by the dideoxy chain termination methods using the ABI PRISM Sequences DNA sequencing kit (PERKIN ELMER) with custom-made primers. The template for DNA sequencing were either PCR products or subclones as described above.

Sequencing the upstream region of SH3D1A:

In order to complete sequencing of the 5' end of SH3D1A and identify the site of initiation of transcription, the following two methods were utilized:

1.5° RACE:

5' RACE was performed by using 5' Marathon RACE kit (CLONETECH Laboratories, Inc. CA). The reaction products were then electrophoresed onto 1% of SeaPlaque GTG agarose (FMC BioProducts, Rockland, Me.). The products with the longest srizes (>2 Kb) were then further confirmed by sequencing nested PCR fragments.

2. cDNA isolation from cDNA library:

The human cDNA clones were obtained from a cDNA library screening as described in Yamakama et al., (1995). The cDNAs were oligo (dT) primed and cloned undirectionally into the EcoRI and ChoI sites of the vector. The size of the clones were analyzed by electrophoresis and then using for sequencing.

Sequencing Analysis:

Data processing was performed using ABI Sequencing Analysis software which assessed trace quality and assembled sequence data (ABI-Autoassemble program). The vector clipping was performed manually. To ensure the accuracy of the sequence, all regions of the finished sequence was covered by more than one subclone or PCR fragments, usually 3–5× and always were sequenced in opposite orientations. The sequence of the human SH3D1A was screened against Genbank (BLASTN & BLASTX). It was also compared with the previously published SH3P17 sequence (Hsu61166) by using V-gcg program. Significant differences between the previously published SH3P17 and this newly sequenced SH3D1A were found. These equalled about 8% of the nucleotides. Previous sequence totalled only 3,230 bps of the 3' end vs. the subject invention's sequence of 5,200 bp. Comparison using with the complete homology sequence gb#AF032118 in *Xenopus Leavis* indicated the same protein start site and a similar but not identical domain structure, see FIGS. 1 and 2.

SH3D1A Gene Structure:

Protein structure was based on cNDA sequence analysis. The four SH3 domains were confirmed previously (Sparks et al., 1996). However, most significant was the definition of additional domains including EH domain (Eps Homolog domain) in the N terminal end that have been associated with protein interactions involved with cell cycle control and morphogenesis. These suggested a possible role, both in human embryogenesis and in cancers, notably the leukemias associated with Down Syndrome (DS), the decreased platelets associated with deletion of chromosome 21 reported by Fannin et al., 1995, and the familial platelet disorder reported by Dowton et al. (1985) and Ho et al. (1996), all of whose map positions include SH3P17.

Figure 6:
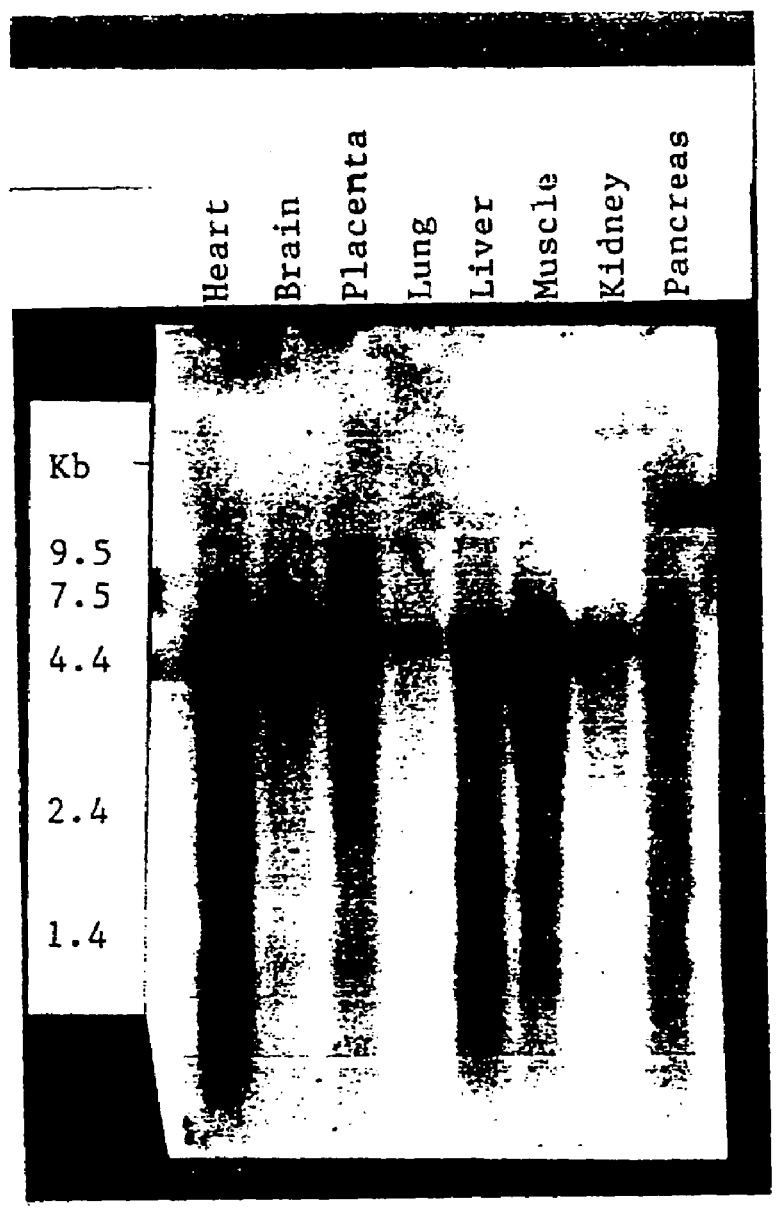
FIG. 6. Northern Blot of SH3D1A expressed in heart, brain, placenta, lung, liver, muscle, kidney and pancreas.
Figure 7:
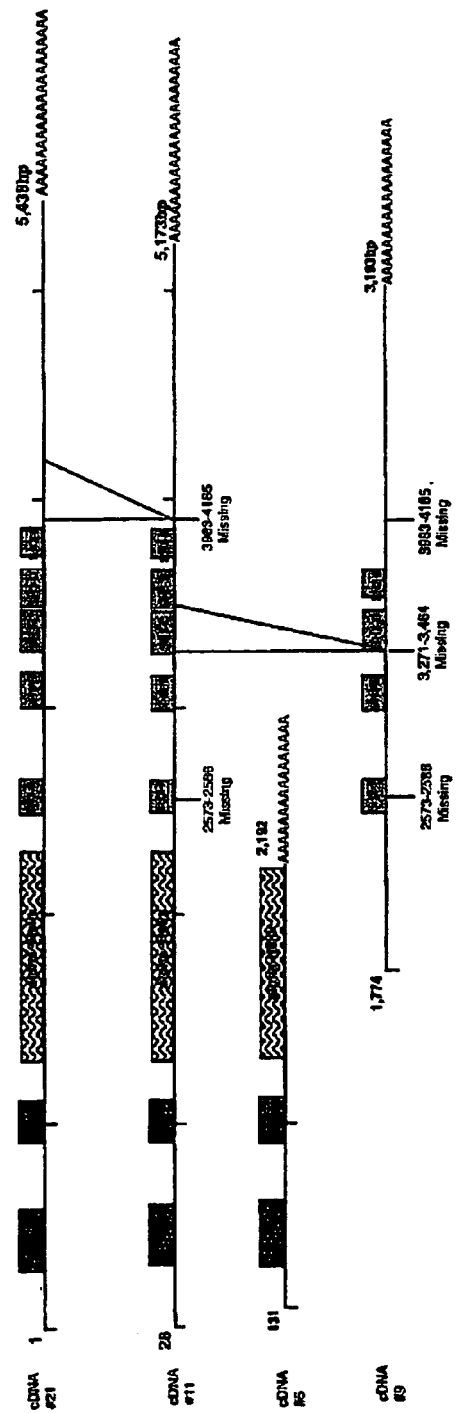
FIG. 7. Map presenting four cDNA clones in accordance with the invention, including length and protein domains.
Figure 16:
FIG. 16. Tissue immunochemical staining on mouse embryo (Day 9) showing ITSN expression in neural blasts during migration and formation in CNS.

Gene Expression Study by Northern Blotting:

Northern blots made from human multiple tissues were used to perform this study according to the manufacturer's instruction (CLONETHch Laboratory, Inc., CA). Referring to FIG. 6, the gene was found to be expressed in all adult human tissues tested, those included Heart, brain, placenta, lung, liver, muscle, kidney and pancreas.

Preparation of Full Length cDNA Clones Corresponding to SH3D1A

A cDNA library based on fetal brain was screened in the same manner as described above with respect to the isolation and sequencing of SH3D1A. Accordingly, Sequencing of 5 different sizes of the cDNA clones was conducted, and indicated that there are at least three isoforms that exist. As all of the sequenced cDNA clones shown in FIG. 8, #21 is a full-length cDNA that contains 5438 nucleotides and codes for 1221 amino acids; #11 was a shorter full-length cDNA that contains 5179 nucleotides and codes for 1215 amino acids; clone #s 5 and #9 represent 2192 bp, 3193 bp and 3128 bp length cDNA respectively, while #5 was identical to #21 and #11 at the 5' UTR containing only two EH domains.

Figure 3:
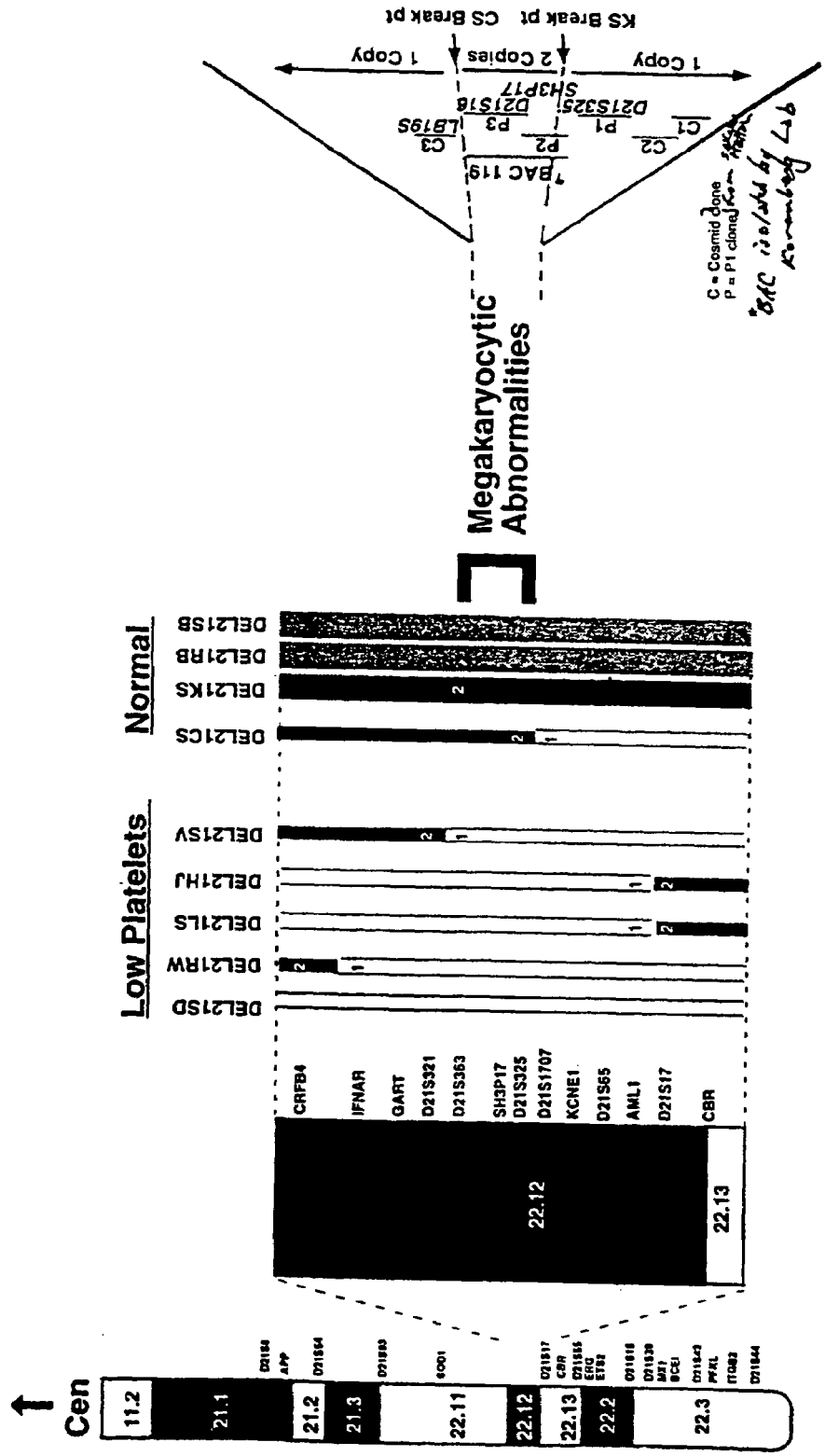
FIG. 3. Region of chromosome 21 responsible for megakaryocytic abnormalities.
Figure 18:
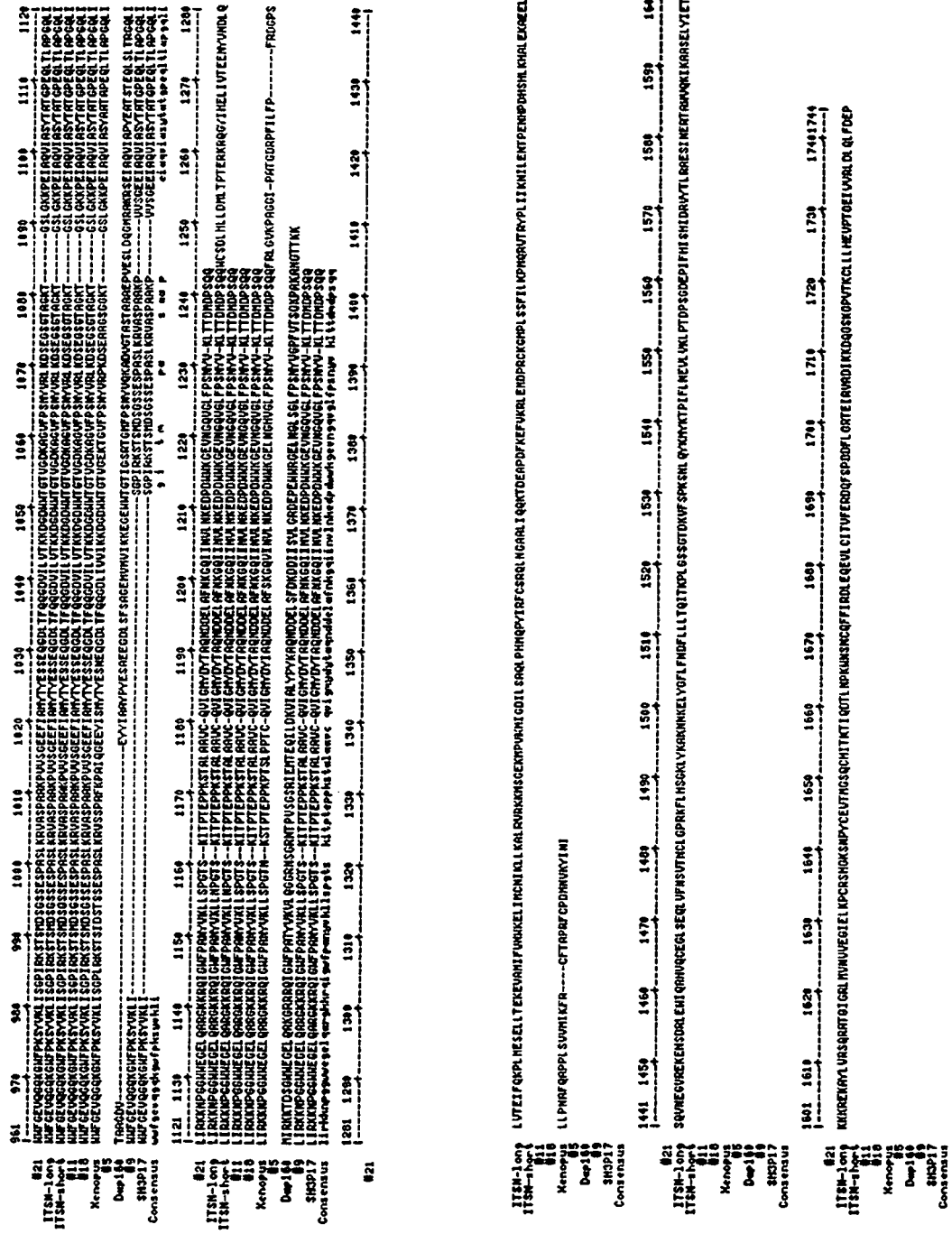
FIG. 18: Sequence comparisons between nucleic acid molecules of present invention, and Intersectins (ITSN), including a consensus sequence. "#21." SEQ ID NO: 4: "11," SEQ ID NO: 40; "#5," SEQ ID NO: 72; "#9," SEQ ID NO: 77.

The comparison between cDNAs generated in this study vs previously published homologous, or the comparison between each cDNAs islated in this study, we found significant differences as shown in FIG. 18. The differences between #21 vs ITSs, #21 vs #11 and #9 vs SH3P17 are listed here: #21 is 99.8% identical to ITSs (AF064243; Guipponi et al., 1998) at protein level showing only 1 amino acid different at the position of 114, while at the 5' UTR, the extra 160 bp and XXbp difference at the 3' UTR of #21 that gives a 96.7% identity at neuleotides level; #11 was missing 5 amino acids at the position of cDNA 2573–2586 within SH3-A domain and missing 222 neucliotides within 3' UTR region while comparing to #21; #9 was 100% identical to SH3P17 (GenBank Hsu61166, Sparks et al., 1996) at coding region, but it shows 76.8% identity at neucleotides level, the major difference is at the 3' UTR, that is a total of 222 bp is missing at the position of 2189 (3963–1774) to 2411 and presents at the same position as shown at #11 vs #21. #9 and SH3P 17 only showed four SH3 domains missing SH3—C domain (Guipponi et al., 1998) (FIG. 3).

Figure 2:
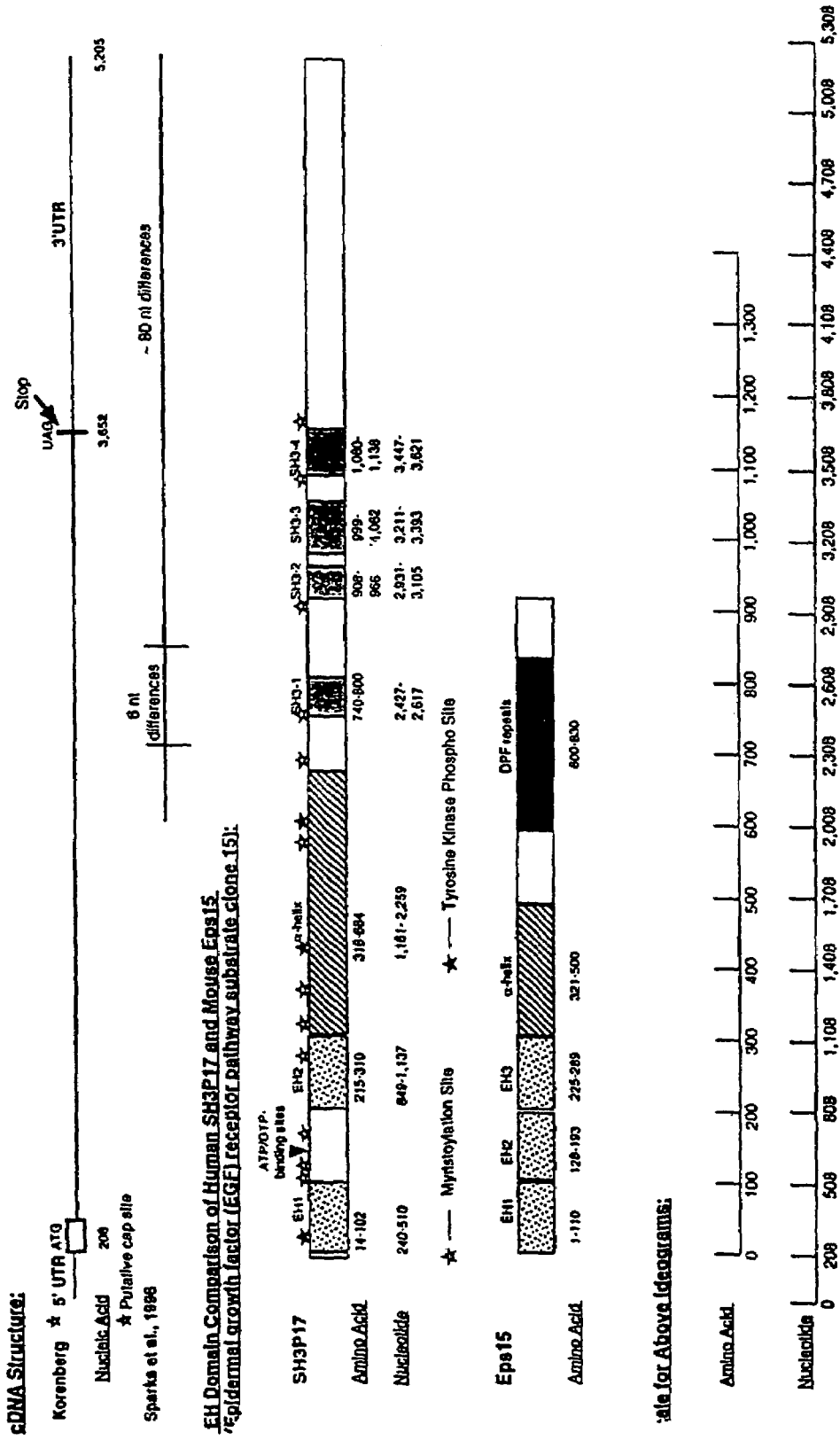
FIG. 2. SH3D1A domain structure and homologies—human vs. *Xenopus*

The homologies of ITSN to other proteins were also included in FIG. 2. (Sparks et al. 1996 and Guipponi et al. 1998) as discussed by Guipponi et al., 1998.

Genomic Organization of the ITSN Gene and Comparison to SH3P17 and ITSs/ITSI:

The comparison of the human SH3D1A to sequenced human genomic DNA (GenBank No AP000050, AP000049 and AP000048) in this region on chromosome 21 revealed that this gene consistes of 29 exons (FIG. 3 and Table 2 for exact exon-intron boundaries), the sizes of which vary from 44 to 1516 bp. The sizes of the introns range from 355 bp 7.5 Kb. All introns have splice donor and acceptor sites that confirm to the general GT-AG consensus motif. The putative SHD1A translation initiation codon is located on exon 2, while the stop codon is on exon 28.

Characterization of the 5' Upstream Sequence

To determine the 5' upstream sequence of the human SH3D1A gene, the sequence from PAC T1276 was used to carry out the analysis for searching the promoter(s).

Figure 17:
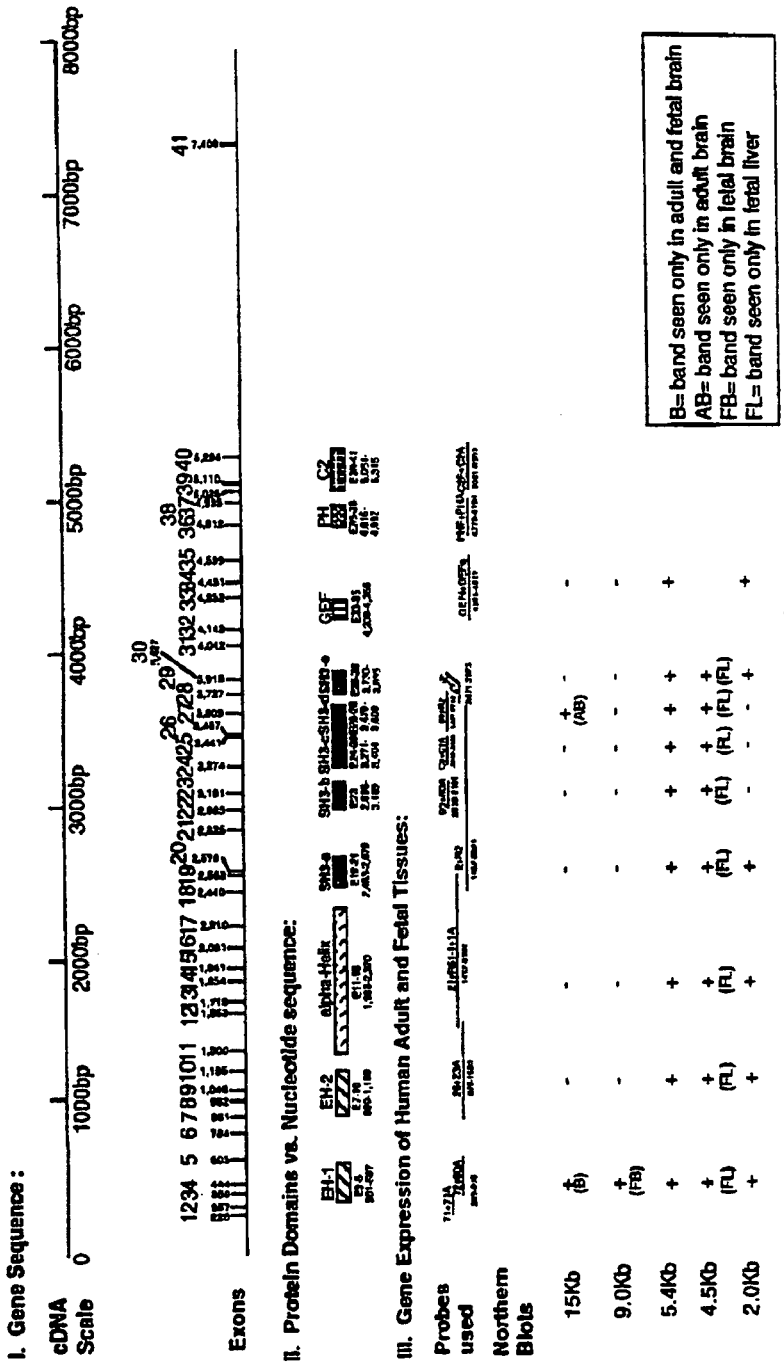
FIG. 17. Summary of Studies on ITSN:
  I. Gene sequence: First line showing the scale of ITSN cDNA; Second line showing the total numbers of the exons and the positions of each exon located.
  II. Protein domains vs nucleotide sequence: ITSN was predicted consists of 11 protein domains as listed on the map—2 EH domains, 5 SH3 domains and 1 of each GEF, pH and C2 domains. Their relative positions on the cDNA level were numbered under each domain.
  III. Gene expression of human adult and fetal tissues: This part summarized the Northern blot results showing ITSN was ubiquitously expressed with extensive alternative splicing generating tissue and developmental stage-specific expression.

Complex mRNA Expression on Multiple Adult and Fetal Tissues (See FIG. 17: Summary of Studies on ITS)

As shown in the table and figure, Northern blot of SH3D1A on mutiple adult and fetal tissues revealed unexpectedly complicated results. A total of 14 probes were used for expression study (Part 1). There were 6 major mRNA transcripts detected, including a 5.4 kb of mRNA fragment that was expressed ubiquitously (Heart, brain, placenta, lung, liver, muscle, kidney and pancreas) in adult and fetal tissues (brain, lung, liver and kidney) using any of the probes used as shown in the top portion of the Figure; a 2.5 kb fragment expressed in adult ubiquitously, but strong in muscle while using probe #1 (exon 1); a 2.0 kb fragment that was expressed ubiquitously in adult and fetal while using all of the probes except for probes #2, 3 and #12–13 (exon 2–7 and exon 28–29); the strongest expression were shown on muscle in adult and on liver and brain in fetal; a 4.5 kb fragment expressed ubiquitously, but stronger on liver, only seen in fetal while using probes #4, 6, 9 and 12 (exon 7 to 17 and exon 23–25; finally, a fragment larger than 11 kb that was expressed specifically on brain by using probes #2 and 3 (exons 2 to 7) in adult and fetal tissue, and only seen in adult by using probe #9 (exon 22–28). Further, there was a small fragment 1.0 kb also seen on liver in fetal tissue by using probes #4 and 6 (exon 7 to 17).

Results

The data presented herein confirm the role of the genes of the invention in conditions relating to leukemia as well as neural abnormalities and dysfunctions. As mentioned earlier, the genes are observed as to changes that occur in regions related to leukemia, and in relation to brain abnormalities observed with adult brain. The role of this family of genes in the regulation of both neural and leukemic conditions supports a broad modulatory influence on both development and homeostasis that commends their application in the diagnostic and therapeutic modalities presented herein.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references have been identified and referred to herein. The disclosures of such ted references as well as other publications, patent disclosures or documents recited herein, are all incorporated herein by reference in their entireties.

What is claimed is:

1. An isolated nucleic acid having the nucleotide sequence set forth in SEQ ID NO: 1.

2. The isolated nucleic acid of claim 1, wherein the nucleic acid is DNA or RNA.

3. The isolated nucleic acid of claim 1, wherein the nucleic acid is cDNA.

4. The isolated nucleic acid of claim 1, wherein the nucleic acid is labeled with a detectable marker.

5. The isolated nucleic acid of claim 4, wherein the detectable marker is a radioactive isotope, a fluorophor or an enzyme.

6. An isolated nucleic acid complementary to the entire sequence of the nucleic acid of claim 1.

7. The isolated nucleic acid of claim 6, wherein the isolated nucleic acid is labeled with a detectable marker.

8. The isolated nucleic acid of claim 7, wherein the marker is a radioactive isotope, a fluorophor or an enzyme.

9. A vector comprising the isolated nucleic acid of claim 1.

10. The vector of claim 9, further comprising a promoter or an expression element linked to the nucleic acid.

11. The vector of claim 9, wherein the promoter comprises a bacterial, yeast, insect or mammalian promoter.

12. The vector of claim 10, wherein the vector is a plasmid, cosmid, yeast artificial chromosome (YAC), BAC, P1, bacteriophage or eukaryotic viral DNA.

13. An isolated host cell containing the vector of claim 9.

14. The isolated host cell of claim 13, wherein the host cell is a prokaryotic or eukaryotic cell.

15. The isolated host cell of claim 14, wherein the eukaryotic cell is a yeast, insect, plant or mammalian cell.

16. A method for producing a polypeptide comprising culturing the host cell of claim 9 under conditions suitable for production of the polypeptide and recovering the polypeptide from the host cell culture.

17. A method of obtaining a polypeptide in purified form comprising:
   (a) introducing the vector of claim 9 into a suitable host cell;
   (b) culturing the resulting cell so as to produce the polypeptide;
   (c) recovering the polypeptide produced in step (b); and
   (d) purifying the polypeptide.

* * * * *

SEQUENCE LISTING

<160> NUMBER OF SEQ ID NOS: 109

<210> SEQ ID NO 1
<211> LENGTH: 5199
<212> TYPE: DNA
<213> ORGANISM: Homo sapiens

<400> SEQUENCE: 1

```
caaaagaatt ccgggtacgg cggctcgcga ggaagaatcc cgagcgggct ccgggacgga      60
cagagaggcg ggcggggatg gtgtgcgggg ctgcggctcc tgcgtccctc ccagcggcgc     120
gtgagcggca ctgatttgtc cctggggcgg cagcgcggac ccgcccggag atgaggcgtc     180
gattagcaag gtaaaagtaa cagaaccatg gctcagtttc caacacctt tggtggcagc     240 ctggatatct gggccataac tgtagaggaa agagcgaagc atgatcagca gttccatagt     300
ttaaagccaa tatctggatt cattactggt gatcaagcta gaaacttttt ttttcaatct     360
gggttacctc aacctgtttt agcacagata tgggcactag ctgacatgaa taatgatgga     420
agaatggatc aagtggagtt ttccatagct atgaaactta tcaaactgaa gctacaagga     480
tatcagctac cctctgcact tccccctgtc atgaaacagc aaccagttgc tatttctagc     540
gcaccagcat ttggtatggg aggtatcgcc agcatgccac cgcttacagc tgttgctcca     600
gtgccaatgg gatccattcc agttgttgga atgtctccaa ccctagtatc ttctgttccc     660
```

-continued

| | |
|---|---|
| acagcagctg tgccccccct ggctaacggg gctcccsctg ttatacaacc tctgcctgca | 720 |
| tttgctcatc ctgcagccac attgccaaag agttcttcct ttagtagatc tggtccaggg | 780 |
| tcacaactaa acactaaatt acaaaaggca cagtcatttg atgtggccag tgtcccacca | 840 |
| gtggcagagt gggctgttcc tcagtcatca agactgaaat acaggcaatt attcaatagt | 900 |
| catgacaaaa ctatgagtgg acacttaaca ggtccccaag caagaactat tcttatgcag | 960 |
| tcaagtttac cacaggctca gctggcttca atatggaatc tttctgacat tgatcaagat | 1020 |
| ggaaaactta cagcagagga atttatcctg caatgcacc tcattgatgt agctatgtct | 1080 |
| ggccaaccac tgccacctgt cctgcctcca aatacattc caccttcttt tagaagagtt | 1140 |
| cgatctggca gtggtatatc tgtcataagc tcaacatctg tagatcagag ctaccagag | 1200 |
| gaaccagttt tagaagatga acaacaacaa ttagaaaaga aattacctgt aacgtttgaa | 1260 |
| gataagaagc gggagaactt tgaacgtggc aacctggaac tggagaaacg aaggcaagct | 1320 |
| ctcctggaac agcagcgcaa ggagcaggag cgcctggccc agctggagcg ggcggagcag | 1380 |
| gagaggaagg agcgtgagcg ccaggagcaa gagcgcaaaa gacaactgga actggagaag | 1440 |
| caactggaaa agcagcggga gctagaacgg cagagagagg aggagaggag gaaagaaatt | 1500 |
| gagaggcgag aggctgcaaa acgggaactt gaaaggcaac gacaacttga gtgggaacgg | 1560 |
| aatcgaaggc aagaactact aaatcaaaga aacaaagaac aagaggacat agttgtactg | 1620 |
| aaagcaaaga aaaagacttt ggaatttgaa ttagaagctc taaatgataa aaagcatcaa | 1680 |
| ctagaaggga aacttcaaga tatcagatgt cgattgacca cccaaaggca agaaattgag | 1740 |
| agcacaaaca aatctagaga gttgagaatt gccgaaatca cccatctaca gcaacaatta | 1800 |
| caggaatctc agcaaatgct tggaagactt attccagaaa aacagatact caatgaccaa | 1860 |
| ttaaaacaag ttcagcagaa cagtttgcac agagattcac ttgttacact taaaagagcc | 1920 |
| ttagaagcaa aagaactagc tcggcagcac ctacgagacc aactggatga agtggagaaa | 1980 |
| gaaactagat caaaactaca ggagattgat attttcaata atcagctgaa ggaactaaga | 2040 |
| gaaatacaca ataagcaaca actccagaag caaaagtcca tggaggctga acgactgaaa | 2100 |
| cagaaagaac aagaacgaaa gatcatagaa ttagaaaaac aaaaagaaga agcccaaaga | 2160 |
| cgagctcagg aaagggacaa gcagtggctg gagcatgtgc agcaggagga cgagcatcag | 2220 |
| agaccaagaa aactccacga agaggaaaaa ctgaaaaggg aggagagtgt caaaaagaag | 2280 |
| gatggcgagg aaaaaggcaa acaggaagca caagacaagc tgggtcggct tttccatcaa | 2340 |
| caccaagaac cagctaagcc agctgtccag gcaccctggt ccactgcaga aaaaggtcca | 2400 |
| cttaccattt ctgcacagga aaatgtaaaa gtggtgtatt accgggcact gtacccccttt | 2460 |
| gaatccagaa gccatgatga aatcactatc cagccaggac atagtcat ggtggatgaa | 2520 |
| agccaaactg gagaacccgg ctggcttgga ggagaattaa aggaaagac agggtggttc | 2580 |
| cctgcaaact atgcagagaa atcccagaaa atgaggttc ccgctccagt gaaaccagtg | 2640 |
| actgattcaa catctgcccc tgccccaaaa ctggccttgc gtgagacccc cgccccttg | 2700 |
| gcagtaacct cttcagagcc ctccacgacc cctaataact gggccgactt cagctccacg | 2760 |
| tggcccacca gcacgaatga gaaaccagaa acggataact gggatgcatg gcagcccag | 2820 |
| ccctctctca ccgttccaag tgccggccag ttaaggcaga ggtccgcctt tactccagcc | 2880 |
| acggccactg gctcctcccc gtctcctgtg ctaggccagg gtgaaaaggt ggaggggcta | 2940 |
| caagctcaag ccctatatcc ttggagagcc aaaaaagaca accacttaaa ttttaacaaa | 3000 |
| aatgatgtca tcaccgtcct ggaacagcaa gacatgtggt ggtttggaga agttcaaggt | 3060 |

```
cagaagggtt ggttccccaa gtcttacgtg aaactcattt cagggcccat aaggaagtct    3120
acaagcatgg attctggttc ttcagagagt cctgctagtc taaagcgagt agcctctcca    3180
gcagccaagc cggtcgtttc gggagaagaa attgcccagg ttattgcctc atacaccgcc    3240
accggccccg agcagctcac tctcgcccct ggtcagctga ttttgatccg aaaaaagaac    3300
ccaggtggat ggtgggaagg agagctgcaa gcacgtggga aaaagcgcca gataggctgg    3360
ttcccagcta attatgtaaa gcttctaagc cctgggacga gcaaaatcac tccaacagag    3420
ccacctaagt caacagcatt agcggcagtg tgccaggtga ttgggatgta cgactacacc    3480
gcgcagaatg acgatgagct ggccttcaac aagggccaga tcatcaacgt cctcaacaag    3540
gaggaccctg actggtggaa aggagaagtc aatggacaag tggggctctt cccatccaat    3600
tatgtgaagc tgaccacaga catggaccca agccagcaat gaatcatatg ttgtccatcc    3660 cccctcagg cttgaaagtc ctcaaagaga cccactatcc catatcactg cccagaggga    3720
tgatgggaga tgcagccttg atcatgtgac ttccagcatg atcacctact gccttctgag    3780
tagaagaact cactgcagag cagtttacct cattttacct tagttgcatg tgatcgcaat    3840
gtttgagtta ttacttgcag agataggagc aaaaattaca aaaacacaca gggtagtggg    3900
tccttttgtg gctttcctag ttactcaaat tgacttcccc ccaccttgc acaggtgctt    3960 tcaatagttt taaaattatt tttaaatata tattttagct tttaataaa caaaataaat    4020 aaatgacttc tttgctattt tggttttgca aaaagaccca ctatcaagga atgctgcatg    4080
tgctattaaa aattgttcca aatgtccata aatctgagac ttgatgtatt ttttcatttt    4140
gtccagtgtt accaactaaa ttgctgcagt ttggggcttt tccccttac catagaagtg    4200 cagaggagtt cagtatctct gttttaaaga cgtatagaat gagcccaatt aaagcgaagg    4260
tgattgtgct tgtttgtgtg tatcagctgt accttgttga gcatgtaata catcctgtac    4320
ataagaaatt agttctttcc atggcaaagc tattaccttg tacgatgctc taatcatatt    4380
gcatttaatt ttattttgca acagtgacct tgtagccaca tgagaaagca ctctgtgttt    4440
ttgttcggtc tcagatttat ctggttgagt tggtgttttg tttggggttt ttaatttgc    4500 gtgtttgcat agcataaaat cagtagacaa caccactgag gtcgttacga tcaacgatat    4560
ccacagtctc ttttttagtct ctgttacatg aagtttatt ccagttactt ttcatggaat    4620
gacctatttt gaacaagtaa ttttcttgac aagaaagaat gtatagaagt ctccctgcaa    4680
ttaatttcca atgtttacat ttttaacta ggactgtgga atttctacag attaatatga    4740
aatggagctc atggtccgtt tgtgtgttag atatgctgta gctgaagccc tgtttgtctt    4800
ttaaacacta gttggaagct ctcaataaaa atgcctgctg ctcacagcac agaaaatggg    4860
gcagggggag cctcaagcac aatctagctg tcctcctaaa gactctgtaa tgctcaatcc    4920
ccttgcgttc tcccggcgct gtcgggaggc tgtgctggtg gtcgtgtaga ggtccttttc    4980 cttttcaaatg gtgcagagag agaggacctt tcctccttgt tcagttgcaa ttcagtattt    5040
tcacggatat gaatgtaaaa tatataaata tataaacctg aggatttaac aaatgtaaaa    5100 caacctttg aattagttcc gagtatagat aattaaattt ttaaaacaaa agtaaaaaaa    5160
aaaaaaaaaa aaaaaaaaaa aaaagtcgac gcggccgcg                          5199
```

<210> SEQ ID NO 2
<211> LENGTH: 1143
<212> TYPE: PRT
<213> ORGANISM: Homo sapiens

```
<400> SEQUENCE: 2

Met Ala Gln Phe Pro Thr Pro Phe Gly Gly Ser Leu Asp Ile Trp Ala
1               5                   10                  15

Ile Thr Val Glu Glu Arg Ala Lys His Asp Gln Gln Phe His Ser Leu
            20                  25                  30

Lys Pro Ile Ser Gly Phe Ile Thr Gly Asp Gln Ala Arg Asn Phe Phe
        35                  40                  45

Phe Gln Ser Gly Leu Pro Gln Pro Val Leu Ala Gln Ile Trp Ala Leu
    50                  55                  60

Ala Asp Met Asn Asn Asp Gly Arg Met Asp Gln Val Glu Phe Ser Ile
65                  70                  75                  80

Ala Met Lys Leu Ile Lys Leu Lys Leu Gln Gly Tyr Gln Leu Pro Ser
                85                  90                  95

Ala Leu Pro Pro Val Met Lys Gln Gln Pro Val Ala Ile Ser Ser Ala
            100                 105                 110

Pro Ala Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Val Pro Pro Val Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
        275                 280                 285

Ala Met Ser Gly Gln Pro Leu Pro Pro Val Leu Pro Pro Glu Tyr Ile
    290                 295                 300

Pro Pro Ser Phe Arg Arg Val Arg Ser Gly Ser Gly Ile Ser Val Ile
305                 310                 315                 320

Ser Ser Thr Ser Val Asp Gln Arg Leu Pro Glu Glu Pro Val Leu Glu
                325                 330                 335

Asp Glu Gln Gln Gln Leu Glu Lys Lys Leu Pro Val Thr Phe Glu Asp
            340                 345                 350

Lys Lys Arg Glu Asn Phe Glu Arg Gly Asn Leu Glu Leu Glu Lys Arg
        355                 360                 365

Arg Gln Ala Leu Leu Glu Gln Arg Lys Glu Gln Glu Arg Leu Ala
    370                 375                 380

Gln Leu Glu Arg Ala Glu Gln Glu Arg Lys Glu Arg Glu Arg Gln Glu
385                 390                 395                 400

Gln Glu Arg Lys Arg Gln Leu Glu Leu Glu Lys Gln Leu Glu Lys Gln
                405                 410                 415
```

-continued

```
Arg Glu Leu Glu Arg Gln Arg Glu Glu Arg Lys Glu Ile Glu
            420                 425                 430

Arg Arg Glu Ala Ala Lys Arg Glu Leu Glu Arg Gln Arg Gln Leu Glu
            435                 440                 445

Trp Glu Arg Asn Arg Arg Gln Glu Leu Leu Asn Gln Arg Asn Lys Glu
            450                 455                 460

Gln Glu Asp Ile Val Val Leu Lys Ala Lys Lys Thr Leu Glu Phe
465                 470                 475                 480

Glu Leu Glu Ala Leu Asn Asp Lys Lys His Gln Leu Glu Gly Lys Leu
                485                 490                 495

Gln Asp Ile Arg Cys Arg Leu Thr Thr Gln Arg Gln Glu Ile Glu Ser
                500                 505                 510

Thr Asn Lys Ser Arg Glu Leu Arg Ile Ala Glu Ile Thr His Leu Gln
                515                 520                 525

Gln Gln Leu Gln Glu Ser Gln Gln Met Leu Gly Arg Leu Ile Pro Glu
            530                 535                 540

Lys Gln Ile Leu Asn Asp Gln Leu Lys Gln Val Gln Gln Asn Ser Leu
545                 550                 555                 560

His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
                580                 585                 590

Thr Arg Ser Lys Leu Gln Glu Ile Asp Ile Phe Asn Asn Gln Leu Lys
            595                 600                 605

Glu Leu Arg Glu Ile His Asn Lys Gln Gln Leu Gln Lys Gln Lys Ser
            610                 615                 620

Met Glu Ala Glu Arg Leu Lys Gln Lys Glu Gln Glu Arg Lys Ile Ile
625                 630                 635                 640

Glu Leu Glu Lys Gln Lys Glu Glu Ala Gln Arg Arg Ala Gln Glu Arg
                645                 650                 655

Asp Lys Gln Trp Leu Glu His Val Gln Gln Glu Asp Glu His Gln Arg
                660                 665                 670

Pro Arg Lys Leu His Glu Glu Lys Leu Lys Arg Glu Glu Ser Val
            675                 680                 685

Lys Lys Lys Asp Gly Glu Glu Lys Gly Lys Gln Glu Ala Gln Asp Lys
            690                 695                 700

Leu Gly Arg Leu Phe His Gln His Gln Glu Pro Ala Lys Pro Ala Val
705                 710                 715                 720

Gln Ala Pro Trp Ser Thr Ala Glu Lys Gly Pro Leu Thr Ile Ser Ala
                725                 730                 735

Gln Glu Asn Val Lys Val Val Tyr Tyr Arg Ala Leu Tyr Pro Phe Glu
                740                 745                 750

Ser Arg Ser His Asp Glu Ile Thr Ile Gln Pro Gly Asp Ile Val Met
            755                 760                 765

Val Asp Glu Ser Gln Thr Gly Glu Pro Gly Trp Leu Gly Gly Glu Leu
770                 775                 780

Lys Gly Lys Thr Gly Trp Phe Pro Ala Asn Tyr Ala Glu Lys Ile Pro
785                 790                 795                 800

Glu Asn Glu Val Pro Ala Pro Val Lys Pro Val Thr Asp Ser Thr Ser
                805                 810                 815

Ala Pro Ala Pro Lys Leu Ala Leu Arg Glu Thr Pro Ala Pro Leu Ala
            820                 825                 830
```

-continued

Val Thr Ser Ser Glu Pro Ser Thr Thr Pro Asn Asn Trp Ala Asp Phe
        835                 840                 845

Ser Ser Thr Trp Pro Thr Ser Thr Asn Glu Lys Pro Glu Thr Asp Asn
        850                 855                 860

Trp Asp Ala Trp Ala Ala Gln Pro Ser Leu Thr Val Pro Ser Ala Gly
865                 870                 875                 880

Gln Leu Arg Gln Arg Ser Ala Phe Thr Pro Ala Thr Ala Thr Gly Ser
                885                 890                 895

Ser Pro Ser Pro Val Leu Gly Gln Gly Glu Lys Val Glu Gly Leu Gln
            900                 905                 910

Ala Gln Ala Leu Tyr Pro Trp Arg Ala Lys Lys Asp Asn His Leu Asn
        915                 920                 925

Phe Asn Lys Asn Asp Val Ile Thr Val Leu Glu Gln Gln Asp Met Trp
    930                 935                 940

Trp Phe Gly Glu Val Gln Gly Gln Lys Gly Trp Phe Pro Lys Ser Tyr
945                 950                 955                 960

Val Lys Leu Ile Ser Gly Pro Ile Arg Lys Ser Thr Ser Met Asp Ser
                965                 970                 975

Gly Ser Ser Glu Ser Pro Ala Ser Leu Lys Arg Val Ala Ser Pro Ala
            980                 985                 990

Ala Lys Pro Val Val Ser Gly Glu Glu Ile Ala Gln Val Ile Ala Ser
        995                 1000                1005

Tyr Thr Ala Thr Gly Pro Glu Gln Leu Thr Leu Ala Pro Gly Gln Leu
    1010                1015                1020

Ile Leu Ile Arg Lys Lys Asn Pro Gly Gly Trp Trp Glu Gly Glu Leu
1025                1030                1035                1040

Gln Ala Arg Gly Lys Lys Arg Gln Ile Gly Trp Phe Pro Ala Asn Tyr
                1045                1050                1055

Val Lys Leu Leu Ser Pro Gly Thr Ser Lys Ile Thr Pro Thr Glu Pro
            1060                1065                1070

Pro Lys Ser Thr Ala Leu Ala Ala Val Cys Gln Val Ile Gly Met Tyr
        1075                1080                1085

Asp Tyr Thr Ala Gln Asn Asp Asp Glu Leu Ala Phe Asn Lys Gly Gln
    1090                1095                1100

Ile Ile Asn Val Leu Asn Lys Glu Asp Pro Asp Trp Trp Lys Gly Glu
1105                1110                1115                1120

Val Asn Gly Gln Val Gly Leu Phe Pro Ser Asn Tyr Val Lys Leu Thr
                1125                1130                1135

Thr Asp Met Asp Pro Ser Gln
            1140

<210> SEQ ID NO 3
<211> LENGTH: 5458
<212> TYPE: DNA
<213> ORGANISM: Homo sapiens

<400> SEQUENCE: 3
gcacgagagg gagcgaagga ggtagagaag agtggaggcg ccaggggagg gagcgtagct    60
tggttgctcc gtagtacggc ggctcgcgag gaagaatccc gagcgggctc cgggacggac   120
agagaggcgg gcggggatgg tgtgcggggc tgcggctcct gcgtccctcc cagcggcgcg   180
tgagcggcac tgatttgtcc ctggggcggc agcgcggacc cgcccggaga tgaggcgtcg   240
attagcaagg taaagtaac agaaccatgg ctcagtttcc aacaccttt ggtggcagcc    300 tggatatctg ggccataact gtagaggaaa gagcgaagca tgatcagcag ttccatagtt   360

-continued

```
taaagccaat atctggattc attactggtg atcaagctag aaactttttt tttcaatctg      420
ggttacctca acctgtttta gcacagatat gggcactagc tgacatgaat aatgatggaa      480
gaatggatca agtggagttt tccatagcta tgaaacttat caaactgaag ctacaaggat      540
atcagctacc ctctgcactt cccctgtca tgaaacagca accagttgct atttctagcg       600
caccagcatt tggtatggga ggtatcgcca gcatgccacc gcttacagct gttgctccag      660
tgccaatggg atccattcca gttgttggaa tgtctccaac cctagtatct tctgttccca      720
cagcagctgt gccccccctg ctaacgggg ctcccctgt tatacaacct ctgcctgcat        780
ttgctcatcc tgcagccaca ttgccaaaga gttcttcctt tagtagatct ggtccagggt      840
cacaactaaa cactaaatta caaaaggcac agtcatttga tgtggccagt gtcccaccag      900
tggcagagtg ggctgttcct cagtcatcaa gactgaaata caggcaatta ttcaatagtc      960
atgacaaaac tatgagtgga cacttaacag gtccccaagc aagaactatt cttatgcagt     1020
caagtttacc acaggctcag ctggcttcaa tatggaatct ttctgacatt gatcaagatg     1080
gaaaacttac agcagaggaa tttatcctgg caatgcacct cattgatgta gctatgtctg     1140
gccaaccact gccacctgtc ctgcctccag aatacattcc accttctttt agaagagttc     1200
gatctggcag tggtatatct gtcataagct caacatctgt agatcagagg ctaccgagag     1260
aaccagtttt agaagatgaa caacaacaat tagaaaagaa attacctgta acgtttgaag     1320
ataagaagcg ggagaacttt gaacgtggca acctggaact ggagaaacga aggcaagctc     1380
tcctggaaca gcagcgcaag gagcaggagc gcctggccca gctggagcgg gcggagcagg     1440
agaggaagga gcgtgagcgc caggagcaag agcgcaaaag acaactggaa ctggagaagc     1500
aactggaaaa gcagcgggag ctagaacggc agagagagga ggagaggagg aaagaaattg     1560
agaggcgaga ggctgcaaaa cgggaacttg aaaggcaacg acaacttgag tgggaacgga     1620
atcgaaggca agaactacta aatcaaagaa acaaagaaca agaggacata gttgtactga     1680
aagcaaagaa aaagactttg gaatttgaat tagaagctct aaatgataaa aagcatcaac     1740
tagaagggaa acttcaagat atcagatgtc gattgaccac ccaaaggcaa gaaattgaga     1800
gcacaaacaa atctagagag ttgagaattg ccgaaatcac ccatctacag caacaattac     1860
aggaatctca gcaaatgctt ggaagactta ttccagaaaa acagatactc aatgaccaat     1920
taaaacaagt tcagcagaac agtttgcaca gagattcact tgttacactt aaaagagcct     1980
tagaagcaaa agaactagct cggcagcacc tacgagacca actggatgaa gtggagaaag     2040
aaactagatc aaaactacag gagattgata ttttcaataa tcagctgaag gaactaagag     2100
aaatacacaa taagcaacaa ctccagaagc aaaagtccat ggaggctgaa cgactgaaac     2160
agaaagaaca agaacgaaag atcatagaat tagaaaaaca aaagaagaa gcccaaagac      2220 gagctcagga aagggacaag cagtggctgg agcatgtgca gcaggaggac gagcatcaga     2280
gaccaagaaa actccacgaa gaggaaaaac tgaaagggga ggagagtgtc aaaagaaagg     2340
atggcgagga aaaggcaaa caggaagcac aagacaagct gggtcggctt ttccatcaac      2400
accaagaacc agctaagcca gctgtccagg caccctggtc cactgcagaa aaaggtccac     2460
ttaccatttc tgcacaggaa aatgtaaaag tggtgtatta ccgggcactg tacccctttg     2520
aatccagaag ccatgatgaa atcactatcc agccaggaga catagtcatg gttaaagggg     2580
aatgggtgga tgaaagccaa actggagaac ccggctggct tggaggagaa ttaaaggaa      2640 agacagggtg gttccctgca aactatgcag agaaaatccc agaaaatgag gttcccgctc     2700
```

```
cagtgaaacc agtgactgat tcaacatctg cccctgcccc caaactggcc ttgcgtgaga    2760
cccccgcccc tttggcagta acctcttcag agccctccac gacccctaat aactgggccg    2820
acttcagctc cacgtggccc accagcacga atgagaaacc agaaacggat aactgggatg    2880
catgggcagc ccagccctct ctcaccgttc aagtgccgg ccagttaagg cagaggtccg     2940
cctttactcc agccacggcc actggctcct ccccgtctcc tgtgctaggc cagggtgaaa    3000
aggtggaggg gctacaagct caagcccta atccttggag agccaaaaaa gacaaccact     3060
taaattttaa caaaaatgat gtcatcaccg tcctggaaca gcaagacatg tggtggtttg    3120
gagaagttca aggtcagaag ggttggttcc ccaagtctta cgtgaaactc atttcagggc    3180
ccataaggaa gtctacaagc atggattctg gttcttcaga gagtcctgct agtctaaagc    3240
gagtagcctc tccagcagcc aagccggtcg tttcgggaga agaatttatt gccatgtaca    3300
cttacgagag ttctgagcaa ggagatttaa cctttcagca aggggatgtg attttggtta    3360
ccaagaaaga tggtgactgg tggacaggaa cagtgggcga caaggccgga gtcttccctt    3420
ctaactatgt gaggcttaaa gattcagagg gctctggaac tgctgggaaa cagggagtt    3480
taggaaaaaa acctgaaatt gcccaggtta ttgcctcata caccgccacc ggccccgagc    3540
agctcactct cgcccctggt cagctgattt tgatccgaaa aaagaaccca ggtggatggt    3600
gggaaggaga gctgcaagca cgtgggaaaa agcgccagat aggctggttc ccagctaatt    3660
atgtaaagct tctaagccct gggacgagca aaatcactcc aacagagcca cctaagtcaa    3720
cagcattagc ggcagtgtgc caggtgattg ggatgtacga ctacaccgcg cagaatgacg    3780
atgagctggc cttcaacaag ggccagatca tcaacgtcct caacaaggag gaccctgact    3840
ggtggaaagg agaagtcaat ggacaagtgg ggctcttccc atccaattat gtgaagctga    3900
ccacagacat ggacccaagc cagcaatgaa tcatatgttg tccatccccc cctcaggctt    3960
gaaagtcctc aaagagaccc actatcccat atcactgccc agaggatga tgggagatgc    4020
agccttgatc atgtgacttc cagcatgatc acctactgcc ttctgagtag aagaactcac    4080
tgcagagcag tttacctcat tttaccttag ttgcatgtga tcgcaatgtt tgagttatta    4140
cttgcagaga taggagcaaa aattacaaaa acacacaggg tagtgggtcc ttttgtggct    4200
ttcctagtta ctcaaattga ctttccccca cctttgcaca ggtgctttca atagttttaa    4260
aattattttt aaatatatat tttagctttt taataaacaa aataaataaa tgacttcttt    4320
gctattttgg ttttgcaaaa agacccacta tcaaggaatg ctgcatgtgc tattaaaaat    4380
tgttccaaat gtccataaat ctgagacttg atgtattttt tcattttgtc cagtgttacc    4440
aactaaattg tgcagtttgg ggcttttccc ccttaccata gaagtgcaga ggagttcagt    4500
atctctgttt taaagacgta tagaatgagc ccaattaaag cgaaggtgtt tgtgcttgtt    4560
tgtgtgtatc agctgtacct tgttgagcat gtaatacatc ctgtacataa gaaattagtt    4620
cttttccatgg caaagctatt accttgtacg atgctctaat catattgcat ttaattttat    4680
tttgcacagt gaccttgtag ccacatgaga aagcactctg tgttttttgtt cggtctcaga    4740
tttatctggt tgagttggtg ttttgtttgg ggttttttaat tttgcgtgtt tgcatagcat    4800
aaaatcagta gacaacacca ctgaggtcgt tacgatcaac gatatccaca gtctcttttt    4860
agtctctgtt acatgaagtt ttattccagt tacttttcat ggaatgacct attttgaaca    4920
agtaattttc ttgacaagaa agaatgtata gaagtctccc tgcaattaat ttccaatgtt    4980
tacattttt aactagactg tggaatttct acagattaat atgaaatgga gctcatggtc    5040
cgtttgtgtg ttagatatgc tgtagctgaa gccctgtttg tcttttaaac actagttgga    5100
```

-continued

```
agctctcaat aaaaatgcct gctgctcaca gcacagaaaa tggggcaggg ggagcctcaa    5160
gcacaatcta gctgtcctcc taaagactct gtaatgctca ctcccctcgc gttctcccgg    5220
cgctgtcggg aggctgtgct ggtggtcgtg tagaggtcct tctcctttca catggtgcag    5280
agagcgagga cctctcctcc tcgttcagtt gcacttcagt attttcacgg atatgaatgt    5340
aaaatatata aatatataaa cctgcggctt taacaactgt aatacaacct tttgaattag    5400
ttccgtgtat agataattaa attcttcata caaaagttaa aaaaaaaaaa aaaaaaa       5458
```

<210> SEQ ID NO 4
<211> LENGTH: 1220
<212> TYPE: PRT
<213> ORGANISM: Homo sapiens

<400> SEQUENCE: 4

```
Met Ala Gln Phe Pro Thr Pro Phe Gly Gly Ser Leu Asp Ile Trp Ala
  1               5                  10                  15

Ile Thr Val Glu Glu Arg Ala Lys His Asp Gln Gln Phe His Ser Leu
                 20                  25                  30

Lys Pro Ile Ser Gly Phe Ile Thr Gly Asp Gln Ala Arg Asn Phe Phe
             35                  40                  45

Phe Gln Ser Gly Leu Pro Gln Pro Val Leu Ala Gln Ile Trp Ala Leu
         50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
            100                 105                 110

Pro Ala Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Val Pro Pro Val Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
        275                 280                 285

Ala Met Ser Gly Gln Pro Leu Pro Pro Val Leu Pro Pro Glu Tyr Ile
    290                 295                 300

Pro Pro Ser Phe Arg Arg Val Arg Ser Gly Ser Gly Ile Ser Val Ile
```

-continued

```
         305                 310                 315                 320
Ser Ser Thr Ser Val Asp Gln Arg Leu Pro Glu Glu Pro Val Leu Glu
                 325                 330                 335

Asp Glu Gln Gln Gln Leu Glu Lys Lys Leu Pro Val Thr Phe Glu Asp
                 340                 345                 350

Lys Lys Arg Glu Asn Phe Glu Arg Gly Asn Leu Glu Leu Glu Lys Arg
                 355                 360                 365

Arg Gln Ala Leu Leu Glu Gln Arg Lys Glu Gln Glu Arg Leu Ala
         370                 375                 380

Gln Leu Glu Arg Ala Gln Glu Arg Lys Glu Arg Glu Arg Gln Glu
385                  390                 395                 400

Gln Glu Arg Lys Arg Gln Leu Glu Leu Glu Lys Gln Leu Glu Lys Gln
                 405                 410                 415

Arg Glu Leu Glu Arg Gln Arg Glu Glu Arg Arg Lys Glu Ile Glu
                 420                 425                 430

Arg Arg Glu Ala Ala Lys Arg Glu Leu Glu Arg Gln Arg Gln Leu Glu
                 435                 440                 445

Trp Glu Arg Asn Arg Arg Gln Glu Leu Leu Asn Gln Arg Asn Lys Glu
         450                 455                 460

Gln Glu Asp Ile Val Val Leu Lys Ala Lys Lys Thr Leu Glu Phe
465                  470                 475                 480

Glu Leu Glu Ala Leu Asn Asp Lys Lys His Gln Leu Glu Gly Lys Leu
                 485                 490                 495

Gln Asp Ile Arg Cys Arg Leu Thr Thr Gln Arg Gln Glu Ile Glu Ser
                 500                 505                 510

Thr Asn Lys Ser Arg Glu Leu Arg Ile Ala Glu Ile Thr His Leu Gln
         515                 520                 525

Gln Gln Leu Gln Glu Ser Gln Met Leu Gly Arg Leu Ile Pro Glu
         530                 535                 540

Lys Gln Ile Leu Asn Asp Gln Leu Lys Gln Val Gln Gln Asn Ser Leu
545                  550                 555                 560

His Arg Asp Ser Leu Val Thr Leu Lys Arg Ala Leu Glu Ala Lys Glu
                 565                 570                 575

Leu Ala Arg Gln His Leu Arg Asp Gln Leu Asp Glu Val Glu Lys Glu
                 580                 585                 590

Thr Arg Ser Lys Leu Gln Glu Ile Asp Ile Phe Asn Asn Gln Leu Lys
         595                 600                 605

Glu Leu Arg Glu Ile His Asn Lys Gln Gln Leu Gln Lys Gln Lys Ser
         610                 615                 620

Met Glu Ala Glu Arg Leu Lys Gln Lys Glu Gln Glu Arg Lys Ile Ile
625                  630                 635                 640

Glu Leu Glu Lys Gln Lys Glu Glu Ala Gln Arg Arg Ala Gln Glu Arg
                 645                 650                 655

Asp Lys Gln Trp Leu Glu His Val Gln Glu Asp Glu His Gln Arg
                 660                 665                 670

Pro Arg Lys Leu His Glu Glu Lys Leu Lys Arg Glu Glu Ser Val
         675                 680                 685

Lys Lys Lys Asp Gly Glu Glu Lys Gly Lys Gln Glu Ala Gln Asp Lys
         690                 695                 700

Leu Gly Arg Leu Phe His Gln His Gln Glu Pro Ala Lys Pro Ala Val
705                  710                 715                 720

Gln Ala Pro Trp Ser Thr Ala Glu Lys Gly Pro Leu Thr Ile Ser Ala
                 725                 730                 735
```

-continued

```
Gln Glu Asn Val Lys Val Val Tyr Tyr Arg Ala Leu Tyr Pro Phe Glu
            740                 745                 750

Ser Arg Ser His Asp Glu Ile Thr Ile Gln Pro Gly Asp Ile Val Met
        755                 760                 765

Val Lys Gly Glu Trp Val Asp Glu Ser Gln Thr Gly Glu Pro Gly Trp
770                 775                 780

Leu Gly Gly Glu Leu Lys Gly Lys Thr Gly Trp Phe Pro Ala Asn Tyr
785                 790                 795                 800

Ala Glu Lys Ile Pro Glu Asn Glu Val Pro Ala Pro Val Lys Pro Val
            805                 810                 815

Thr Asp Ser Thr Ser Ala Pro Ala Pro Lys Leu Ala Leu Arg Glu Thr
        820                 825                 830

Pro Ala Pro Leu Ala Val Thr Ser Glu Pro Ser Thr Thr Pro Asn
            835                 840                 845

Asn Trp Ala Asp Phe Ser Ser Thr Trp Pro Thr Ser Thr Asn Glu Lys
850                 855                 860

Pro Glu Thr Asp Asn Trp Asp Ala Trp Ala Ala Gln Pro Ser Leu Thr
865                 870                 875                 880

Val Pro Ser Ala Gly Gln Leu Arg Gln Arg Ser Ala Phe Thr Pro Ala
            885                 890                 895

Thr Ala Thr Gly Ser Ser Pro Ser Pro Val Leu Gly Gln Gly Glu Lys
        900                 905                 910

Val Glu Gly Leu Gln Ala Gln Ala Leu Tyr Pro Trp Arg Ala Lys Lys
            915                 920                 925

Asp Asn His Leu Asn Phe Asn Lys Asn Asp Val Ile Thr Val Leu Glu
930                 935                 940

Gln Gln Asp Met Trp Trp Phe Gly Glu Val Gln Gly Lys Gly Trp
945                 950                 955                 960

Phe Pro Lys Ser Tyr Val Lys Leu Ile Ser Gly Pro Ile Arg Lys Ser
            965                 970                 975

Thr Ser Met Asp Ser Gly Ser Ser Glu Ser Pro Ala Ser Leu Lys Arg
        980                 985                 990

Val Ala Ser Pro Ala Ala Lys Pro Val Val Ser Gly Glu Glu Phe Ile
            995                1000                1005

Ala Met Tyr Thr Tyr Glu Ser Ser Glu Gln Gly Asp Leu Thr Phe Gln
        1010                1015                1020

Gln Gly Asp Val Ile Leu Val Thr Lys Lys Asp Gly Asp Trp Trp Thr
1025                1030                1035                1040

Gly Thr Val Gly Asp Lys Ala Gly Val Phe Pro Ser Asn Tyr Val Arg
            1045                1050                1055

Leu Lys Asp Ser Glu Gly Ser Gly Thr Ala Gly Lys Thr Gly Ser Leu
        1060                1065                1070

Gly Lys Lys Pro Glu Ile Ala Gln Val Ile Ala Ser Tyr Thr Ala Thr
            1075                1080                1085

Gly Pro Glu Gln Leu Thr Leu Ala Pro Gly Gln Leu Ile Leu Ile Arg
        1090                1095                1100

Lys Lys Asn Pro Gly Gly Trp Trp Glu Gly Glu Leu Gln Ala Arg Gly
1105                1110                1115                1120

Lys Lys Arg Gln Ile Gly Trp Phe Pro Ala Asn Tyr Val Lys Leu Leu
            1125                1130                1135

Ser Pro Gly Thr Ser Lys Ile Thr Pro Thr Glu Pro Pro Lys Ser Thr
        1140                1145                1150
```

-continued

```
Ala Leu Ala Ala Val Cys Gln Val Ile Gly Met Tyr Asp Tyr Thr Ala
        1155                1160                1165

Gln Asn Asp Asp Glu Leu Ala Phe Asn Lys Gly Gln Ile Ile Asn Val
    1170                1175                1180

Leu Asn Lys Glu Asp Pro Asp Trp Trp Lys Gly Glu Val Asn Gly Gln
1185                1190                1195                1200

Val Gly Leu Phe Pro Ser Asn Tyr Val Lys Leu Thr Thr Asp Met Asp
            1205                1210                1215

Pro Ser Gln Gln
        1220

<210> SEQ ID NO 5
<211> LENGTH: 23
<212> TYPE: PRT
<213> ORGANISM: Homo sapiens
<220> FEATURE:
<223> OTHER INFORMATION: From Seq ID 5 to ID 38, there are 34 pretein
      sequences translated from Seq ID No. 3. Together,
      they form the whole protein sequence.

<400> SEQUENCE: 5

Thr Arg Gly Ser Glu Gly Gly Arg Glu Glu Trp Arg Arg Gln Gly Arg
1               5                   10                  15

Glu Arg Ser Leu Val Ala Pro
            20

<210> SEQ ID NO 6
<211> LENGTH: 52
<212> TYPE: PRT
<213> ORGANISM: Homo sapiens

<400> SEQUENCE: 6

Tyr Gly Gly Ser Arg Gly Arg Ile Pro Ser Gly Leu Arg Asp Gly Gln
1               5                   10                  15

Arg Gly Gly Arg Gly Trp Cys Ala Gly Leu Arg Leu Leu Arg Pro Ser
            20                  25                  30

Gln Arg Arg Val Ser Gly Thr Asp Leu Ser Leu Gly Arg Gln Arg Gly
        35                  40                  45

Pro Ala Arg Arg
    50

<210> SEQ ID NO 7
<211> LENGTH: 3
<212> TYPE: PRT
<213> ORGANISM: Homo sapiens

<400> SEQUENCE: 7

Gly Val Asp
1

<210> SEQ ID NO 8
<211> LENGTH: 1227
<212> TYPE: PRT
<213> ORGANISM: Homo sapiens

<400> SEQUENCE: 8

Gln Gly Lys Ser Asn Arg Thr Met Ala Gln Phe Pro Thr Pro Phe Gly
1               5                   10                  15

Gly Ser Leu Asp Ile Trp Ala Ile Thr Val Glu Glu Arg Ala Lys His
            20                  25                  30

Asp Gln Gln Phe His Ser Leu Lys Pro Ile Ser Gly Phe Ile Thr Gly
```

```
            35                  40                  45
Asp Gln Ala Arg Asn Phe Phe Phe Gln Ser Gly Leu Pro Gln Pro Val
 50                  55                  60

Leu Ala Gln Ile Trp Ala Leu Ala Asp Met Asn Asn Asp Gly Arg Met
 65                  70                  75                  80

Asp Gln Val Glu Phe Ser Ile Ala Met Lys Leu Ile Lys Leu Lys Leu
                 85                  90                  95

Gln Gly Tyr Gln Leu Pro Ser Ala Leu Pro Pro Val Met Lys Gln Gln
                100                 105                 110

Pro Val Ala Ile Ser Ser Ala Pro Ala Phe Gly Met Gly Ile Ala
                115                 120                 125

Ser Met Pro Pro Leu Thr Ala Val Ala Pro Val Pro Met Gly Ser Ile
130                 135                 140

Pro Val Val Gly Met Ser Pro Thr Leu Val Ser Ser Val Pro Thr Ala
145                 150                 155                 160

Ala Val Pro Pro Leu Ala Asn Gly Ala Pro Pro Val Ile Gln Pro Leu
                165                 170                 175

Pro Ala Phe Ala His Pro Ala Ala Thr Leu Pro Lys Ser Ser Ser Phe
                180                 185                 190

Ser Arg Ser Gly Pro Gly Ser Gln Leu Asn Thr Lys Leu Gln Lys Ala
                195                 200                 205

Gln Ser Phe Asp Val Ala Ser Val Pro Pro Val Ala Glu Trp Ala Val
                210                 215                 220

Pro Gln Ser Ser Arg Leu Lys Tyr Arg Gln Leu Phe Asn Ser His Asp
225                 230                 235                 240

Lys Thr Met Ser Gly His Leu Thr Gly Pro Gln Ala Arg Thr Ile Leu
                245                 250                 255

Met Gln Ser Ser Leu Pro Gln Ala Gln Leu Ala Ser Ile Trp Asn Leu
                260                 265                 270

Ser Asp Ile Asp Gln Asp Gly Lys Leu Thr Ala Glu Glu Phe Ile Leu
                275                 280                 285

Ala Met His Leu Ile Asp Val Ala Met Ser Gly Gln Pro Leu Pro Pro
290                 295                 300

Val Leu Pro Pro Glu Tyr Ile Pro Pro Ser Phe Arg Arg Val Arg Ser
305                 310                 315                 320

Gly Ser Gly Ile Ser Val Ile Ser Ser Thr Ser Val Asp Gln Arg Leu
                325                 330                 335

Pro Glu Glu Pro Val Leu Glu Asp Glu Gln Gln Leu Glu Lys Lys
                340                 345                 350

Leu Pro Val Thr Phe Glu Asp Lys Lys Arg Glu Asn Phe Glu Arg Gly
                355                 360                 365

Asn Leu Glu Leu Glu Lys Arg Arg Gln Ala Leu Leu Glu Gln Gln Arg
370                 375                 380

Lys Glu Gln Glu Arg Leu Ala Gln Leu Glu Arg Ala Glu Gln Glu Arg
385                 390                 395                 400

Lys Glu Arg Glu Arg Gln Glu Gln Glu Arg Lys Arg Gln Leu Glu Leu
                405                 410                 415

Glu Lys Gln Leu Glu Lys Gln Arg Glu Leu Glu Arg Gln Arg Glu Glu
                420                 425                 430

Glu Arg Arg Lys Glu Ile Glu Arg Arg Glu Ala Ala Lys Arg Glu Leu
                435                 440                 445

Glu Arg Gln Arg Gln Leu Glu Trp Glu Arg Asn Arg Arg Gln Glu Leu
                450                 455                 460
```

-continued

```
Leu Asn Gln Arg Asn Lys Glu Gln Glu Asp Ile Val Val Leu Lys Ala
465                 470                 475                 480

Lys Lys Lys Thr Leu Glu Phe Glu Leu Glu Ala Leu Asn Asp Lys Lys
                485                 490                 495

His Gln Leu Glu Gly Lys Leu Gln Asp Ile Arg Cys Arg Leu Thr Thr
                500                 505                 510

Gln Arg Gln Glu Ile Glu Ser Thr Asn Lys Ser Arg Glu Leu Arg Ile
            515                 520                 525

Ala Glu Ile Thr His Leu Gln Gln Gln Leu Gln Glu Ser Gln Gln Met
        530                 535                 540

Leu Gly Arg Leu Ile Pro Glu Lys Gln Ile Leu Asn Asp Gln Leu Lys
545                 550                 555                 560

Gln Val Gln Gln Asn Ser Leu His Arg Asp Ser Leu Val Thr Leu Lys
                565                 570                 575

Arg Ala Leu Glu Ala Lys Glu Leu Ala Arg Gln His Leu Arg Asp Gln
            580                 585                 590

Leu Asp Glu Val Glu Lys Glu Thr Arg Ser Lys Leu Gln Glu Ile Asp
        595                 600                 605

Ile Phe Asn Asn Gln Leu Lys Glu Leu Arg Glu Ile His Asn Lys Gln
610                 615                 620

Gln Leu Gln Lys Gln Lys Ser Met Glu Ala Glu Arg Leu Lys Gln Lys
625                 630                 635                 640

Glu Gln Glu Arg Lys Ile Ile Glu Leu Glu Lys Gln Lys Glu Glu Ala
                645                 650                 655

Gln Arg Arg Ala Gln Glu Arg Asp Lys Gln Trp Leu Glu His Val Gln
            660                 665                 670

Gln Glu Asp Glu His Gln Arg Pro Arg Lys Leu His Glu Glu Lys
        675                 680                 685

Leu Lys Arg Glu Glu Ser Val Lys Lys Asp Gly Glu Glu Lys Gly
690                 695                 700

Lys Gln Glu Ala Gln Asp Lys Leu Gly Arg Leu Phe His Gln His Gln
705                 710                 715                 720

Glu Pro Ala Lys Pro Ala Val Gln Ala Pro Trp Ser Thr Ala Glu Lys
                725                 730                 735

Gly Pro Leu Thr Ile Ser Ala Gln Glu Asn Val Lys Val Val Tyr Tyr
            740                 745                 750

Arg Ala Leu Tyr Pro Phe Glu Ser Arg Ser His Asp Glu Ile Thr Ile
        755                 760                 765

Gln Pro Gly Asp Ile Val Met Val Lys Gly Glu Trp Val Asp Glu Ser
770                 775                 780

Gln Thr Gly Glu Pro Gly Trp Leu Gly Gly Glu Leu Lys Gly Lys Thr
785                 790                 795                 800

Gly Trp Phe Pro Ala Asn Tyr Ala Glu Lys Ile Pro Glu Asn Glu Val
                805                 810                 815

Pro Ala Pro Val Lys Pro Val Thr Asp Ser Thr Ser Ala Pro Ala Pro
            820                 825                 830

Lys Leu Ala Leu Arg Glu Thr Pro Ala Pro Leu Ala Val Thr Ser Ser
        835                 840                 845

Glu Pro Ser Thr Thr Pro Asn Asn Trp Ala Asp Phe Ser Ser Thr Trp
850                 855                 860

Pro Thr Ser Thr Asn Glu Lys Pro Glu Thr Asp Asn Trp Asp Ala Trp
865                 870                 875                 880
```

-continued

```
Ala Ala Gln Pro Ser Leu Thr Val Pro Ser Ala Gly Gln Leu Arg Gln
            885                 890                 895

Arg Ser Ala Phe Thr Pro Ala Thr Ala Thr Gly Ser Ser Pro Ser Pro
        900                 905                 910

Val Leu Gly Gln Gly Glu Lys Val Glu Gly Leu Gln Ala Gln Ala Leu
    915                 920                 925

Tyr Pro Trp Arg Ala Lys Lys Asp Asn His Leu Asn Phe Asn Lys Asn
930                 935                 940

Asp Val Ile Thr Val Leu Glu Gln Gln Asp Met Trp Trp Phe Gly Glu
945                 950                 955                 960

Val Gln Gly Gln Lys Gly Trp Phe Pro Lys Ser Tyr Val Lys Leu Ile
                965                 970                 975

Ser Gly Pro Ile Arg Lys Ser Thr Ser Met Asp Ser Gly Ser Ser Glu
            980                 985                 990

Ser Pro Ala Ser Leu Lys Arg Val Ala Ser Pro Ala Ala Lys Pro Val
        995                 1000                1005

Val Ser Gly Glu Glu Phe Ile Ala Met Tyr Thr Tyr Glu Ser Ser Glu
    1010                1015                1020

Gln Gly Asp Leu Thr Phe Gln Gln Gly Asp Val Ile Leu Val Thr Lys
1025                1030                1035                1040

Lys Asp Gly Asp Trp Trp Thr Gly Thr Val Gly Asp Lys Ala Gly Val
                1045                1050                1055

Phe Pro Ser Asn Tyr Val Arg Leu Lys Asp Ser Glu Gly Ser Gly Thr
            1060                1065                1070

Ala Gly Lys Thr Gly Ser Leu Gly Lys Lys Pro Glu Ile Ala Gln Val
        1075                1080                1085

Ile Ala Ser Tyr Thr Ala Thr Gly Pro Glu Gln Leu Thr Leu Ala Pro
    1090                1095                1100

Gly Gln Leu Ile Leu Ile Arg Lys Lys Asn Pro Gly Gly Trp Trp Glu
1105                1110                1115                1120

Gly Glu Leu Gln Ala Arg Gly Lys Lys Arg Gln Ile Gly Trp Phe Pro
                1125                1130                1135

Ala Asn Tyr Val Lys Leu Leu Ser Pro Gly Thr Ser Lys Ile Thr Pro
            1140                1145                1150

Thr Glu Pro Pro Lys Ser Thr Ala Leu Ala Ala Val Cys Gln Val Ile
        1155                1160                1165

Gly Met Tyr Asp Tyr Thr Ala Gln Asn Asp Asp Glu Leu Ala Phe Asn
    1170                1175                1180

Lys Gly Gln Ile Ile Asn Val Leu Asn Lys Glu Asp Pro Asp Trp Trp
1185                1190                1195                1200

Lys Gly Glu Val Asn Gly Gln Val Gly Leu Phe Pro Ser Asn Tyr Val
                1205                1210                1215

Lys Leu Thr Thr Asp Met Asp Pro Ser Gln Gln
            1220                1225

<210> SEQ ID NO 9
<211> LENGTH: 10
<212> TYPE: PRT
<213> ORGANISM: Homo sapiens

<400> SEQUENCE: 9

Ile Ile Cys Cys Pro Ser Pro Pro Gln Ala
 1               5                  10

<210> SEQ ID NO 10
```

```
<211> LENGTH: 15
<212> TYPE: PRT
<213> ORGANISM: Homo sapiens

<400> SEQUENCE: 10

Lys Ser Ser Lys Arg Pro Thr Ile Pro Tyr His Cys Pro Glu Gly
  1               5                  10                  15

<210> SEQ ID NO 11
<211> LENGTH: 5
<212> TYPE: PRT
<213> ORGANISM: Homo sapiens

<400> SEQUENCE: 11

Trp Glu Met Gln Pro
  1               5

<210> SEQ ID NO 12
<211> LENGTH: 13
<212> TYPE: PRT
<213> ORGANISM: Homo sapiens

<400> SEQUENCE: 12

Ser Cys Asp Phe Gln His Asp His Leu Leu Pro Ser Glu
  1               5                  10

<210> SEQ ID NO 13
<211> LENGTH: 20
<212> TYPE: PRT
<213> ORGANISM: Homo sapiens

<400> SEQUENCE: 13

Lys Asn Ser Leu Gln Ser Ser Leu Pro His Phe Thr Leu Val Ala Cys
  1               5                  10                  15

Asp Arg Asn Val
             20

<210> SEQ ID NO 14
<211> LENGTH: 28
<212> TYPE: PRT
<213> ORGANISM: Homo sapiens

<400> SEQUENCE: 14

Val Ile Thr Cys Arg Asp Arg Ser Lys Asn Tyr Lys Asn Thr Gln Gly
  1               5                  10                  15

Ser Gly Ser Phe Cys Gly Phe Pro Ser Tyr Ser Asn
             20                  25

<210> SEQ ID NO 15
<211> LENGTH: 30
<212> TYPE: PRT
<213> ORGANISM: Homo sapiens

<400> SEQUENCE: 15

Leu Ser Pro Thr Phe Ala Gln Val Leu Ser Ile Val Leu Lys Leu Phe
  1               5                  10                  15

Leu Asn Ile Tyr Phe Ser Phe Leu Ile Asn Lys Ile Asn Lys
             20                  25                  30

<210> SEQ ID NO 16
<211> LENGTH: 20
<212> TYPE: PRT
<213> ORGANISM: Homo sapiens
```

```
<400> SEQUENCE: 16

Leu Leu Cys Tyr Phe Gly Phe Ala Lys Arg Pro Thr Ile Lys Glu Cys
 1               5                  10                  15

Cys Met Cys Tyr
            20

<210> SEQ ID NO 17
<211> LENGTH: 34
<212> TYPE: PRT
<213> ORGANISM: Homo sapiens

<400> SEQUENCE: 17

Lys Leu Phe Gln Met Ser Ile Asn Leu Arg Leu Asp Val Phe Phe His
 1               5                  10                  15

Phe Val Gln Cys Tyr Gln Leu Asn Cys Ala Val Trp Gly Phe Ser Pro
            20                  25                  30

Leu Pro

<210> SEQ ID NO 18
<211> LENGTH: 13
<212> TYPE: PRT
<213> ORGANISM: Homo sapiens

<400> SEQUENCE: 18

Lys Cys Arg Gly Val Gln Tyr Leu Cys Phe Lys Asp Val
 1               5                  10

<210> SEQ ID NO 19
<211> LENGTH: 4
<212> TYPE: PRT
<213> ORGANISM: Homo sapiens

<400> SEQUENCE: 19

Asn Glu Pro Asn
 1

<210> SEQ ID NO 20
<211> LENGTH: 15
<212> TYPE: PRT
<213> ORGANISM: Homo sapiens

<400> SEQUENCE: 20

Ser Glu Gly Val Cys Ala Cys Leu Cys Val Ser Ala Val Pro Cys
 1               5                  10                  15

<210> SEQ ID NO 21
<211> LENGTH: 7
<212> TYPE: PRT
<213> ORGANISM: Homo sapiens

<400> SEQUENCE: 21

Ala Cys Asn Thr Ser Cys Thr
 1               5

<210> SEQ ID NO 22
<211> LENGTH: 29
<212> TYPE: PRT
<213> ORGANISM: Homo sapiens

<400> SEQUENCE: 22

Glu Ile Ser Ser Phe His Gly Lys Ala Ile Thr Leu Tyr Asp Ala Leu
 1               5                  10                  15
```

```
Ile Ile Leu His Leu Ile Leu Phe Cys Thr Val Thr Leu
            20                  25
```

<210> SEQ ID NO 23
<211> LENGTH: 33
<212> TYPE: PRT
<213> ORGANISM: Homo sapiens

<400> SEQUENCE: 23

```
Pro His Glu Lys Ala Leu Cys Val Phe Val Arg Ser Gln Ile Tyr Leu
 1               5                  10                  15

Val Glu Leu Val Phe Cys Leu Gly Phe Leu Ile Leu Arg Val Cys Ile
            20                  25                  30

Ala
```

<210> SEQ ID NO 24
<211> LENGTH: 2
<212> TYPE: PRT
<213> ORGANISM: Homo sapiens

<400> SEQUENCE: 24

```
Asn Gln
 1
```

<210> SEQ ID NO 25
<211> LENGTH: 16
<212> TYPE: PRT
<213> ORGANISM: Homo sapiens

<400> SEQUENCE: 25

```
Thr Thr Pro Leu Arg Ser Leu Arg Ser Thr Ile Ser Thr Val Ser Phe
 1               5                  10                  15
```

<210> SEQ ID NO 26
<211> LENGTH: 14
<212> TYPE: PRT
<213> ORGANISM: Homo sapiens

<400> SEQUENCE: 26

```
Ser Leu Leu His Glu Val Leu Phe Gln Leu Leu Phe Met Glu
 1               5                  10
```

<210> SEQ ID NO 27
<211> LENGTH: 5
<212> TYPE: PRT
<213> ORGANISM: Homo sapiens

<400> SEQUENCE: 27

```
Pro Ile Leu Asn Lys
 1               5
```

<210> SEQ ID NO 28
<211> LENGTH: 2
<212> TYPE: PRT
<213> ORGANISM: Homo sapiens

<400> SEQUENCE: 28

```
Phe Ser
 1
```

<210> SEQ ID NO 29
<211> LENGTH: 29
<212> TYPE: PRT
<213> ORGANISM: Homo sapiens

```
<400> SEQUENCE: 29

Gln Glu Arg Met Tyr Arg Ser Leu Pro Ala Ile Asn Phe Gln Cys Leu
1               5                   10                  15

His Phe Leu Thr Arg Leu Trp Asn Phe Tyr Arg Leu Ile
            20                  25

<210> SEQ ID NO 30
<211> LENGTH: 9
<212> TYPE: PRT
<213> ORGANISM: Homo sapiens

<400> SEQUENCE: 30

Asn Gly Ala His Gly Pro Phe Val Cys
1               5

<210> SEQ ID NO 31
<211> LENGTH: 4
<212> TYPE: PRT
<213> ORGANISM: Homo sapiens

<400> SEQUENCE: 31

Ile Cys Cys Ser
1

<210> SEQ ID NO 32
<211> LENGTH: 33
<212> TYPE: PRT
<213> ORGANISM: Homo sapiens

<400> SEQUENCE: 32

Ser Pro Val Cys Leu Leu Asn Thr Ser Trp Lys Leu Ser Ile Lys Met
1               5                   10                  15

Pro Ala Ala His Ser Thr Glu Asn Gly Ala Gly Gly Ala Ser Ser Thr
            20                  25                  30

Ile

<210> SEQ ID NO 33
<211> LENGTH: 3
<212> TYPE: PRT
<213> ORGANISM: Homo sapiens

<400> SEQUENCE: 33

Leu Ser Ser
1

<210> SEQ ID NO 34
<211> LENGTH: 50
<212> TYPE: PRT
<213> ORGANISM: Homo sapiens

<400> SEQUENCE: 34

Arg Leu Cys Asn Ala His Ser Pro Arg Val Leu Pro Ala Leu Ser Gly
1               5                   10                  15

Gly Cys Ala Gly Gly Arg Val Glu Val Leu Leu Leu Ser His Gly Ala
            20                  25                  30

Glu Ser Glu Asp Leu Ser Ser Ser Phe Ser Cys Thr Ser Val Phe Ser
        35                  40                  45

Arg Ile
    50
```

```
<210> SEQ ID NO 35
<211> LENGTH: 1
<212> TYPE: PRT
<213> ORGANISM: Homo sapiens

<400> SEQUENCE: 35

Met
 1

<210> SEQ ID NO 36
<211> LENGTH: 2
<212> TYPE: PRT
<213> ORGANISM: Homo sapiens

<400> SEQUENCE: 36

Asn Ile
 1

<210> SEQ ID NO 37
<211> LENGTH: 22
<212> TYPE: PRT
<213> ORGANISM: Homo sapiens

<400> SEQUENCE: 37

Ile Tyr Lys Pro Ala Ala Leu Thr Thr Val Ile Gln Pro Phe Glu Leu
 1               5                  10                  15

Val Pro Cys Ile Asp Asn
            20

<210> SEQ ID NO 38
<211> LENGTH: 12
<212> TYPE: PRT
<213> ORGANISM: Homo sapiens

<400> SEQUENCE: 38

Ile Leu His Thr Lys Val Lys Lys Lys Lys Lys Lys
 1               5                  10

<210> SEQ ID NO 39
<211> LENGTH: 5195
<212> TYPE: DNA
<213> ORGANISM: Homo sapiens

<400> SEQUENCE: 39
agagtggagg cgccagggga gggagcgtag cttggttgct ccgtagtacg gcggctcgcg       60
aggaagaatc ccgagcgggc tccgggacgg acagagaggc gggcggggat ggtgtgcggg      120
gctgcggctc ctgcgtccct cccagcggcg cgtgagcggc actgatttgt ccctggggcg      180
gcagcgcgga cccgcccgga gatgaggcgt cgattagcaa ggtaaaagta acagaaccat      240
ggctcagttt ccaacacctt ttggtggcag cctggatatc tgggccataa ctgtagagga      300
aagagcgaag catgatcagc agttccatag tttaaagcca atatctggat tcattactgg      360
tgatcaagct agaaactttt tttttcaatc tgggttacct caacctgttt tagcacagat      420
atgggcacta gctgacatga ataatgatgg aagaatggat caagtggagt tttccatagc      480
tatgaaactt atcaaactga agctacaagg atatcagcta ccctctgcac ttccccctgt      540
catgaaacag caaccagttg ctatttctag cgcaccagca tttggtatgg gaggtatcgc      600
cagcatgcca ccgcttacag ctgttgctcc agtgccaatg ggatccattc agttgttgg       660 aatgtctcca accctagtat cttctgttcc cacagcagct gtgccccccc tggctaacgg      720 ggctcccccct gttatacaac tctgcctgc atttgctcat cctgcagcca cattgccaaa      780
```

```
gagttcttcc tttagtagat ctggtccagg gtcacaacta aacactaaat tacaaaaggc    840
acagtcattt gatgtggcca gtgtcccacc agtggcagag tgggctgttc ctcagtcatc    900
aagactgaaa tacaggcaat tattcaatag tcatgacaaa actatgagtg acacttaac    960 aggtccccaa gcaagaacta ttcttatgca gtcaagttta ccacaggctc agctggcttc   1020
aatatggaat ctttctgaca ttgatcaaga tggaaaactt acagcagagg aatttatcct   1080
ggcaatgcac ctcattgatg tagctatgtc tggccaacca ctgccacctg tcctgcctcc   1140
agaatacatt ccaccttctt ttagaagagt tcgatctggc agtggtatat ctgtcataag   1200
ctcaacatct gtagatcaga ggctaccaga ggaaccagtt ttagaagatg aacaacaaca   1260
attagaaaag aaattacctg taacgtttga agataagaag cgggagaact ttgaacgtgg   1320
caacctggaa ctggagaaac gaaggcaagc tctcctggaa cagcagcgca aggagcagga   1380
gcgcctggcc cagctggagc gggcggagca ggagaggaag gagcgtgagc gccaggagca   1440
agagcgcaaa agacaactgg aactggagaa gcaactggaa agcagcggg agctagaacg   1500 gcagagagag gaggagagga ggaaagaaat tgagaggcga gaggctgcaa acgggaact    1560 tgaaaggcaa cgacaacttg agtgggaacg gaatcgaagg caagaactac taaatcaaag   1620
aaacaaagaa caagaggaca tagttgtact gaaagcaaag aaaaagactt tggaatttga   1680
attagaagct ctaaatgata aaaagcatca actagaaggg aaacttcaag atatcagatg   1740
tcgattgacc acccaaaggc aagaaattga gagcacaaac aaatctagag agttgagaat   1800
tgccgaaatc acccatctac agcaacaatt acaggaatct cagcaaatgc ttggaagact   1860
tattccagaa aaacagatac tcaatgacca attaaaacaa gttcagcaga acagtttgca   1920
cagagattca cttgttacac ttaaaagagc cttagaagca aaagaactag ctcggcagca   1980
cctacgagac caactggatg aagtggagaa agaaactaga tcaaaactac aggagattga   2040
tattttcaat aatcagctga aggaactaag agaaatacac aataagcaac aactccagaa   2100
gcaaaagtcc atggaggctg aacgactgaa acagaaagaa caagaacgaa agatcataga   2160
attgaaaaaa caaaagaag aagcccaaag acgagctcag gaaagggaca agcagtggct   2220
ggagcatgtg cagcaggagg acgagcatca gagaccaaga aaactccacg aagaggaaaa   2280
actgaaaagg gaggagagtg tcaaaagaa ggatggcgag gaaaaaggca acaggaagc    2340 acaagacaag ctgggtcggc ttttccatca acaccaagaa ccagctaagc cagctgtcca   2400
ggcaccctgg tccactgcag aaaaaggtcc acttaccatt tctgcacagg aaaatgtaaa   2460
agtggtgtat taccgggcac tgtaccccctt tgaatccaga agccatgatg aaatcactat   2520
ccagccagga gacatagtca tggtggatga agccaaaact ggagaacccg gctggcttgg   2580
aggagaatta aaaggaaaga cagggtggtt ccctgcaaac tatgcagaga aatcccaga    2640 aaatgaggtt cccgctccag tgaaaccagt gactgattca acatctgccc ctgcccccaa   2700
actggccttg cgtgagaccc ccgccccttt ggcagtaacc tcttcagagc cctccacgac   2760
ccctaataac tgggccgact tcagctccac gtgcccacc agcacgaatg agaaaccaga   2820
aacggataac tgggatgcat gggcagccca gccctctctc accgttccaa gtgccggcca   2880
gttaaggcag aggtccgcct ttactccagc cacggccact ggctcctccc cgtctcctgt   2940
gctaggccag ggtgaaaagg tggaggggct acaagctcaa gccctatatc cttggagagc   3000
caaaaaagac aaccacttaa attttaacaa aaatgatgtc atcaccgtcc tggaacagca   3060
agacatgtgg tggtttggag aagttcaagg tcagaagggt tggttcccca gtcttacgt    3120
```

```
gaaactcatt tcagggccca taaggaagtc tacaagcatg gattctggtt cttcagagag     3180
tcctgctagt ctaaagcgag tagcctctcc agcagccaag ccggtcgttt cgggagaaga     3240
atttattgcc atgtacactt acgagagttc tgagcaagga gatttaacct ttcagcaagg     3300
ggatgtgatt ttggttacca agaaagatgg tgactggtgg acaggaacag tgggcgacaa     3360
ggccggagtc ttcccttcta actatgtgag gcttaaagat tcagagggct ctggaactgc     3420
tgggaaaaca gggagtttag gaaaaaaacc tgaaattgcc caggttattg cctcatacac     3480
cgccaccggc cccgagcagc tcactctcgc ccctggtcag ctgattttga tccgaaaaaa     3540
gaacccaggt ggatggtggg aaggagagct gcaagcacgt gggaaaaagc gccagatagg     3600
ctggttccca gctaattatg taaagcttct aagccctggg acgagcaaaa tcactccaac     3660
agagccacct aagtcaacag cattagcggc agtgtgccag gtgattggga tgtacgacta     3720
caccgcgcag aatgacgatg agctggcctt caacaagggc cagatcatca acgtcctcaa     3780
caaggaggac cctgactggt ggaaggagaa gtcaatggaa caagtggggc tcttcccatc     3840
caattatgtg aagctgacca cagacatgga cccaagccag caatgaatca tatgttgtcc     3900
atccccccct caggcttgaa agtccttttg tggctttcct agttactcaa attgactttc     3960
ccccaccttt gcacaggtgc tttcaatagt tttaaaatta ttttttaaata tatattttag     4020
ctttttaata aacaaaataa ataaatgact tctttgctat tttggttttg caaaagacc      4080
cactatcaag gaatgctgca tgtgctatta aaaattgttc caaatgtcca taaatctgag     4140
acttgatgta tttttcatt ttgtccagtg ttaccaacta aattgtgcag tttggggctt      4200
ttcccccctta ccatagaagt gcagaggagt tcagtatctc tgttttaaag acgtatagaa    4260
tgagcccaat taaagcgaag gtgtttgtgc ttgtttgtgt gtatcagctg taccttgttg     4320
agcatgtaat acatcctgta cataagaaat tagttctttc catggcaaag ctattacctt     4380
gtacgatgct ctaatcatat tgcatttaat tttattttgc acagtgacct tgtagccaca     4440
tgagaaagca ctctgtgttt tgttcggtc tcagatttat ctggttgagt tggtgttttg      4500
tttgggtttt ttaattttgc gtgtttgcat agcataaaat cagtagacaa caccactgag    4560
gtcgttacga tcaacgatat ccacagtctc tttttagtct ctgttacatg aagttttatt    4620
ccagttactt ttcatggaat gacctatttt gaacaagtaa ttttcttgac aagaaagaat    4680
gtatagaagt ctccctgcaa ttaatttcca atgtttacat ttttttaacta gactgtggaa   4740
tttctacaga ttaatatgaa atggagctca tggtccgttt gtgtgttaga tatgctgtag    4800
ctgaagccct gtttgtcttt taaacactag ttggaagctc tcaataaaaa tgcctgctgc    4860
tcacagcaca gaaaatgggg caggggagc ctcaagcaca atctagctgt cctcctaaag    4920
actctgtaat gctcactccc ctcgcgttct cccggcgctg tcgggaggct gtgctggtgg    4980
tcgtgtagag gtccttctcc tttcacatgg tgcagagagc gaggacctct cctcctcgtt     5040
cagttgcact tcagtatttt cacgatatg aatgtaaaat atataaatat ataaacctgc     5100
ggctttaaca actgtaatac aacctttga attagttccg tgtatagata attaaattct     5160
tcatacaaaa gttaaaaaaa aaaaaaaaaa aaaaa                                5195
```

<210> SEQ ID NO 40
<211> LENGTH: 1215
<212> TYPE: PRT
<213> ORGANISM: Homo sapiens

<400> SEQUENCE: 40

Met Ala Gln Phe Pro Thr Pro Phe Gly Gly Ser Leu Asp Ile Trp Ala

```
  1               5                   10                  15
Ile Thr Val Glu Glu Arg Ala Lys His Asp Gln Gln Phe His Ser Leu
             20                  25                  30

Lys Pro Ile Ser Gly Phe Ile Thr Gly Asp Gln Ala Arg Asn Phe Phe
             35                  40                  45

Phe Gln Ser Gly Leu Pro Gln Pro Val Leu Ala Gln Ile Trp Ala Leu
 50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
                100                 105                 110

Pro Ala Phe Gly Met Gly Ile Ala Ser Met Pro Pro Leu Thr Ala
                115                 120                 125

Val Ala Pro Val Pro Met Gly Ser Ile Pro Val Val Gly Met Ser Pro
     130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                 165                 170                 175

Ala Thr Leu Pro Lys Ser Ser Ser Phe Ser Arg Ser Gly Pro Gly Ser
                 180                 185                 190

Gln Leu Asn Thr Lys Leu Gln Lys Ala Gln Ser Phe Asp Val Ala Ser
         195                 200                 205

Val Pro Pro Val Ala Glu Trp Ala Val Pro Gln Ser Ser Arg Leu Lys
     210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                 245                 250                 255

Ala Gln Leu Ala Ser Ile Trp Asn Leu Ser Asp Ile Asp Gln Asp Gly
                 260                 265                 270

Lys Leu Thr Ala Glu Glu Phe Ile Leu Ala Met His Leu Ile Asp Val
             275                 280                 285

Ala Met Ser Gly Gln Pro Leu Pro Pro Val Leu Pro Pro Glu Tyr Ile
         290                 295                 300

Pro Pro Ser Phe Arg Arg Val Arg Ser Gly Ser Gly Ile Ser Val Ile
305                 310                 315                 320

Ser Ser Thr Ser Val Asp Gln Arg Leu Pro Glu Glu Pro Val Leu Glu
                 325                 330                 335

Asp Glu Gln Gln Gln Leu Glu Lys Lys Leu Pro Val Thr Phe Glu Asp
                 340                 345                 350

Lys Lys Arg Glu Asn Phe Glu Arg Gly Asn Leu Glu Leu Glu Lys Arg
             355                 360                 365

Arg Gln Ala Leu Leu Glu Gln Arg Lys Glu Gln Glu Arg Leu Ala
     370                 375                 380

Gln Leu Glu Arg Ala Glu Gln Glu Arg Lys Glu Arg Glu Arg Gln Glu
385                 390                 395                 400

Gln Glu Arg Lys Arg Gln Leu Glu Leu Glu Lys Gln Leu Glu Lys Gln
                         405                 410                 415

Arg Glu Leu Glu Arg Gln Arg Glu Glu Glu Arg Arg Lys Glu Ile Glu
             420                 425                 430
```

-continued

```
Arg Arg Glu Ala Ala Lys Arg Glu Leu Glu Arg Gln Arg Gln Leu Glu
        435                 440                 445

Trp Glu Arg Asn Arg Arg Gln Glu Leu Leu Asn Gln Arg Asn Lys Glu
    450                 455                 460

Gln Glu Asp Ile Val Val Leu Lys Ala Lys Lys Thr Leu Glu Phe
465                 470                 475                 480

Glu Leu Glu Ala Leu Asn Asp Lys Lys His Gln Leu Glu Gly Lys Leu
                485                 490                 495

Gln Asp Ile Arg Cys Arg Leu Thr Thr Gln Arg Gln Glu Ile Glu Ser
            500                 505                 510

Thr Asn Lys Ser Arg Glu Leu Arg Ile Ala Glu Ile Thr His Leu Gln
        515                 520                 525

Gln Gln Leu Gln Glu Ser Gln Gln Met Leu Gly Arg Leu Ile Pro Glu
    530                 535                 540

Lys Gln Ile Leu Asn Asp Gln Leu Lys Gln Val Gln Gln Asn Ser Leu
545                 550                 555                 560

His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
            580                 585                 590

Thr Arg Ser Lys Leu Gln Glu Ile Asp Ile Phe Asn Asn Gln Leu Lys
        595                 600                 605

Glu Leu Arg Glu Ile His Asn Lys Gln Gln Leu Gln Lys Gln Lys Ser
    610                 615                 620

Met Glu Ala Glu Arg Leu Lys Gln Lys Glu Gln Glu Arg Lys Ile Ile
625                 630                 635                 640

Glu Leu Glu Lys Gln Lys Glu Glu Ala Gln Arg Arg Ala Gln Glu Arg
                645                 650                 655

Asp Lys Gln Trp Leu Glu His Val Gln Gln Glu Asp Glu His Gln Arg
            660                 665                 670

Pro Arg Lys Leu His Glu Glu Lys Leu Lys Arg Glu Glu Ser Val
        675                 680                 685

Lys Lys Lys Asp Gly Glu Glu Lys Gly Lys Gln Glu Ala Gln Asp Lys
    690                 695                 700

Leu Gly Arg Leu Phe His Gln His Gln Glu Pro Ala Lys Pro Ala Val
705                 710                 715                 720

Gln Ala Pro Trp Ser Thr Ala Glu Lys Gly Pro Leu Thr Ile Ser Ala
                725                 730                 735

Gln Glu Asn Val Lys Val Val Tyr Tyr Arg Ala Leu Tyr Pro Phe Glu
            740                 745                 750

Ser Arg Ser His Asp Glu Ile Thr Ile Gln Pro Gly Asp Ile Val Met
        755                 760                 765

Val Asp Glu Ser Gln Thr Gly Glu Pro Gly Trp Leu Gly Gly Glu Leu
    770                 775                 780

Lys Gly Lys Thr Gly Trp Phe Pro Ala Asn Tyr Ala Glu Lys Ile Pro
785                 790                 795                 800

Glu Asn Glu Val Pro Ala Pro Val Lys Pro Val Thr Asp Ser Thr Ser
                805                 810                 815

Ala Pro Ala Pro Lys Leu Ala Leu Arg Glu Thr Pro Ala Pro Leu Ala
            820                 825                 830

Val Thr Ser Ser Glu Pro Ser Thr Thr Pro Asn Asn Trp Ala Asp Phe
        835                 840                 845
```

-continued

Ser Ser Thr Trp Pro Thr Ser Thr Asn Glu Lys Pro Glu Thr Asp Asn
    850                 855                 860

Trp Asp Ala Trp Ala Ala Gln Pro Ser Leu Thr Val Pro Ser Ala Gly
865                 870                 875                 880

Gln Leu Arg Gln Arg Ser Ala Phe Thr Pro Ala Thr Ala Thr Gly Ser
                885                 890                 895

Ser Pro Ser Pro Val Leu Gly Gln Gly Glu Lys Val Glu Gly Leu Gln
            900                 905                 910

Ala Gln Ala Leu Tyr Pro Trp Arg Ala Lys Lys Asp Asn His Leu Asn
        915                 920                 925

Phe Asn Lys Asn Asp Val Ile Thr Val Leu Glu Gln Gln Asp Met Trp
    930                 935                 940

Trp Phe Gly Glu Val Gln Gly Gln Lys Gly Trp Phe Pro Lys Ser Tyr
945                 950                 955                 960

Val Lys Leu Ile Ser Gly Pro Ile Arg Lys Ser Thr Ser Met Asp Ser
                965                 970                 975

Gly Ser Ser Glu Ser Pro Ala Ser Leu Lys Arg Val Ala Ser Pro Ala
            980                 985                 990

Ala Lys Pro Val Val Ser Gly Glu Glu Phe Ile Ala Met Tyr Thr Tyr
        995                 1000                1005

Glu Ser Ser Glu Gln Gly Asp Leu Thr Phe Gln Gln Gly Asp Val Ile
    1010                1015                1020

Leu Val Thr Lys Lys Asp Gly Asp Trp Trp Thr Gly Thr Val Gly Asp
1025                1030                1035                1040

Lys Ala Gly Val Phe Pro Ser Asn Tyr Val Arg Leu Lys Asp Ser Glu
                1045                1050                1055

Gly Ser Gly Thr Ala Gly Lys Thr Gly Ser Leu Gly Lys Lys Pro Glu
            1060                1065                1070

Ile Ala Gln Val Ile Ala Ser Tyr Thr Ala Thr Gly Pro Glu Gln Leu
        1075                1080                1085

Thr Leu Ala Pro Gly Gln Leu Ile Leu Ile Arg Lys Lys Asn Pro Gly
    1090                1095                1100

Gly Trp Trp Glu Gly Glu Leu Gln Ala Arg Gly Lys Lys Arg Gln Ile
1105                1110                1115                1120

Gly Trp Phe Pro Ala Asn Tyr Val Lys Leu Leu Ser Pro Gly Thr Ser
                1125                1130                1135

Lys Ile Thr Pro Thr Glu Pro Pro Lys Ser Thr Ala Leu Ala Ala Val
            1140                1145                1150

Cys Gln Val Ile Gly Met Tyr Asp Tyr Thr Ala Gln Asn Asp Asp Glu
        1155                1160                1165

Leu Ala Phe Asn Lys Gly Gln Ile Ile Asn Val Leu Asn Lys Glu Asp
    1170                1175                1180

Pro Asp Trp Trp Lys Gly Glu Val Asn Gly Gln Val Gly Leu Phe Pro
1185                1190                1195                1200

Ser Asn Tyr Val Lys Leu Thr Thr Asp Met Asp Pro Ser Gln Gln
                1205                1210                1215

<210> SEQ ID NO 41
<211> LENGTH: 14
<212> TYPE: PRT
<213> ORGANISM: Homo sapiens
<220> FEATURE:
<223> OTHER INFORMATION: From Seq ID 41 to ID 70, there are 30 pretein
      sequences translated from Seq ID No. 6. Together,
      they form the whole protein sequence.

```
<400> SEQUENCE: 41

Glu Trp Arg Arg Gln Gly Arg Glu Arg Ser Leu Val Ala Pro
  1               5                  10

<210> SEQ ID NO 42
<211> LENGTH: 52
<212> TYPE: PRT
<213> ORGANISM: Homo sapiens

<400> SEQUENCE: 42

Tyr Gly Gly Ser Arg Gly Arg Ile Pro Ser Gly Leu Arg Asp Gly Gln
  1               5                  10                  15

Arg Gly Gly Arg Gly Trp Cys Ala Gly Leu Arg Leu Leu Arg Pro Ser
                 20                  25                  30

Gln Arg Arg Val Ser Gly Thr Asp Leu Ser Leu Gly Arg Gln Arg Gly
             35                  40                  45

Pro Ala Arg Arg
         50

<210> SEQ ID NO 43
<211> LENGTH: 3
<212> TYPE: PRT
<213> ORGANISM: Homo sapiens

<400> SEQUENCE: 43

Gly Val Asp
  1

<210> SEQ ID NO 44
<211> LENGTH: 1222
<212> TYPE: PRT
<213> ORGANISM: Homo sapiens

<400> SEQUENCE: 44

Gln Gly Lys Ser Asn Arg Thr Met Ala Gln Phe Pro Thr Pro Phe Gly
  1               5                  10                  15

Gly Ser Leu Asp Ile Trp Ala Ile Thr Val Glu Glu Arg Ala Lys His
                 20                  25                  30

Asp Gln Gln Phe His Ser Leu Lys Pro Ile Ser Gly Phe Ile Thr Gly
             35                  40                  45

Asp Gln Ala Arg Asn Phe Phe Phe Gln Ser Gly Leu Pro Gln Pro Val
         50                  55                  60

Leu Ala Gln Ile Trp Ala Leu Ala Asp Met Asn Asn Asp Gly Arg Met
 65                  70                  75                  80

Asp Gln Val Glu Phe Ser Ile Ala Met Lys Leu Ile Lys Leu Lys Leu
                 85                  90                  95

Gln Gly Tyr Gln Leu Pro Ser Ala Leu Pro Pro Val Met Lys Gln Gln
                100                 105                 110

Pro Val Ala Ile Ser Ser Ala Pro Ala Phe Gly Met Gly Gly Ile Ala
            115                 120                 125

Ser Met Pro Pro Leu Thr Ala Val Ala Pro Val Pro Met Gly Ser Ile
        130                 135                 140

Pro Val Val Gly Met Ser Pro Thr Leu Val Ser Ser Val Pro Thr Ala
145                 150                 155                 160

Ala Val Pro Pro Leu Ala Asn Gly Ala Pro Pro Val Ile Gln Pro Leu
                165                 170                 175

Pro Ala Phe Ala His Pro Ala Ala Thr Leu Pro Lys Ser Ser Ser Phe
            180                 185                 190
```

```
Ser Arg Ser Gly Pro Gly Ser Gln Leu Asn Thr Lys Leu Gln Lys Ala
            195                 200                 205

Gln Ser Phe Asp Val Ala Ser Val Pro Val Ala Glu Trp Ala Val
        210                 215                 220

Pro Gln Ser Ser Arg Leu Lys Tyr Arg Gln Leu Phe Asn Ser His Asp
225                 230                 235                 240

Lys Thr Met Ser Gly His Leu Thr Gly Pro Gln Ala Arg Thr Ile Leu
                245                 250                 255

Met Gln Ser Ser Leu Pro Gln Ala Gln Leu Ala Ser Ile Trp Asn Leu
            260                 265                 270

Ser Asp Ile Asp Gln Asp Gly Lys Leu Thr Ala Glu Glu Phe Ile Leu
        275                 280                 285

Ala Met His Leu Ile Asp Val Ala Met Ser Gly Gln Pro Leu Pro Pro
290                 295                 300

Val Leu Pro Pro Glu Tyr Ile Pro Pro Ser Phe Arg Arg Val Arg Ser
305                 310                 315                 320

Gly Ser Gly Ile Ser Val Ile Ser Ser Thr Ser Val Asp Gln Arg Leu
                325                 330                 335

Pro Glu Glu Pro Val Leu Glu Asp Glu Gln Gln Gln Leu Glu Lys Lys
            340                 345                 350

Leu Pro Val Thr Phe Glu Asp Lys Lys Arg Glu Asn Phe Glu Arg Gly
        355                 360                 365

Asn Leu Glu Leu Glu Lys Arg Arg Gln Ala Leu Leu Glu Gln Gln Arg
370                 375                 380

Lys Glu Gln Glu Arg Leu Ala Gln Leu Glu Arg Ala Glu Gln Glu Arg
385                 390                 395                 400

Lys Glu Arg Glu Arg Gln Glu Gln Glu Arg Lys Arg Gln Leu Glu Leu
                405                 410                 415

Glu Lys Gln Leu Glu Lys Gln Arg Glu Leu Glu Arg Gln Arg Glu Glu
            420                 425                 430

Glu Arg Arg Lys Glu Ile Glu Arg Arg Glu Ala Ala Lys Arg Glu Leu
        435                 440                 445

Glu Arg Gln Arg Gln Leu Glu Trp Glu Arg Asn Arg Arg Gln Glu Leu
450                 455                 460

Leu Asn Gln Arg Asn Lys Glu Gln Glu Asp Ile Val Val Leu Lys Ala
465                 470                 475                 480

Lys Lys Lys Thr Leu Glu Phe Glu Leu Glu Ala Leu Asn Asp Lys Lys
                485                 490                 495

His Gln Leu Glu Gly Lys Leu Gln Asp Ile Arg Cys Arg Leu Thr Thr
            500                 505                 510

Gln Arg Gln Glu Ile Glu Ser Thr Asn Lys Ser Arg Glu Leu Arg Ile
        515                 520                 525

Ala Glu Ile Thr His Leu Gln Gln Gln Leu Gln Glu Ser Gln Gln Met
530                 535                 540

Leu Gly Arg Leu Ile Pro Glu Lys Gln Ile Leu Asn Asp Gln Leu Lys
545                 550                 555                 560

Gln Val Gln Gln Asn Ser Leu His Arg Asp Ser Leu Val Thr Leu Lys
                565                 570                 575

Arg Ala Leu Glu Ala Lys Glu Leu Ala Arg Gln His Leu Arg Asp Gln
            580                 585                 590

Leu Asp Glu Val Glu Lys Glu Thr Arg Ser Lys Leu Gln Glu Ile Asp
        595                 600                 605
```

```
Ile Phe Asn Asn Gln Leu Lys Glu Leu Arg Glu Ile His Asn Lys Gln
610                 615                 620
Gln Leu Gln Lys Gln Lys Ser Met Glu Ala Glu Arg Leu Lys Gln Lys
625                 630                 635                 640
Glu Gln Glu Arg Lys Ile Ile Glu Leu Glu Lys Gln Lys Glu Glu Ala
                645                 650                 655
Gln Arg Arg Ala Gln Glu Arg Asp Lys Gln Trp Leu Glu His Val Gln
            660                 665                 670
Gln Glu Asp Glu His Gln Arg Pro Arg Lys Leu His Glu Glu Glu Lys
            675                 680                 685
Leu Lys Arg Glu Glu Ser Val Lys Lys Asp Gly Glu Glu Lys Gly
690                 695                 700
Lys Gln Glu Ala Gln Asp Lys Leu Gly Arg Leu Phe His Gln His Gln
705                 710                 715                 720
Glu Pro Ala Lys Pro Ala Val Gln Ala Pro Trp Ser Thr Ala Glu Lys
                725                 730                 735
Gly Pro Leu Thr Ile Ser Ala Gln Glu Asn Val Lys Val Val Tyr Tyr
            740                 745                 750
Arg Ala Leu Tyr Pro Phe Glu Ser Arg Ser His Asp Glu Ile Thr Ile
            755                 760                 765
Gln Pro Gly Asp Ile Val Met Val Asp Glu Ser Gln Thr Gly Glu Pro
770                 775                 780
Gly Trp Leu Gly Gly Glu Leu Lys Gly Lys Thr Gly Trp Phe Pro Ala
785                 790                 795                 800
Asn Tyr Ala Glu Lys Ile Pro Glu Asn Glu Val Pro Ala Pro Val Lys
                805                 810                 815
Pro Val Thr Asp Ser Thr Ser Ala Pro Ala Pro Lys Leu Ala Leu Arg
            820                 825                 830
Glu Thr Pro Ala Pro Leu Ala Val Thr Ser Ser Glu Pro Ser Thr Thr
            835                 840                 845
Pro Asn Asn Trp Ala Asp Phe Ser Ser Thr Trp Pro Thr Ser Thr Asn
850                 855                 860
Glu Lys Pro Glu Thr Asp Asn Trp Asp Ala Trp Ala Ala Gln Pro Ser
865                 870                 875                 880
Leu Thr Val Pro Ser Ala Gly Gln Leu Arg Gln Arg Ser Ala Phe Thr
                885                 890                 895
Pro Ala Thr Ala Thr Gly Ser Ser Pro Ser Pro Val Leu Gly Gln Gly
            900                 905                 910
Glu Lys Val Glu Gly Leu Gln Ala Gln Ala Leu Tyr Pro Trp Arg Ala
            915                 920                 925
Lys Lys Asp Asn His Leu Asn Phe Asn Lys Asn Asp Val Ile Thr Val
930                 935                 940
Leu Glu Gln Gln Asp Met Trp Trp Phe Gly Glu Val Gln Gly Gln Lys
945                 950                 955                 960
Gly Trp Phe Pro Lys Ser Tyr Val Lys Leu Ile Ser Gly Pro Ile Arg
                965                 970                 975
Lys Ser Thr Ser Met Asp Ser Gly Ser Ser Glu Ser Pro Ala Ser Leu
            980                 985                 990
Lys Arg Val Ala Ser Pro Ala Ala Lys Pro Val Val Ser Gly Glu Glu
            995                 1000                1005
Phe Ile Ala Met Tyr Thr Tyr Glu Ser Ser Glu Gln Gly Asp Leu Thr
    1010                1015                1020
Phe Gln Gln Gly Asp Val Ile Leu Val Thr Lys Lys Asp Gly Asp Trp
```

```
                1025                1030                1035                1040
Trp Thr Gly Thr Val Gly Asp Lys Ala Gly Val Phe Pro Ser Asn Tyr
                    1045                1050                1055
Val Arg Leu Lys Asp Ser Glu Gly Ser Gly Thr Ala Gly Lys Thr Gly
                1060                1065                1070
Ser Leu Gly Lys Lys Pro Glu Ile Ala Gln Val Ile Ala Ser Tyr Thr
            1075                1080                1085
Ala Thr Gly Pro Glu Gln Leu Thr Leu Ala Pro Gly Gln Leu Ile Leu
        1090                1095                1100
Ile Arg Lys Lys Asn Pro Gly Gly Trp Trp Glu Gly Glu Leu Gln Ala
1105                1110                1115                1120
Arg Gly Lys Lys Arg Gln Ile Gly Trp Phe Pro Ala Asn Tyr Val Lys
                1125                1130                1135
Leu Leu Ser Pro Gly Thr Ser Lys Ile Thr Pro Thr Glu Pro Pro Lys
            1140                1145                1150
Ser Thr Ala Leu Ala Ala Val Cys Gln Val Ile Gly Met Tyr Asp Tyr
        1155                1160                1165
Thr Ala Gln Asn Asp Asp Glu Leu Ala Phe Asn Lys Gly Gln Ile Ile
    1170                1175                1180
Asn Val Leu Asn Lys Glu Asp Pro Asp Trp Trp Lys Gly Glu Val Asn
1185                1190                1195                1200
Gly Gln Val Gly Leu Phe Pro Ser Asn Tyr Val Lys Leu Thr Thr Asp
                1205                1210                1215
Met Asp Pro Ser Gln Gln
        1220
```

<210> SEQ ID NO 45
<211> LENGTH: 10
<212> TYPE: PRT
<213> ORGANISM: Homo sapiens

<400> SEQUENCE: 45

```
Ile Ile Cys Cys Pro Ser Pro Pro Gln Ala
1               5                   10
```

<210> SEQ ID NO 46
<211> LENGTH: 11
<212> TYPE: PRT
<213> ORGANISM: Homo sapiens

<400> SEQUENCE: 46

```
Lys Ser Phe Cys Gly Phe Pro Ser Tyr Ser Asn
1               5                   10
```

<210> SEQ ID NO 47
<211> LENGTH: 30
<212> TYPE: PRT
<213> ORGANISM: Homo sapiens

<400> SEQUENCE: 47

```
Leu Ser Pro Thr Phe Ala Gln Val Leu Ser Ile Val Leu Lys Leu Phe
1               5                   10                  15
Leu Asn Ile Tyr Phe Ser Phe Leu Ile Asn Lys Ile Asn Lys
            20                  25                  30
```

<210> SEQ ID NO 48
<211> LENGTH: 20
<212> TYPE: PRT
<213> ORGANISM: Homo sapiens -continued

```
<400> SEQUENCE: 48

Leu Leu Cys Tyr Phe Gly Phe Ala Lys Arg Pro Thr Ile Lys Glu Cys
 1               5                  10                  15

Cys Met Cys Tyr
            20

<210> SEQ ID NO 49
<211> LENGTH: 34
<212> TYPE: PRT
<213> ORGANISM: Homo sapiens

<400> SEQUENCE: 49

Lys Leu Phe Gln Met Ser Ile Asn Leu Arg Leu Asp Val Phe Phe His
 1               5                  10                  15

Phe Val Gln Cys Tyr Gln Leu Asn Cys Ala Val Trp Gly Phe Ser Pro
             20                  25                  30

Leu Pro

<210> SEQ ID NO 50
<211> LENGTH: 13
<212> TYPE: PRT
<213> ORGANISM: Homo sapiens

<400> SEQUENCE: 50

Lys Cys Arg Gly Val Gln Tyr Leu Cys Phe Lys Asp Val
 1               5                  10

<210> SEQ ID NO 51
<211> LENGTH: 4
<212> TYPE: PRT
<213> ORGANISM: Homo sapiens

<400> SEQUENCE: 51

Asn Glu Pro Asn
 1

<210> SEQ ID NO 52
<211> LENGTH: 15
<212> TYPE: PRT
<213> ORGANISM: Homo sapiens

<400> SEQUENCE: 52

Ser Glu Gly Val Cys Ala Cys Leu Cys Val Ser Ala Val Pro Cys
 1               5                  10                  15

<210> SEQ ID NO 53
<211> LENGTH: 7
<212> TYPE: PRT
<213> ORGANISM: Homo sapiens

<400> SEQUENCE: 53

Ala Cys Asn Thr Ser Cys Thr
 1               5

<210> SEQ ID NO 54
<211> LENGTH: 29
<212> TYPE: PRT
<213> ORGANISM: Homo sapiens

<400> SEQUENCE: 54

Glu Ile Ser Ser Phe His Gly Lys Ala Ile Thr Leu Tyr Asp Ala Leu
 1               5                  10                  15
```

Ile Ile Leu His Leu Ile Leu Phe Cys Thr Val Thr Leu
            20                  25

<210> SEQ ID NO 55
<211> LENGTH: 33
<212> TYPE: PRT
<213> ORGANISM: Homo sapiens

<400> SEQUENCE: 55

Pro His Glu Lys Ala Leu Cys Val Phe Val Arg Ser Gln Ile Tyr Leu
1               5                   10                  15

Val Glu Leu Val Phe Cys Leu Gly Phe Leu Ile Leu Arg Val Cys Ile
            20                  25                  30

Ala

<210> SEQ ID NO 56
<211> LENGTH: 2
<212> TYPE: PRT
<213> ORGANISM: Homo sapiens

<400> SEQUENCE: 56

Asn Gln
1

<210> SEQ ID NO 57
<211> LENGTH: 16
<212> TYPE: PRT
<213> ORGANISM: Homo sapiens

<400> SEQUENCE: 57

Thr Thr Pro Leu Arg Ser Leu Arg Ser Thr Ile Ser Thr Val Ser Phe
1               5                   10                  15

<210> SEQ ID NO 58
<211> LENGTH: 14
<212> TYPE: PRT
<213> ORGANISM: Homo sapiens

<400> SEQUENCE: 58

Ser Leu Leu His Glu Val Leu Phe Gln Leu Leu Phe Met Glu
1               5                   10

<210> SEQ ID NO 59
<211> LENGTH: 5
<212> TYPE: PRT
<213> ORGANISM: Homo sapiens

<400> SEQUENCE: 59

Pro Ile Leu Asn Lys
1               5

<210> SEQ ID NO 60
<211> LENGTH: 2
<212> TYPE: PRT
<213> ORGANISM: Homo sapiens

<400> SEQUENCE: 60

Phe Ser
1

<210> SEQ ID NO 61
<211> LENGTH: 29
<212> TYPE: PRT

<213> ORGANISM: Homo sapiens

<400> SEQUENCE: 61

Gln Glu Arg Met Tyr Arg Ser Leu Pro Ala Ile Asn Phe Gln Cys Leu
1               5                   10                  15

His Phe Leu Thr Arg Leu Trp Asn Phe Tyr Arg Leu Ile
            20                  25

<210> SEQ ID NO 62
<211> LENGTH: 9
<212> TYPE: PRT
<213> ORGANISM: Homo sapiens

<400> SEQUENCE: 62

Asn Gly Ala His Gly Pro Phe Val Cys
1               5

<210> SEQ ID NO 63
<211> LENGTH: 4
<212> TYPE: PRT
<213> ORGANISM: Homo sapiens

<400> SEQUENCE: 63

Ile Cys Cys Ser
1

<210> SEQ ID NO 64
<211> LENGTH: 33
<212> TYPE: PRT
<213> ORGANISM: Homo sapiens

<400> SEQUENCE: 64

Ser Pro Val Cys Leu Leu Asn Thr Ser Trp Lys Leu Ser Ile Lys Met
1               5                   10                  15

Pro Ala Ala His Ser Thr Glu Asn Gly Ala Gly Gly Ala Ser Ser Thr
            20                  25                  30

Ile

<210> SEQ ID NO 65
<211> LENGTH: 3
<212> TYPE: PRT
<213> ORGANISM: Homo sapiens

<400> SEQUENCE: 65

Leu Ser Ser
1

<210> SEQ ID NO 66
<211> LENGTH: 50
<212> TYPE: PRT
<213> ORGANISM: Homo sapiens

<400> SEQUENCE: 66

Arg Leu Cys Asn Ala His Ser Pro Arg Val Leu Pro Ala Leu Ser Gly
1               5                   10                  15

Gly Cys Ala Gly Gly Arg Val Glu Val Leu Leu Leu Ser His Gly Ala
            20                  25                  30

Glu Ser Glu Asp Leu Ser Ser Ser Phe Ser Cys Thr Ser Val Phe Ser
            35                  40                  45

Arg Ile
    50

```
<210> SEQ ID NO 67
<211> LENGTH: 1
<212> TYPE: PRT
<213> ORGANISM: Homo sapiens

<400> SEQUENCE: 67

Met
 1

<210> SEQ ID NO 68
<211> LENGTH: 2
<212> TYPE: PRT
<213> ORGANISM: Homo sapiens

<400> SEQUENCE: 68

Asn Ile
 1

<210> SEQ ID NO 69
<211> LENGTH: 22
<212> TYPE: PRT
<213> ORGANISM: Homo sapiens

<400> SEQUENCE: 69

Ile Tyr Lys Pro Ala Ala Leu Thr Thr Val Ile Gln Pro Phe Glu Leu
 1               5                  10                  15

Val Pro Cys Ile Asp Asn
            20

<210> SEQ ID NO 70
<211> LENGTH: 13
<212> TYPE: PRT
<213> ORGANISM: Homo sapiens

<400> SEQUENCE: 70

Ile Leu His Thr Lys Val Lys Lys Lys Lys Lys Lys Lys
 1               5                  10

<210> SEQ ID NO 71
<211> LENGTH: 2079
<212> TYPE: DNA
<213> ORGANISM: Homo sapiens

<400> SEQUENCE: 71
cggggatggt gtgcggggct gcggctcctg cgtccctccc agcggcgcgt gagcggcact      60
gatttgtccc tggggcggca gcgcggaccc gcccggagat gaggcgtcga ttagcaaggt     120
aaaagtaaca gaaccatggc tcagtttcca cacctttttg gtggcagcct ggatatctgg     180
gccataactg tagaggaaag agcgaagcat gatcagcagt tccatagttt aaagccaata     240
tctggattca ttactggtga tcaagctaga aacttttttt ttcaatctgg gttacctcaa     300
cctgttttag cacagatatg ggcactagct gacatgaata atgatggaag aatggatcaa     360
gtggagtttt ccatagctat gaaacttatc aaactgaagc tacaaggata tcagctaccc     420
tctgcacttc cccctgtcat gaaacagcaa ccagttgcta tttctagcgc accagcattt     480
ggtatgggag gtatcgccag catgccaccg cttacagctg ttgctccagt gccaatggga     540
tccattccag ttgttggaat gtctccaacc ctagtatctt ctgttcccac agcagctgtg     600
cccccccctgg ctaacggggc tcccctgtt atacaacctc tgcctgcatt tgctcatcct     660
gcagccacat tgccaaagag ttcttccttt agtagatctg gtccagggtc acaactaaac     720
```

```
actaaattac aaaaggcaca gtcatttgat gtggccagtg tcccaccagt ggcagagtgg    780
gctgttcctc agtcatcaag actgaaatac aggcaattat tcaatagtca tgacaaaact    840
atgagtggac acttaacagg tccccaagca agaactattc ttatgcagtc aagtttacca    900
caggctcagc tggcttcaat atggaatctt tctgacattg atcaagatgg aaaacttaca    960
gcagaggaat ttatcctggc aatgcacctc attgatgtag ctatgtctgg ccaaccactg   1020
ccacctgtcc tgcctccaga atacattcca ccttctttta gaagagttcg atctggcagt   1080
ggtatatctg tcataagctc aacatctgta gatcagaggc taccagagga accagtttta   1140
gaagatgaac aacaacaatt agaaaagaaa ttacctgtaa cgtttgaaga taagaagcgg   1200
gagaactttg aacgtggcaa cctggaactg agaaacgaa ggcaagctct cctggaacag   1260
cagcgcaagg agcaggagcg cctggcccag ctggagcggg cggagcagga gaggaaggag   1320
cgtgagcgcc aggagcaaga gcgcaaaaga caactggaac tggagaagca actggaaaag   1380
cagcgggagc tagaacggca gagagaggag gagaggagga agaaattga gaggcgagag   1440
gctgcaaaac gggaacttga aaggcaacga caacttgagt gggaacggaa tcgaaggcaa   1500
gaactactaa atcaaagaaa caagaacaa gaggacatag ttgtactgaa agcaaagaaa   1560
aagactttgg aatttgaatt agaagctcta atgataaaa agcatcaact agaagggaaa   1620
cttcaagata tcagatgtcg attgaccacc caaaggcaag aaattgagag cacaaacaaa   1680
tctagagagt tgagaattgc cgaaatcacc catctacagc aacaattaca ggaatctcag   1740
caaatgcttg gaagacttat tccagaaaaa cagatactca atgaccaatt aaaacaagtt   1800
cagcagaaca gtttgcacag agattcactt gttacactta aaagagcctt agaagcaaaa   1860
gaactagctc ggcagcacct acgagaccaa ctggatgaag tggagaaaga actagatca   1920
aaactacagg agattgatat tttcaataat cagctgaagg aactaagaga aatacacaat   1980
aagcaacaac tccagaagca aaagtccatg gaggctgaac gactgaaaca gaaagaacaa   2040
gaacgaaaga tcatagaatt agaaaaaaaa aaaaaaaaa                          2079

<210> SEQ ID NO 72
<211> LENGTH: 648
<212> TYPE: PRT
<213> ORGANISM: Homo sapiens

<400> SEQUENCE: 72

Met Ala Gln Phe Pro Thr Pro Phe Gly Gly Ser Leu Asp Ile Trp Ala
  1               5                  10                  15

Ile Thr Val Glu Glu Arg Ala Lys His Asp Gln Gln Phe His Ser Leu
                 20                  25                  30

Lys Pro Ile Ser Gly Phe Ile Thr Gly Asp Gln Ala Arg Asn Phe Phe
             35                  40                  45

Phe Gln Ser Gly Leu Pro Gln Pro Val Leu Ala Gln Ile Trp Ala Leu
         50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
            100                 105                 110

Pro Ala Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
```

-continued

```
            130                 135                 140
Thr Leu Val Ser Ser Val Pro Thr Ala Ala Val Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Phe Ser Arg Ser Gly Pro Gly Ser
                180                 185                 190

Gln Leu Asn Thr Lys Leu Gln Lys Ala Gln Ser Phe Asp Val Ala Ser
                195                 200                 205

Val Pro Pro Val Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
                260                 265                 270

Lys Leu Thr Ala Glu Glu Phe Ile Leu Ala Met His Leu Ile Asp Val
    275                 280                 285

Ala Met Ser Gly Gln Pro Leu Pro Pro Val Leu Pro Pro Glu Tyr Ile
    290                 295                 300

Pro Pro Ser Phe Arg Arg Val Arg Ser Gly Ser Gly Ile Ser Val Ile
305                 310                 315                 320

Ser Ser Thr Ser Val Asp Gln Arg Leu Pro Glu Glu Pro Val Leu Glu
                325                 330                 335

Asp Glu Gln Gln Gln Leu Glu Lys Lys Leu Pro Val Thr Phe Glu Asp
                340                 345                 350

Lys Lys Arg Glu Asn Phe Glu Arg Gly Asn Leu Glu Leu Glu Lys Arg
                355                 360                 365

Arg Gln Ala Leu Leu Glu Gln Arg Lys Glu Gln Glu Arg Leu Ala
    370                 375                 380

Gln Leu Glu Arg Ala Glu Gln Glu Arg Lys Glu Arg Glu Arg Gln Glu
385                 390                 395                 400

Gln Glu Arg Lys Arg Gln Leu Glu Leu Glu Lys Gln Leu Glu Lys Gln
                405                 410                 415

Arg Glu Leu Glu Arg Gln Arg Glu Glu Arg Arg Lys Glu Ile Glu
                420                 425                 430

Arg Arg Glu Ala Ala Lys Arg Glu Leu Glu Arg Gln Arg Gln Leu Glu
                435                 440                 445

Trp Glu Arg Asn Arg Arg Gln Glu Leu Leu Asn Gln Arg Asn Lys Glu
    450                 455                 460

Gln Glu Asp Ile Val Val Leu Lys Ala Lys Lys Lys Thr Leu Glu Phe
465                 470                 475                 480

Glu Leu Glu Ala Leu Asn Asp Lys His Gln Leu Glu Gly Lys Leu
                485                 490                 495

Gln Asp Ile Arg Cys Arg Leu Thr Thr Gln Arg Gln Glu Ile Glu Ser
                500                 505                 510

Thr Asn Lys Ser Arg Glu Leu Arg Ile Ala Glu Ile Thr His Leu Gln
    515                 520                 525

Gln Gln Leu Gln Glu Ser Gln Met Leu Gly Arg Leu Ile Pro Glu
    530                 535                 540

Lys Gln Ile Leu Asn Asp Gln Leu Lys Gln Val Gln Gln Asn Ser Leu
545                 550                 555                 560
```

```
His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
            580                 585                 590

Thr Arg Ser Lys Leu Gln Glu Ile Asp Ile Phe Asn Asn Gln Leu Lys
        595                 600                 605

Glu Leu Arg Glu Ile His Asn Lys Gln Leu Gln Lys Gln Lys Ser
    610                 615                 620

Met Glu Ala Glu Arg Leu Lys Gln Lys Glu Gln Glu Arg Lys Ile Ile
625                 630                 635                 640

Glu Leu Glu Lys Lys Lys Lys Lys
                645

<210> SEQ ID NO 73
<211> LENGTH: 33
<212> TYPE: PRT
<213> ORGANISM: Homo sapiens
<220> FEATURE:
<223> OTHER INFORMATION: From Seq ID 73 to ID 75, there are 3 pretein
      sequences translated from Seq ID No. 71. Together,
      they form the whole protein sequence.

<400> SEQUENCE: 73

Arg Gly Trp Cys Ala Gly Leu Arg Leu Leu Arg Pro Ser Gln Arg Arg
  1               5                  10                  15

Val Ser Gly Thr Asp Leu Ser Leu Gly Arg Gln Arg Gly Pro Ala Arg
             20                  25                  30

Arg

<210> SEQ ID NO 74
<211> LENGTH: 3
<212> TYPE: PRT
<213> ORGANISM: Homo sapiens

<400> SEQUENCE: 74

Gly Val Asp
  1

<210> SEQ ID NO 75
<211> LENGTH: 655
<212> TYPE: PRT
<213> ORGANISM: Homo sapiens

<400> SEQUENCE: 75

Gln Gly Lys Ser Asn Arg Thr Met Ala Gln Phe Pro Thr Pro Phe Gly
  1               5                  10                  15

Gly Ser Leu Asp Ile Trp Ala Ile Thr Val Glu Glu Arg Ala Lys His
             20                  25                  30

Asp Gln Gln Phe His Ser Leu Lys Pro Ile Ser Gly Phe Ile Thr Gly
         35                  40                  45

Asp Gln Ala Arg Asn Phe Phe Phe Gln Ser Gly Leu Pro Gln Pro Val
     50                  55                  60

Leu Ala Gln Ile Trp Ala Leu Ala Asp Met Asn Asn Asp Gly Arg Met
 65                  70                  75                  80

Asp Gln Val Glu Phe Ser Ile Ala Met Lys Leu Ile Lys Leu Lys Leu
                 85                  90                  95

Gln Gly Tyr Gln Leu Pro Ser Ala Leu Pro Pro Val Met Lys Gln Gln
            100                 105                 110
```

-continued

```
Pro Val Ala Ile Ser Ser Ala Pro Ala Phe Gly Met Gly Gly Ile Ala
            115                 120                 125
Ser Met Pro Pro Leu Thr Ala Val Ala Pro Val Pro Met Gly Ser Ile
        130                 135                 140
Pro Val Val Gly Met Ser Pro Thr Leu Val Ser Ser Val Pro Thr Ala
145                 150                 155                 160
Ala Val Pro Pro Leu Ala Asn Gly Ala Pro Pro Val Ile Gln Pro Leu
                165                 170                 175
Pro Ala Phe Ala His Pro Ala Ala Thr Leu Pro Lys Ser Ser Ser Phe
            180                 185                 190
Ser Arg Ser Gly Pro Gly Ser Gln Leu Asn Thr Lys Leu Gln Lys Ala
        195                 200                 205
Gln Ser Phe Asp Val Ala Ser Val Pro Pro Val Ala Glu Trp Ala Val
210                 215                 220
Pro Gln Ser Ser Arg Leu Lys Tyr Arg Gln Leu Phe Asn Ser His Asp
225                 230                 235                 240
Lys Thr Met Ser Gly His Leu Thr Gly Pro Gln Ala Arg Thr Ile Leu
                245                 250                 255
Met Gln Ser Ser Leu Pro Gln Ala Gln Leu Ala Ser Ile Trp Asn Leu
            260                 265                 270
Ser Asp Ile Asp Gln Asp Gly Lys Leu Thr Ala Glu Glu Phe Ile Leu
        275                 280                 285
Ala Met His Leu Ile Asp Val Ala Met Ser Gly Gln Pro Leu Pro Pro
290                 295                 300
Val Leu Pro Pro Glu Tyr Ile Pro Pro Ser Phe Arg Arg Val Arg Ser
305                 310                 315                 320
Gly Ser Gly Ile Ser Val Ile Ser Ser Thr Ser Val Asp Gln Arg Leu
                325                 330                 335
Pro Glu Glu Pro Val Leu Glu Asp Glu Gln Gln Gln Leu Glu Lys Lys
            340                 345                 350
Leu Pro Val Thr Phe Glu Asp Lys Lys Arg Glu Asn Phe Glu Arg Gly
        355                 360                 365
Asn Leu Glu Leu Glu Lys Arg Arg Gln Ala Leu Leu Glu Gln Gln Arg
370                 375                 380
Lys Glu Gln Glu Arg Leu Ala Gln Leu Glu Arg Ala Glu Gln Glu Arg
385                 390                 395                 400
Lys Glu Arg Glu Arg Gln Glu Glu Arg Lys Arg Gln Leu Glu Leu
                405                 410                 415
Glu Lys Gln Leu Glu Lys Gln Arg Glu Leu Glu Arg Gln Arg Glu Glu
            420                 425                 430
Glu Arg Arg Lys Glu Ile Glu Arg Arg Glu Ala Ala Lys Arg Glu Leu
        435                 440                 445
Glu Arg Gln Arg Gln Leu Glu Trp Glu Arg Asn Arg Arg Gln Glu Leu
450                 455                 460
Leu Asn Gln Arg Asn Lys Glu Gln Glu Asp Ile Val Val Leu Lys Ala
465                 470                 475                 480
Lys Lys Lys Thr Leu Glu Phe Glu Leu Glu Ala Leu Asn Asp Lys Lys
                485                 490                 495
His Gln Leu Glu Gly Lys Leu Gln Asp Ile Arg Cys Arg Leu Thr Thr
            500                 505                 510
Gln Arg Gln Glu Ile Glu Ser Thr Asn Lys Ser Arg Glu Leu Arg Ile
        515                 520                 525
Ala Glu Ile Thr His Leu Gln Gln Gln Leu Gln Glu Ser Gln Gln Met
```

```
                530               535                540
Leu Gly Arg Leu Ile Pro Glu Lys Gln Ile Leu Asn Asp Gln Leu Lys
545                 550                 555                 560

Gln Val Gln Gln Asn Ser Leu His Arg Asp Ser Leu Val Thr Leu Lys
                565                 570                 575

Arg Ala Leu Glu Ala Lys Glu Leu Ala Arg Gln His Leu Arg Asp Gln
                580                 585                 590

Leu Asp Glu Val Glu Lys Glu Thr Arg Ser Lys Leu Gln Glu Ile Asp
            595                 600                 605

Ile Phe Asn Asn Gln Leu Lys Glu Leu Arg Glu Ile His Asn Lys Gln
610                 615                 620

Gln Leu Gln Lys Gln Lys Ser Met Glu Ala Glu Arg Leu Lys Gln Lys
625                 630                 635                 640

Glu Gln Glu Arg Lys Ile Ile Glu Leu Glu Lys Lys Lys Lys
                645                 650                 655

<210> SEQ ID NO 76
<211> LENGTH: 3231
<212> TYPE: DNA
<213> ORGANISM: Homo sapiens

<400> SEQUENCE: 76
gaccacccaa aggcaagaaa ttgagagcac aaacaaatct agagagttga gaattgccga      60
aatcacccat ctacagcaac aattacagga atctcagcaa atgcttggaa gacttattcc    120
agaaaaacag atactcaatg accaattaaa acaagttcag cagaacagtt tgcacagaga    180
ttcacttgtt acacttaaaa gagccttaga agcaaaagaa ctagctcggc agcacctacg    240
agaccaactg gatgaagtgg agaaagaaac tagatcaaaa ctacaggaga ttgatatttt    300
caataatcag ctgaaggaac taagagaaat acacaataag caacaactcc agaagcaaaa    360
gtccatggag gctgaacgac tgaaacagaa agaacaagac gaaagatcaa agaattaga     420 aaaacaaaaa gaagaagccc aaagacgagc tcaggaaagg gacaagcagt ggctggagca    480
tgtgcagcag gaggacgagc atcagagacc aagaaaactc cacgaagagg aaaaactgaa    540
aagggaggag agtgtcaaaa gaaggatgg cgaggaaaaa ggcaaacagg aagcacaaga    600
caagctgggt cggcttttcc atcaacacca agaaccagct aagccagctg tccaggcacc    660
ctggtccact gcagaaaaag gtccacttac catttctgca caggaaaatg taaaagtggt    720
gtattaccgg gcactgtacc cctttgaatc cagaagccat gatgaaatca ctatccagcc    780
aggagacata gtcatggtgg atgaaagcca aactggagaa cccggctggc ttggaggaga    840
attaaaagga aagacagggt ggttccctgc aaactatgca gagaaaatcc agaaaatga    900 ggttcccgct ccagtgaaac cagtgactga ttcaacatct gcccctgccc ccaaactggc    960
cttgcgtgag accccgccc ctttggcagt aacctcttca gagccctcca cgaccctaa   1020 taactgggcc gacttcagct ccacgtggcc caccagcacg aatgagaaac agaaacgga   1080 taactgggat gcatgggcag cccagccctc tctcaccgtt ccaagtgccg gccagttaag   1140
gcagaggtcc gcctttactc cagccacggc cactggctcc tccccgtctc ctgtgctagg   1200
ccagggtgaa aaggtggagg ggctacaagc tcaagcccta tatccttgga gagccaaaaa   1260
agacaaccac ttaaatttta acaaaaatga tgtcatcacc gtcctggaac agcaagacat   1320
gtggtggttt ggagaagttc aaggtcagaa gggttggttc cccaagtctt acgtgaaact   1380
catttcaggg cccataagga agtctacaag catggattct ggttcttcag agagtcctgc   1440
```

-continued

```
tagtctaaag cgagtagcct ctccagcagc caagccggtc gtttcgggag aagaaattgc    1500
ccaggttatt gcctcataca ccgccaccgg ccccgagcag ctcactctcg cccctggtca    1560
gctgattttg atccgaaaaa agaacccagg tggatggtgg gaaggagagc tgcaagcacg    1620
tgggaaaaag cgccagatag gctggttccc agctaattat gtaaagcttc taagccctgg    1680
gacgagcaaa atcactccaa cagagccacc taagtcaaca gcattagcgg cagtgtgcca    1740
ggtgattggg atgtacgact acaccgcgca gaatgacgat gagctggcct tcaacaaggg    1800
ccagatcatc aacgtcctca acaaggagga ccctgactgg tggaaaggag aagtcaatgg    1860
acaagtgggg ctcttcccat ccaattatgt gaagctgacc acagacatgg acccaagcca    1920
gcaatgaatc atatgttgtc catccccccc tcaggcttga aagtcctttt gtggctttcc    1980
tagttactca aattgacttt cccccacctt tgcacaggtg ctttcaatag ttttaaaatt    2040 attttttaaat atatattta gcttttttaat aaacaaaata aataaatgac ttctttgcta    2100
ttttggtttt gcaaaaagac ccactatcaa ggaatgctgc atgtgctatt aaaaattgtt    2160
ccaaatgtcc ataaatctga gacttgatgt attttttcat tttgtccagt gttaccaact    2220 aaaattgtgca gtttggggct ttccccccctt accatagaag tgcagaggag ttcagtatct    2280
ctgttttaaa gacgtataga atgagcccaa ttaaagcgaa ggtgtttgtg cttgtttgtg    2340
tgtatcagct gtaccttgtt gagcatgtaa tacatcctgt acataagaaa ttagttctttt    2400 ccatggcaaa gctattacct tgtacgatgc tctaatcata ttgcatttaa ttttattttg    2460
cacagtgacc ttgtagccac atgagaaagc actctgtgtt tttgttcggt ctcagattta    2520
tctggttgag ttggtgtttt gtttgggggtt tttaattttg cgtgtttgca tagcataaaa    2580
tcagtagaca acaccactga ggtcgttacg atcaacgata tccacagtct cttttttagtc    2640 tctgttacat gaagttttat tccagttact tttcatggaa tgacctatttt tgaacaagta    2700 atttttcttga caagaaagaa tgtatagaag tctccctgca attaatttcc aatgtttaca    2760
ttttttaact agactgtgga atttctacag attaatatga aatggagctc atggtccgtt    2820
tgtgtgttag atatgctgta gctgaagccc tgtttgtctt ttaaacacta gttggaagct    2880
ctcaataaaa atgcctgctg ctcacagcac agaaaatggg gcaggggag cctcaagcac    2940 aatctagctg tcctcctaaa gactctgtaa tgctcactcc cctcgcgttc tcccggcgct    3000
gtcgggaggc tgtgctggtg gtcgtgtaag gtccttctcc tttcacatgg tgcagagagc    3060
gaggacctct cctcctcgtt cagttgcact tcagtatttt cacggatatg aatgtaaaat    3120
atataaatat ataaacctgc ggctttaaca actgtaatac aacctttttga attagttccg    3180 tgtatagata attaaattct tcatacaaaa gttaaaaaaa aaaaaaaaa a              3231
```

<210> SEQ ID NO 77
<211> LENGTH: 641
<212> TYPE: PRT
<213> ORGANISM: Homo sapiens

<400> SEQUENCE: 77

```
Thr Thr Gln Arg Gln Glu Ile Glu Ser Thr Asn Lys Ser Arg Glu Leu
  1               5                  10                  15

Arg Ile Ala Glu Ile Thr His Leu Gln Gln Gln Leu Gln Glu Ser Gln
             20                  25                  30

Gln Met Leu Gly Arg Leu Ile Pro Glu Lys Gln Ile Leu Asn Asp Gln
         35                  40                  45

Leu Lys Gln Val Gln Gln Asn Ser Leu His Arg Asp Ser Leu Val Thr
     50                  55                  60
```

-continued

Leu Lys Arg Ala Leu Glu Ala Lys Glu Leu Ala Arg Gln His Leu Arg
65                  70                  75                  80

Asp Gln Leu Asp Glu Val Lys Glu Thr Arg Ser Lys Leu Gln Glu
            85                  90                  95

Ile Asp Ile Phe Asn Asn Gln Leu Lys Glu Leu Arg Glu Ile His Asn
                100                 105                 110

Lys Gln Gln Leu Gln Lys Gln Lys Ser Met Glu Ala Glu Arg Leu Lys
            115                 120                 125

Gln Lys Glu Gln Glu Arg Lys Ile Ile Glu Leu Glu Lys Gln Lys Glu
        130                 135                 140

Glu Ala Gln Arg Arg Ala Gln Glu Arg Asp Lys Gln Trp Leu Glu His
145                 150                 155                 160

Val Gln Gln Glu Asp Glu His Gln Arg Pro Arg Lys Leu His Glu Glu
                165                 170                 175

Glu Lys Leu Lys Arg Glu Glu Ser Val Lys Lys Asp Gly Glu Glu
            180                 185                 190

Lys Gly Lys Gln Glu Ala Gln Asp Lys Leu Gly Arg Leu Phe His Gln
        195                 200                 205

His Gln Glu Pro Ala Lys Pro Ala Val Gln Ala Pro Trp Ser Thr Ala
210                 215                 220

Glu Lys Gly Pro Leu Thr Ile Ser Ala Gln Glu Asn Val Lys Val Val
225                 230                 235                 240

Tyr Tyr Arg Ala Leu Tyr Pro Phe Glu Ser Arg Ser His Asp Glu Ile
                245                 250                 255

Thr Ile Gln Pro Gly Asp Ile Val Met Val Asp Glu Ser Gln Thr Gly
            260                 265                 270

Glu Pro Gly Trp Leu Gly Gly Glu Leu Lys Gly Lys Thr Gly Trp Phe
        275                 280                 285

Pro Ala Asn Tyr Ala Glu Lys Ile Pro Glu Asn Glu Val Pro Ala Pro
            290                 295                 300

Val Lys Pro Val Thr Asp Ser Thr Ser Ala Pro Ala Pro Lys Leu Ala
305                 310                 315                 320

Leu Arg Glu Thr Pro Ala Pro Leu Ala Val Thr Ser Ser Glu Pro Ser
                325                 330                 335

Thr Thr Pro Asn Asn Trp Ala Asp Phe Ser Ser Thr Trp Pro Thr Ser
            340                 345                 350

Thr Asn Glu Lys Pro Glu Thr Asp Asn Trp Asp Ala Trp Ala Ala Gln
        355                 360                 365

Pro Ser Leu Thr Val Pro Ser Ala Gly Gln Leu Arg Gln Arg Ser Ala
370                 375                 380

Phe Thr Pro Ala Thr Ala Thr Gly Ser Ser Pro Ser Pro Val Leu Gly
385                 390                 395                 400

Gln Gly Glu Lys Val Glu Gly Leu Gln Ala Gln Ala Leu Tyr Pro Trp
                405                 410                 415

Arg Ala Lys Lys Asp Asn His Leu Asn Phe Asn Lys Asn Asp Val Ile
            420                 425                 430

Thr Val Leu Glu Gln Gln Asp Met Trp Trp Phe Gly Glu Val Gln Gly
        435                 440                 445

Gln Lys Gly Trp Phe Pro Lys Ser Tyr Val Lys Leu Ile Ser Gly Pro
        450                 455                 460

Ile Arg Lys Ser Thr Ser Met Asp Ser Gly Ser Ser Glu Ser Pro Ala
465                 470                 475                 480

```
Ser Leu Lys Arg Val Ala Ser Pro Ala Ala Lys Pro Val Val Ser Gly
            485                 490                 495

Glu Glu Ile Ala Gln Val Ile Ala Ser Tyr Thr Ala Thr Gly Pro Glu
        500                 505                 510

Gln Leu Thr Leu Ala Pro Gly Gln Leu Ile Leu Ile Arg Lys Lys Asn
        515                 520                 525

Pro Gly Gly Trp Trp Glu Gly Glu Leu Gln Ala Arg Gly Lys Lys Arg
530                 535                 540

Gln Ile Gly Trp Phe Pro Ala Asn Tyr Val Lys Leu Leu Ser Pro Gly
545                 550                 555                 560

Thr Ser Lys Ile Thr Pro Thr Glu Pro Pro Lys Ser Thr Ala Leu Ala
                565                 570                 575

Ala Val Cys Gln Val Ile Gly Met Tyr Asp Tyr Thr Ala Gln Asn Asp
            580                 585                 590

Asp Glu Leu Ala Phe Asn Lys Gly Gln Ile Ile Asn Val Leu Asn Lys
        595                 600                 605

Glu Asp Pro Asp Trp Trp Lys Gly Glu Val Asn Gly Gln Val Gly Leu
    610                 615                 620

Phe Pro Ser Asn Tyr Val Lys Leu Thr Thr Asp Met Asp Pro Ser Gln
625                 630                 635                 640

Gln

<210> SEQ ID NO 78
<211> LENGTH: 641
<212> TYPE: PRT
<213> ORGANISM: Homo sapiens

<400> SEQUENCE: 78

Thr Thr Gln Arg Gln Glu Ile Glu Ser Thr Asn Lys Ser Arg Glu Leu
  1               5                  10                  15

Arg Ile Ala Glu Ile Thr His Leu Gln Gln Gln Leu Gln Glu Ser Gln
             20                  25                  30

Gln Met Leu Gly Arg Leu Ile Pro Glu Lys Gln Ile Leu Asn Asp Gln
         35                  40                  45

Leu Lys Gln Val Gln Gln Asn Ser Leu His Arg Asp Ser Leu Val Thr
     50                  55                  60

Leu Lys Arg Ala Leu Glu Ala Lys Glu Leu Ala Arg Gln His Leu Arg
 65                  70                  75                  80

Asp Gln Leu Asp Glu Val Glu Lys Glu Thr Arg Ser Lys Leu Gln Glu
                 85                  90                  95

Ile Asp Ile Phe Asn Asn Gln Leu Lys Glu Leu Arg Glu Ile His Asn
            100                 105                 110

Lys Gln Gln Leu Gln Lys Gln Ser Met Glu Ala Glu Arg Leu Lys
        115                 120                 125

Gln Lys Glu Gln Glu Arg Lys Ile Ile Glu Leu Glu Lys Gln Lys Glu
    130                 135                 140

Glu Ala Gln Arg Arg Ala Gln Glu Arg Asp Lys Gln Trp Leu Glu His
145                 150                 155                 160

Val Gln Gln Glu Asp Glu His Gln Arg Pro Arg Lys Leu His Glu Glu
                165                 170                 175

Glu Lys Leu Lys Arg Glu Glu Ser Val Lys Lys Asp Gly Glu Glu
            180                 185                 190

Lys Gly Lys Gln Glu Ala Gln Asp Lys Leu Gly Arg Leu Phe His Gln
        195                 200                 205
```

-continued

```
His Gln Glu Pro Ala Lys Pro Ala Val Gln Ala Pro Trp Ser Thr Ala
    210                 215                 220
Glu Lys Gly Pro Leu Thr Ile Ser Ala Gln Glu Asn Val Lys Val Val
225                 230                 235                 240
Tyr Tyr Arg Ala Leu Tyr Pro Phe Glu Ser Arg Ser His Asp Glu Ile
                245                 250                 255
Thr Ile Gln Pro Gly Asp Ile Val Met Val Asp Glu Ser Gln Thr Gly
            260                 265                 270
Glu Pro Gly Trp Leu Gly Gly Glu Leu Lys Gly Lys Thr Gly Trp Phe
        275                 280                 285
Pro Ala Asn Tyr Ala Glu Lys Ile Pro Glu Asn Glu Val Pro Ala Pro
    290                 295                 300
Val Lys Pro Val Thr Asp Ser Thr Ser Ala Pro Ala Pro Lys Leu Ala
305                 310                 315                 320
Leu Arg Glu Thr Pro Ala Pro Leu Ala Val Thr Ser Ser Glu Pro Ser
                325                 330                 335
Thr Thr Pro Asn Asn Trp Ala Asp Phe Ser Ser Thr Trp Pro Thr Ser
            340                 345                 350
Thr Asn Glu Lys Pro Glu Thr Asp Asn Trp Asp Ala Trp Ala Ala Gln
        355                 360                 365
Pro Ser Leu Thr Val Pro Ser Ala Gly Gln Leu Arg Gln Arg Ser Ala
    370                 375                 380
Phe Thr Pro Ala Thr Ala Thr Gly Ser Ser Pro Ser Pro Val Leu Gly
385                 390                 395                 400
Gln Gly Glu Lys Val Glu Gly Leu Gln Ala Gln Ala Leu Tyr Pro Trp
                405                 410                 415
Arg Ala Lys Lys Asp Asn His Leu Asn Phe Asn Lys Asn Asp Val Ile
            420                 425                 430
Thr Val Leu Glu Gln Gln Asp Met Trp Trp Phe Gly Glu Val Gln Gly
        435                 440                 445
Gln Lys Gly Trp Phe Pro Lys Ser Tyr Val Lys Leu Ile Ser Gly Pro
    450                 455                 460
Ile Arg Lys Ser Thr Ser Met Asp Ser Gly Ser Ser Glu Ser Pro Ala
465                 470                 475                 480
Ser Leu Lys Arg Val Ala Ser Pro Ala Ala Lys Pro Val Val Ser Gly
                485                 490                 495
Glu Glu Ile Ala Gln Val Ile Ala Ser Tyr Thr Ala Thr Gly Pro Glu
            500                 505                 510
Gln Leu Thr Leu Ala Pro Gly Gln Leu Ile Leu Ile Arg Lys Lys Asn
        515                 520                 525
Pro Gly Gly Trp Trp Glu Gly Glu Leu Gln Ala Arg Gly Lys Lys Arg
    530                 535                 540
Gln Ile Gly Trp Phe Pro Ala Asn Tyr Val Lys Leu Leu Ser Pro Gly
545                 550                 555                 560
Thr Ser Lys Ile Thr Pro Thr Glu Pro Pro Lys Ser Thr Ala Leu Ala
                565                 570                 575
Ala Val Cys Gln Val Ile Gly Met Tyr Asp Tyr Thr Ala Gln Asn Asp
            580                 585                 590
Asp Glu Leu Ala Phe Asn Lys Gly Gln Ile Ile Asn Val Leu Asn Lys
        595                 600                 605
Glu Asp Pro Asp Trp Trp Lys Gly Glu Val Asn Gly Gln Val Gly Leu
    610                 615                 620
Phe Pro Ser Asn Tyr Val Lys Leu Thr Thr Asp Met Asp Pro Ser Gln
```

Gln
625 630 635 640

<210> SEQ ID NO 79
<211> LENGTH: 10
<212> TYPE: PRT
<213> ORGANISM: Homo sapiens

<400> SEQUENCE: 79

Ile Ile Cys Cys Pro Ser Pro Pro Gln Ala
1               5                   10

<210> SEQ ID NO 80
<211> LENGTH: 11
<212> TYPE: PRT
<213> ORGANISM: Homo sapiens

<400> SEQUENCE: 80

Lys Ser Phe Cys Gly Phe Pro Ser Tyr Ser Asn
1               5                   10

<210> SEQ ID NO 81
<211> LENGTH: 30
<212> TYPE: PRT
<213> ORGANISM: Homo sapiens

<400> SEQUENCE: 81

Leu Ser Pro Thr Phe Ala Gln Val Leu Ser Ile Val Leu Lys Leu Phe
1               5                   10                  15

Leu Asn Ile Tyr Phe Ser Phe Leu Ile Asn Lys Ile Asn Lys
            20                  25                  30

<210> SEQ ID NO 82
<211> LENGTH: 20
<212> TYPE: PRT
<213> ORGANISM: Homo sapiens

<400> SEQUENCE: 82

Leu Leu Cys Tyr Phe Gly Phe Ala Lys Arg Pro Thr Ile Lys Glu Cys
1               5                   10                  15

Cys Met Cys Tyr
            20

<210> SEQ ID NO 83
<211> LENGTH: 34
<212> TYPE: PRT
<213> ORGANISM: Homo sapiens

<400> SEQUENCE: 83

Lys Leu Phe Gln Met Ser Ile Asn Leu Arg Leu Asp Val Phe Phe His
1               5                   10                  15

Phe Val Gln Cys Tyr Gln Leu Asn Cys Ala Val Trp Gly Phe Ser Pro
            20                  25                  30

Leu Pro

<210> SEQ ID NO 84
<211> LENGTH: 13
<212> TYPE: PRT
<213> ORGANISM: Homo sapiens

<400> SEQUENCE: 84

Lys Cys Arg Gly Val Gln Tyr Leu Cys Phe Lys Asp Val

<210> SEQ ID NO 85
<211> LENGTH: 4
<212> TYPE: PRT
<213> ORGANISM: Homo sapiens

<400> SEQUENCE: 85

Asn Glu Pro Asn
 1

<210> SEQ ID NO 86
<211> LENGTH: 15
<212> TYPE: PRT
<213> ORGANISM: Homo sapiens

<400> SEQUENCE: 86

Ser Glu Gly Val Cys Ala Cys Leu Cys Val Ser Ala Val Pro Cys
 1               5                  10                  15

<210> SEQ ID NO 87
<211> LENGTH: 7
<212> TYPE: PRT
<213> ORGANISM: Homo sapiens

<400> SEQUENCE: 87

Ala Cys Asn Thr Ser Cys Thr
 1               5

<210> SEQ ID NO 88
<211> LENGTH: 29
<212> TYPE: PRT
<213> ORGANISM: Homo sapiens

<400> SEQUENCE: 88

Glu Ile Ser Ser Phe His Gly Lys Ala Ile Thr Leu Tyr Asp Ala Leu
 1               5                  10                  15

Ile Ile Leu His Leu Ile Leu Phe Cys Thr Val Thr Leu
            20                  25

<210> SEQ ID NO 89
<211> LENGTH: 33
<212> TYPE: PRT
<213> ORGANISM: Homo sapiens

<400> SEQUENCE: 89

Pro His Glu Lys Ala Leu Cys Val Phe Val Arg Ser Gln Ile Tyr Leu
 1               5                  10                  15

Val Glu Leu Val Phe Cys Leu Gly Phe Leu Ile Leu Arg Val Cys Ile
            20                  25                  30

Ala

<210> SEQ ID NO 90
<211> LENGTH: 2
<212> TYPE: PRT
<213> ORGANISM: Homo sapiens

<400> SEQUENCE: 90

Asn Gln
 1

<210> SEQ ID NO 91
<211> LENGTH: 16

```
<212> TYPE: PRT
<213> ORGANISM: Homo sapiens

<400> SEQUENCE: 91

Thr Thr Pro Leu Arg Ser Leu Arg Ser Thr Ile Ser Thr Val Ser Phe
  1               5                  10                  15

<210> SEQ ID NO 92
<211> LENGTH: 14
<212> TYPE: PRT
<213> ORGANISM: Homo sapiens

<400> SEQUENCE: 92

Ser Leu Leu His Glu Val Leu Phe Gln Leu Leu Phe Met Glu
  1               5                  10

<210> SEQ ID NO 93
<211> LENGTH: 5
<212> TYPE: PRT
<213> ORGANISM: Homo sapiens

<400> SEQUENCE: 93

Pro Ile Leu Asn Lys
  1               5

<210> SEQ ID NO 94
<211> LENGTH: 2
<212> TYPE: PRT
<213> ORGANISM: Homo sapiens

<400> SEQUENCE: 94

Phe Ser
  1

<210> SEQ ID NO 95
<211> LENGTH: 29
<212> TYPE: PRT
<213> ORGANISM: Homo sapiens

<400> SEQUENCE: 95

Gln Glu Arg Met Tyr Arg Ser Leu Pro Ala Ile Asn Phe Gln Cys Leu
  1               5                  10                  15

His Phe Leu Thr Arg Leu Trp Asn Phe Tyr Arg Leu Ile
                 20                  25

<210> SEQ ID NO 96
<211> LENGTH: 9
<212> TYPE: PRT
<213> ORGANISM: Homo sapiens

<400> SEQUENCE: 96

Asn Gly Ala His Gly Pro Phe Val Cys
  1               5

<210> SEQ ID NO 97
<211> LENGTH: 4
<212> TYPE: PRT
<213> ORGANISM: Homo sapiens

<400> SEQUENCE: 97

Ile Cys Cys Ser
  1

<210> SEQ ID NO 98
```

```
<211> LENGTH: 33
<212> TYPE: PRT
<213> ORGANISM: Homo sapiens

<400> SEQUENCE: 98
```

Ser Pro Val Cys Leu Leu Asn Thr Ser Trp Lys Leu Ser Ile Lys Met
 1               5                  10                  15

Pro Ala Ala His Ser Thr Glu Asn Gly Ala Gly Ala Ser Ser Thr
             20                  25                  30

Ile

```
<210> SEQ ID NO 99
<211> LENGTH: 3
<212> TYPE: PRT
<213> ORGANISM: Homo sapiens

<400> SEQUENCE: 99
```

Leu Ser Ser
 1

```
<210> SEQ ID NO 100
<211> LENGTH: 62
<212> TYPE: PRT
<213> ORGANISM: Homo sapiens

<400> SEQUENCE: 100
```

Arg Leu Cys Asn Ala His Ser Pro Arg Val Leu Pro Ala Leu Ser Gly
 1               5                  10                  15

Gly Cys Ala Gly Gly Arg Val Arg Ser Phe Ser Phe His Met Val Gln
             20                  25                  30

Arg Ala Arg Thr Ser Pro Pro Arg Ser Val Ala Leu Gln Tyr Phe His
         35                  40                  45

Gly Tyr Glu Cys Lys Ile Tyr Lys Tyr Ile Asn Leu Arg Leu
     50                  55                  60

```
<210> SEQ ID NO 101
<211> LENGTH: 2
<212> TYPE: PRT
<213> ORGANISM: Homo sapiens

<400> SEQUENCE: 101
```

Gln Leu
 1

```
<210> SEQ ID NO 102
<211> LENGTH: 5
<212> TYPE: PRT
<213> ORGANISM: Homo sapiens

<400> SEQUENCE: 102
```

Tyr Asn Leu Leu Asn
 1               5

```
<210> SEQ ID NO 103
<211> LENGTH: 3
<212> TYPE: PRT
<213> ORGANISM: Homo sapiens

<400> SEQUENCE: 103
```

Phe Arg Val
 1

```
<210> SEQ ID NO 104
<211> LENGTH: 14
<212> TYPE: PRT
<213> ORGANISM: Homo sapiens
<220> FEATURE:
<223> OTHER INFORMATION: From Seq ID 78 to ID 104, there are 27 pretein
      sequences translated from Seq ID No. 76. Together,
      they form the whole protein sequence.

<400> SEQUENCE: 104

Ile Ile Lys Phe Phe Ile Gln Lys Leu Lys Lys Lys Lys Lys
 1               5                  10

<210> SEQ ID NO 105
<211> LENGTH: 1721
<212> TYPE: PRT
<213> ORGANISM: Homo sapiens

<400> SEQUENCE: 105

Met Ala Gln Phe Pro Thr Pro Phe Gly Gly Ser Leu Asp Ile Trp Ala
 1               5                  10                  15

Ile Thr Val Glu Glu Arg Ala Lys His Asp Gln Gln Phe His Ser Leu
             20                  25                  30

Lys Pro Ile Ser Gly Phe Ile Thr Gly Asp Gln Ala Arg Asn Phe Phe
         35                  40                  45

Phe Gln Ser Gly Leu Pro Gln Pro Val Leu Ala Gln Ile Trp Ala Leu
     50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
            100                 105                 110

Pro Pro Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Val Pro Pro Val Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
        275                 280                 285

Ala Met Ser Gly Gln Pro Leu Pro Pro Val Leu Pro Pro Glu Tyr Ile
    290                 295                 300
```

```
Pro Pro Ser Phe Arg Arg Val Arg Ser Gly Gly Ile Ser Val Ile
305                 310                 315                 320

Ser Ser Thr Ser Val Asp Gln Arg Leu Pro Glu Glu Pro Val Leu Glu
                325                 330                 335

Asp Glu Gln Gln Gln Leu Glu Lys Lys Leu Pro Val Thr Phe Glu Asp
            340                 345                 350

Lys Lys Arg Glu Asn Phe Glu Arg Gly Asn Leu Glu Leu Glu Lys Arg
                355                 360                 365

Arg Gln Ala Leu Leu Glu Gln Arg Lys Glu Gln Glu Arg Leu Ala
    370                 375                 380

Gln Leu Glu Arg Ala Glu Gln Arg Lys Glu Arg Glu Arg Gln Glu
385                 390                 395                 400

Gln Glu Arg Lys Arg Gln Leu Glu Leu Glu Lys Gln Leu Glu Lys Gln
                405                 410                 415

Arg Glu Leu Glu Arg Gln Arg Glu Glu Glu Arg Arg Lys Glu Ile Glu
                420                 425                 430

Arg Arg Glu Ala Ala Lys Arg Glu Leu Glu Arg Gln Arg Gln Leu Glu
            435                 440                 445

Trp Glu Arg Asn Arg Arg Gln Glu Leu Leu Asn Gln Arg Asn Lys Glu
    450                 455                 460

Gln Glu Asp Ile Val Val Leu Lys Ala Lys Lys Lys Thr Leu Glu Phe
465                 470                 475                 480

Glu Leu Glu Ala Leu Asn Asp Lys Lys His Gln Leu Glu Gly Lys Leu
                485                 490                 495

Gln Asp Ile Arg Cys Arg Leu Thr Thr Gln Arg Gln Glu Ile Glu Ser
            500                 505                 510

Thr Asn Lys Ser Arg Glu Leu Arg Ile Ala Glu Ile Thr His Leu Gln
            515                 520                 525

Gln Gln Leu Gln Glu Ser Gln Gln Met Leu Gly Arg Leu Ile Pro Glu
            530                 535                 540

Lys Gln Ile Leu Asn Asp Gln Leu Lys Gln Val Gln Gln Asn Ser Leu
545                 550                 555                 560

His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
            580                 585                 590

Thr Arg Ser Lys Leu Gln Glu Ile Asp Ile Phe Asn Asn Gln Leu Lys
    595                 600                 605

Glu Leu Arg Glu Ile His Asn Lys Gln Gln Leu Gln Lys Gln Lys Ser
    610                 615                 620

Met Glu Ala Glu Arg Leu Lys Gln Lys Glu Gln Glu Arg Lys Ile Ile
625                 630                 635                 640

Glu Leu Glu Lys Gln Lys Glu Glu Ala Gln Arg Arg Ala Gln Glu Arg
                645                 650                 655

Asp Lys Gln Trp Leu Glu His Val Gln Gln Glu Asp Glu His Gln Arg
            660                 665                 670

Pro Arg Lys Leu His Glu Glu Lys Leu Lys Arg Glu Glu Ser Val
    675                 680                 685

Lys Lys Lys Asp Gly Glu Glu Lys Gly Lys Gln Glu Ala Gln Asp Lys
            690                 695                 700

Leu Gly Arg Leu Phe His Gln His Gln Glu Pro Ala Lys Pro Ala Val
705                 710                 715                 720

Gln Ala Pro Trp Ser Thr Ala Glu Lys Gly Pro Leu Thr Ile Ser Ala
```

-continued

```
                725                 730                 735
Gln Glu Asn Val Lys Val Val Tyr Tyr Arg Ala Leu Tyr Pro Phe Glu
            740                 745                 750

Ser Arg Ser His Asp Glu Ile Thr Ile Gln Pro Gly Asp Ile Val Met
            755                 760                 765

Val Lys Gly Glu Trp Val Asp Glu Ser Gln Thr Gly Glu Pro Gly Trp
770                 775                 780

Leu Gly Gly Glu Leu Lys Gly Lys Thr Gly Trp Phe Pro Ala Asn Tyr
785                 790                 795                 800

Ala Glu Lys Ile Pro Glu Asn Gly Val Pro Ala Pro Val Lys Pro Val
                805                 810                 815

Thr Asp Ser Thr Ser Ala Pro Ala Pro Lys Leu Ala Leu Arg Glu Thr
            820                 825                 830

Pro Ala Pro Leu Ala Val Thr Ser Ser Glu Pro Ser Thr Thr Pro Asn
            835                 840                 845

Asn Trp Ala Asp Phe Ser Ser Thr Trp Pro Thr Ser Thr Asn Glu Lys
            850                 855                 860

Pro Glu Thr Asp Asn Trp Asp Ala Trp Ala Ala Gln Pro Ser Leu Thr
865                 870                 875                 880

Val Pro Ser Ala Gly Gln Leu Arg Gln Arg Ser Ala Phe Thr Pro Ala
                885                 890                 895

Thr Ala Thr Gly Ser Ser Pro Ser Pro Val Leu Gly Gln Gly Glu Lys
            900                 905                 910

Val Glu Gly Leu Gln Ala Gln Ala Leu Tyr Pro Trp Arg Ala Lys Lys
            915                 920                 925

Asp Asn His Leu Asn Phe Asn Lys Asn Asp Val Ile Thr Val Leu Glu
            930                 935                 940

Gln Gln Asp Met Trp Trp Phe Gly Glu Val Gln Gly Gln Lys Gly Trp
945                 950                 955                 960

Phe Pro Lys Ser Tyr Val Lys Leu Ile Ser Gly Pro Ile Arg Lys Ser
                965                 970                 975

Thr Ser Met Asp Ser Gly Ser Ser Glu Ser Pro Ala Ser Leu Lys Arg
            980                 985                 990

Val Ala Ser Pro Ala Ala Lys Pro Val Val Ser Gly Glu Glu Phe Ile
            995                 1000                1005

Ala Met Tyr Thr Tyr Glu Ser Ser Glu Gln Gly Asp Leu Thr Phe Gln
            1010                1015                1020

Gln Gly Asp Val Ile Leu Val Thr Lys Lys Asp Gly Asp Trp Trp Thr
1025                1030                1035                1040

Gly Thr Val Gly Asp Lys Ala Gly Val Phe Pro Ser Asn Tyr Val Arg
            1045                1050                1055

Leu Lys Asp Ser Glu Gly Ser Gly Thr Ala Gly Lys Thr Gly Ser Leu
            1060                1065                1070

Gly Lys Lys Pro Glu Ile Ala Gln Val Ile Ala Ser Tyr Thr Ala Thr
            1075                1080                1085

Gly Pro Glu Gln Leu Thr Leu Ala Pro Gly Gln Leu Ile Leu Ile Arg
            1090                1095                1100

Lys Lys Asn Pro Gly Gly Trp Trp Glu Gly Glu Leu Gln Ala Arg Gly
1105                1110                1115                1120

Lys Lys Arg Gln Ile Gly Trp Phe Pro Ala Asn Tyr Val Lys Leu Leu
            1125                1130                1135

Asn Pro Gly Thr Ser Lys Ile Thr Pro Thr Glu Pro Pro Lys Ser Thr
            1140                1145                1150
```

-continued

Ala Leu Ala Ala Val Cys Gln Val Ile Gly Met Tyr Asp Tyr Thr Ala
          1155                1160                1165

Gln Asn Asp Asp Glu Leu Ala Phe Asn Lys Gly Gln Ile Ile Asn Val
    1170                1175                1180

Leu Asn Lys Glu Asp Pro Asp Trp Trp Lys Gly Glu Val Asn Gly Gln
1185                1190                1195                1200

Val Gly Leu Phe Pro Ser Asn Tyr Val Lys Leu Thr Thr Asp Met Asp
            1205                1210                1215

Pro Ser Gln Gln Trp Cys Ser Asp Leu His Leu Leu Asp Met Leu Thr
        1220                1225                1230

Pro Thr Glu Arg Lys Arg Gln Gly Tyr Ile His Glu Leu Ile Val Thr
    1235                1240                1245

Glu Glu Asn Tyr Val Asn Asp Leu Gln Leu Val Thr Glu Ile Phe Gln
1250                1255                1260

Lys Pro Leu Met Glu Ser Glu Leu Leu Thr Glu Lys Glu Val Ala Met
1265                1270                1275                1280

Ile Phe Val Asn Trp Lys Glu Leu Ile Met Cys Asn Ile Lys Leu Leu
            1285                1290                1295

Lys Ala Leu Arg Val Arg Lys Lys Met Ser Gly Glu Lys Met Pro Val
        1300                1305                1310

Lys Met Ile Gly Asp Ile Leu Ser Ala Gln Leu Pro His Met Gln Pro
    1315                1320                1325

Tyr Ile Arg Phe Cys Ser Arg Gln Leu Asn Gly Ala Ala Leu Ile Gln
    1330                1335                1340

Gln Lys Thr Asp Glu Ala Pro Asp Phe Lys Glu Phe Val Lys Arg Leu
1345                1350                1355                1360

Glu Met Asp Pro Arg Cys Lys Gly Met Pro Leu Ser Ser Phe Ile Leu
            1365                1370                1375

Lys Pro Met Gln Arg Val Thr Arg Tyr Pro Leu Ile Ile Lys Asn Ile
        1380                1385                1390

Leu Glu Asn Thr Pro Glu Asn His Pro Asp His Ser His Leu Lys His
    1395                1400                1405

Ala Leu Glu Lys Ala Glu Glu Leu Cys Ser Gln Val Asn Glu Gly Val
    1410                1415                1420

Arg Glu Lys Glu Asn Ser Asp Arg Leu Glu Trp Ile Gln Ala His Val
1425                1430                1435                1440

Gln Cys Glu Gly Leu Ser Glu Gln Leu Val Phe Asn Ser Val Thr Asn
            1445                1450                1455

Cys Leu Gly Pro Arg Lys Phe Leu His Ser Gly Lys Leu Tyr Lys Ala
        1460                1465                1470

Lys Asn Asn Lys Glu Leu Tyr Gly Phe Leu Phe Asn Asp Phe Leu Leu
    1475                1480                1485

Leu Thr Gln Ile Thr Lys Pro Leu Gly Ser Ser Gly Thr Asp Lys Val
    1490                1495                1500

Phe Ser Pro Lys Ser Asn Leu Gln Tyr Lys Met Tyr Lys Thr Pro Ile
1505                1510                1515                1520

Phe Leu Asn Glu Val Leu Val Lys Leu Pro Thr Asp Pro Ser Gly Asp
            1525                1530                1535

Glu Pro Ile Phe His Ile Ser His Ile Asp Arg Val Tyr Thr Leu Arg
        1540                1545                1550

Ala Glu Ser Ile Asn Glu Arg Thr Ala Trp Val Gln Lys Ile Lys Ala
    1555                1560                1565

```
Ala Ser Glu Leu Tyr Ile Glu Thr Glu Lys Lys Arg Glu Lys Ala
    1570                1575                1580

Tyr Leu Val Arg Ser Gln Arg Ala Thr Gly Ile Gly Arg Leu Met Val
1585                1590                1595                1600

Asn Val Val Glu Gly Ile Glu Leu Lys Pro Cys Arg Ser His Gly Lys
                1605                1610                1615

Ser Asn Pro Tyr Cys Glu Val Thr Met Gly Ser Gln Cys His Ile Thr
                1620                1625                1630

Lys Thr Ile Gln Asp Thr Leu Asn Pro Lys Trp Asn Ser Asn Cys Gln
        1635                1640                1645

Phe Phe Ile Arg Asp Leu Glu Gln Glu Val Leu Cys Ile Thr Val Phe
1650                1655                1660

Glu Arg Asp Gln Phe Ser Pro Asp Phe Leu Gly Arg Thr Glu Ile
1665                1670                1675                1680

Arg Val Ala Asp Ile Lys Lys Asp Gln Gly Ser Lys Gly Pro Val Thr
                1685                1690                1695

Lys Cys Leu Leu Leu His Glu Val Pro Thr Gly Glu Ile Val Val Arg
                1700                1705                1710

Leu Asp Leu Gln Leu Phe Asp Glu Pro
        1715                1720

<210> SEQ ID NO 106
<211> LENGTH: 1220
<212> TYPE: PRT
<213> ORGANISM: Homo sapiens

<400> SEQUENCE: 106

Met Ala Gln Phe Pro Thr Pro Phe Gly Gly Ser Leu Asp Ile Trp Ala
  1               5                  10                  15

Ile Thr Val Glu Glu Arg Ala Lys His Asp Gln Gln Phe His Ser Leu
             20                  25                  30

Lys Pro Ile Ser Gly Phe Ile Thr Gly Asp Gln Ala Arg Asn Phe Phe
         35                  40                  45

Phe Gln Ser Gly Leu Pro Gln Pro Val Leu Ala Gln Ile Trp Ala Leu
     50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Ala Leu Pro Pro Val Met Lys Gln Gln Pro Val Ala Ile Ser Ser Ala
            100                 105                 110

Pro Pro Phe Gly Met Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Thr Leu Val Ser Ser Val Pro Thr Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Leu Pro Lys Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Val Pro Pro Val Ala Glu Trp Ala Val Pro Gln Ser Ser Arg Leu Lys
    210                 215                 220
```

-continued

```
Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
            245                 250                 255

Ala Gln Leu Ala Ser Ile Trp Asn Leu Ser Asp Ile Asp Gln Asp Gly
                260                 265                 270

Lys Leu Thr Ala Glu Glu Phe Ile Leu Ala Met His Leu Ile Asp Val
            275                 280                 285

Ala Met Ser Gly Gln Pro Leu Pro Pro Val Leu Pro Pro Glu Tyr Ile
290                 295                 300

Pro Pro Ser Phe Arg Arg Val Arg Ser Gly Ser Gly Ile Ser Val Ile
305                 310                 315                 320

Ser Ser Thr Ser Val Asp Gln Arg Leu Pro Glu Glu Pro Val Leu Glu
                325                 330                 335

Asp Glu Gln Gln Gln Leu Glu Lys Lys Leu Pro Val Thr Phe Glu Asp
                340                 345                 350

Lys Lys Arg Glu Asn Phe Glu Arg Gly Asn Leu Glu Leu Glu Lys Arg
            355                 360                 365

Arg Gln Ala Leu Leu Glu Gln Arg Lys Glu Gln Glu Arg Leu Ala
            370                 375                 380

Gln Leu Glu Arg Ala Glu Gln Glu Arg Lys Glu Arg Glu Arg Gln Glu
385                 390                 395                 400

Gln Glu Arg Lys Arg Gln Leu Glu Leu Glu Lys Gln Leu Glu Lys Gln
                405                 410                 415

Arg Glu Leu Glu Arg Gln Arg Glu Glu Glu Arg Arg Lys Glu Ile Glu
            420                 425                 430

Arg Arg Glu Ala Ala Lys Arg Glu Leu Glu Arg Gln Arg Gln Leu Glu
            435                 440                 445

Trp Glu Arg Asn Arg Arg Gln Glu Leu Leu Asn Gln Arg Asn Lys Glu
450                 455                 460

Gln Glu Asp Ile Val Val Leu Lys Ala Lys Lys Lys Thr Leu Glu Phe
465                 470                 475                 480

Glu Leu Glu Ala Leu Asn Asp Lys Lys His Gln Leu Glu Gly Lys Leu
                485                 490                 495

Gln Asp Ile Arg Cys Arg Leu Thr Thr Gln Arg Gln Glu Ile Glu Ser
            500                 505                 510

Thr Asn Lys Ser Arg Glu Leu Arg Ile Ala Glu Ile Thr His Leu Gln
            515                 520                 525

Gln Gln Leu Gln Glu Ser Gln Gln Met Leu Gly Arg Leu Ile Pro Glu
530                 535                 540

Lys Gln Ile Leu Asn Asp Gln Leu Lys Gln Val Gln Asn Ser Leu
545                 550                 555                 560

His Arg Asp Ser Leu Val Thr Leu Lys Arg Ala Leu Glu Ala Lys Glu
                565                 570                 575

Leu Ala Arg Gln His Leu Arg Asp Gln Leu Asp Glu Val Glu Lys Glu
            580                 585                 590

Thr Arg Ser Lys Leu Gln Glu Ile Asp Ile Phe Asn Asn Gln Leu Lys
            595                 600                 605

Glu Leu Arg Glu Ile His Asn Lys Gln Gln Leu Gln Lys Gln Lys Ser
            610                 615                 620

Met Glu Ala Glu Arg Leu Lys Gln Lys Glu Gln Glu Arg Lys Ile Ile
625                 630                 635                 640
```

-continued

```
Glu Leu Glu Lys Gln Lys Glu Ala Gln Arg Arg Ala Gln Glu Arg
                645                 650                 655

Asp Lys Gln Trp Leu Glu His Val Gln Glu Asp Glu His Gln Arg
            660                 665                 670

Pro Arg Lys Leu His Glu Glu Lys Leu Lys Arg Glu Glu Ser Val
        675                 680                 685

Lys Lys Lys Asp Gly Glu Glu Lys Gly Lys Gln Glu Ala Gln Asp Lys
690                 695                 700

Leu Gly Arg Leu Phe His Gln His Gln Glu Pro Ala Lys Pro Ala Val
705                 710                 715                 720

Gln Ala Pro Trp Ser Thr Ala Glu Lys Gly Pro Leu Thr Ile Ser Ala
                725                 730                 735

Gln Glu Asn Val Lys Val Val Tyr Tyr Arg Ala Leu Tyr Pro Phe Glu
            740                 745                 750

Ser Arg Ser His Asp Glu Ile Thr Ile Gln Pro Gly Asp Ile Val Met
        755                 760                 765

Val Lys Gly Glu Trp Val Asp Glu Ser Gln Thr Gly Glu Pro Gly Trp
    770                 775                 780

Leu Gly Gly Glu Leu Lys Gly Lys Thr Gly Trp Phe Pro Ala Asn Tyr
785                 790                 795                 800

Ala Glu Lys Ile Pro Glu Asn Glu Val Pro Ala Pro Val Lys Pro Val
                805                 810                 815

Thr Asp Ser Thr Ser Ala Pro Ala Pro Lys Leu Ala Leu Arg Glu Thr
            820                 825                 830

Pro Ala Pro Leu Ala Val Thr Ser Glu Pro Ser Thr Thr Pro Asn
        835                 840                 845

Asn Trp Ala Asp Phe Ser Ser Thr Trp Pro Thr Ser Thr Asn Glu Lys
    850                 855                 860

Pro Glu Thr Asp Asn Trp Asp Ala Trp Ala Ala Gln Pro Ser Leu Thr
865                 870                 875                 880

Val Pro Ser Ala Gly Gln Leu Arg Gln Arg Ser Ala Phe Thr Pro Ala
                885                 890                 895

Thr Ala Thr Gly Ser Ser Pro Ser Pro Val Leu Gly Gln Gly Glu Lys
            900                 905                 910

Val Glu Gly Leu Gln Ala Gln Ala Leu Tyr Pro Trp Arg Ala Lys Lys
        915                 920                 925

Asp Asn His Leu Asn Phe Asn Lys Asn Asp Val Ile Thr Val Leu Glu
930                 935                 940

Gln Gln Asp Met Trp Trp Phe Gly Glu Val Gln Gly Gln Lys Gly Trp
945                 950                 955                 960

Phe Pro Lys Ser Tyr Val Lys Leu Ile Ser Gly Pro Ile Arg Lys Ser
                965                 970                 975

Thr Ser Met Asp Ser Gly Ser Ser Glu Ser Pro Ala Ser Leu Lys Arg
            980                 985                 990

Val Ala Ser Pro Ala Ala Lys Pro Val Val Ser Gly Glu Glu Phe Ile
        995                 1000                1005

Ala Met Tyr Thr Tyr Glu Ser Ser Glu Gln Gly Asp Leu Thr Phe Gln
    1010                1015                1020

Gln Gly Asp Val Ile Leu Val Thr Lys Lys Asp Gly Asp Trp Trp Thr
1025                1030                1035                1040

Gly Thr Val Gly Asp Lys Ala Gly Val Phe Pro Ser Asn Tyr Val Arg
                1045                1050                1055

Leu Lys Asp Ser Glu Gly Ser Gly Thr Ala Gly Lys Thr Gly Ser Leu
```

-continued

```
                    1060                1065                1070
Gly Lys Lys Pro Glu Ile Ala Gln Val Ile Ala Ser Tyr Thr Ala Thr
        1075                1080                1085

Gly Pro Glu Gln Leu Thr Leu Ala Pro Gly Gln Leu Ile Leu Ile Arg
    1090                1095                1100

Lys Lys Asn Pro Gly Gly Trp Trp Glu Gly Glu Leu Gln Ala Arg Gly
1105                1110                1115                1120

Lys Lys Arg Gln Ile Gly Trp Phe Pro Ala Asn Tyr Val Lys Leu Leu
            1125                1130                1135

Asn Pro Gly Thr Ser Lys Ile Thr Pro Thr Glu Pro Pro Lys Ser Thr
        1140                1145                1150

Ala Leu Ala Ala Val Cys Gln Val Ile Gly Met Tyr Asp Tyr Thr Ala
    1155                1160                1165

Gln Asn Asp Asp Glu Leu Ala Phe Asn Lys Gly Gln Ile Ile Asn Val
1170                1175                1180

Leu Asn Lys Glu Asp Pro Asp Trp Trp Lys Gly Glu Val Asn Gly Gln
1185                1190                1195                1200

Val Gly Leu Phe Pro Ser Asn Tyr Val Lys Leu Thr Thr Asp Met Asp
            1205                1210                1215

Pro Ser Gln Gln
        1220

<210> SEQ ID NO 107
<211> LENGTH: 1270
<212> TYPE: PRT
<213> ORGANISM: Xenopus laevis

<400> SEQUENCE: 107

Met Ala Gln Phe Gly Thr Pro Phe Gly Gly Asn Leu Asp Ile Trp Ala
1               5                   10                  15

Ile Thr Val Glu Glu Arg Ala Lys His Asp Gln Gln Phe His Gly Leu
            20                  25                  30

Lys Pro Thr Ala Gly Tyr Ile Thr Gly Asp Gln Ala Arg Asn Phe Phe
        35                  40                  45

Leu Gln Ser Gly Leu Pro Gln Pro Val Leu Ala Gln Ile Trp Ala Leu
    50                  55                  60

Ala Asp Met Asn Asn Asp Gly Arg Met Asp Gln Leu Glu Phe Ser Ile
65                  70                  75                  80

Ala Met Lys Leu Ile Lys Leu Lys Leu Gln Gly Tyr Pro Leu Pro Ser
            85                  90                  95

Ile Leu Pro Ser Asn Met Leu Lys Gln Pro Val Ala Met Pro Ala Ala
        100                 105                 110

Ala Val Ala Gly Phe Gly Met Ser Gly Ile Val Gly Ile Pro Pro Leu
    115                 120                 125

Ala Ala Val Ala Pro Val Pro Met Pro Ser Ile Pro Val Val Gly Met
130                 135                 140

Ser Pro Pro Leu Val Ser Ser Val Pro Thr Val Pro Pro Leu Ser Asn
145                 150                 155                 160

Gly Ala Pro Ala Val Ile Gln Ser His Pro Ala Phe Ala His Ser Ala
            165                 170                 175

Thr Leu Pro Lys Ser Ser Phe Gly Arg Ser Val Ala Gly Ser Gln
        180                 185                 190

Ile Asn Thr Lys Leu Gln Lys Ala Gln Ser Phe Asp Val Pro Ala Pro
    195                 200                 205
```

-continued

```
Pro Leu Val Val Glu Trp Ala Val Pro Ser Ser Ser Arg Leu Lys Tyr
    210                 215                 220

Arg Gln Leu Phe Asn Ser Gln Asp Lys Thr Met Ser Gly Asn Leu Thr
225                 230                 235                 240

Gly Pro Gln Ala Arg Thr Ile Leu Met Gln Ser Ser Leu Pro Gln Ser
                245                 250                 255

Gln Leu Ala Thr Ile Trp Asn Leu Ser Asp Ile Asp Gln Asp Gly Lys
            260                 265                 270

Leu Thr Ala Glu Glu Phe Ile Leu Ala Met His Leu Ile Asp Val Ala
        275                 280                 285

Met Ser Gly Gln Pro Leu Pro Pro Ile Leu Pro Pro Glu Tyr Ile Pro
    290                 295                 300

Pro Ser Phe Arg Arg Val Arg Ser Gly Ser Gly Leu Ser Ile Met Ser
305                 310                 315                 320

Ser Val Ser Val Asp Gln Arg Leu Pro Glu Glu Pro Glu Glu Glu Glu
                325                 330                 335

Pro Gln Asn Ala Asp Lys Lys Leu Pro Val Thr Phe Glu Asp Lys Lys
                340                 345                 350

Arg Glu Asn Phe Glu Arg Gly Asn Leu Glu Leu Glu Lys Arg Arg Gln
            355                 360                 365

Ala Leu Leu Glu Gln Gln Arg Lys Glu Gln Arg Leu Ala Gln Leu
        370                 375                 380

Glu Arg Ala Glu Gln Glu Arg Lys Glu Arg Glu Arg Gln Asp Gln Glu
385                 390                 395                 400

Arg Lys Arg Gln Gln Asp Leu Glu Lys Gln Leu Glu Lys Gln Arg Glu
                405                 410                 415

Leu Glu Arg Gln Arg Glu Glu Arg Arg Lys Glu Ile Glu Arg Arg
            420                 425                 430

Glu Ala Ala Lys Arg Glu Leu Glu Arg Gln Arg Gln Leu Glu Trp Glu
        435                 440                 445

Arg Asn Arg Arg Gln Glu Leu Leu Asn Gln Arg Asn Arg Glu Gln Glu
    450                 455                 460

Asp Ile Val Val Leu Lys Ala Lys Lys Lys Thr Leu Glu Phe Glu Leu
465                 470                 475                 480

Glu Ala Leu Asn Asp Lys Lys His Gln Leu Glu Gly Lys Leu Gln Asp
                485                 490                 495

Ile Arg Cys Arg Leu Thr Thr Gln Arg His Glu Ile Glu Ser Thr Asn
            500                 505                 510

Lys Ser Arg Glu Leu Arg Ile Ala Glu Ile Thr His Leu Gln Gln Gln
        515                 520                 525

Leu Gln Glu Ser Gln Gln Leu Leu Gly Lys Met Ile Pro Glu Lys Gln
    530                 535                 540

Ser Leu Ile Asp Gln Leu Lys Gln Val Gln Gln Asn Ser Leu His Arg
545                 550                 555                 560

Asp Ser Leu Leu Thr Leu Lys Arg Ala Leu Glu Thr Lys Glu Ile Gly
                565                 570                 575

Arg Gln Gln Leu Arg Asp Gln Leu Asp Glu Val Glu Lys Glu Thr Arg
            580                 585                 590

Ala Lys Leu Gln Glu Ile Asp Val Phe Asn Asn Gln Leu Lys Glu Leu
        595                 600                 605

Arg Glu Leu Tyr Asn Lys Gln Gln Phe Gln Lys Gln Asp Phe Glu
    610                 615                 620

Thr Glu Lys Ile Lys Gln Lys Glu Leu Glu Arg Lys Thr Ser Glu Leu
```

-continued

```
              625                 630                 635                 640
Asp Lys Leu Lys Glu Glu Asp Lys Arg Arg Met Leu Glu Gln Asp Lys
                    645                 650                 655
Leu Trp Gln Asp Arg Val Lys Gln Glu Glu Arg Tyr Lys Phe Gln
                660                 665                 670
Asp Glu Glu Lys Glu Lys Arg Glu Glu Ser Val Gln Lys Cys Glu Val
                675                 680                 685
Glu Lys Lys Pro Glu Ile Gln Glu Lys Pro Asn Lys Pro Phe His Gln
            690                 695                 700
Pro Pro Glu Pro Gly Lys Leu Gly Gly Gln Ile Pro Trp Met Asn Thr
705                 710                 715                 720
Glu Lys Ala Pro Leu Thr Ile Asn Gln Gly Asp Val Lys Val Tyr
                725                 730                 735
Tyr Arg Ala Leu Tyr Pro Phe Asp Ala Arg Ser His Asp Glu Ile Thr
                740                 745                 750
Ile Glu Pro Gly Asp Ile Ile Met Val Asp Glu Ser Gln Thr Gly Glu
                755                 760                 765
Pro Gly Trp Leu Gly Gly Glu Leu Lys Gly Lys Thr Gly Trp Phe Pro
            770                 775                 780
Ala Asn Tyr Ala Glu Arg Met Pro Glu Ser Glu Phe Pro Ser Thr Thr
785                 790                 795                 800
Lys Pro Ala Ala Glu Thr Thr Ala Lys Pro Thr Val His Val Ala Pro
                805                 810                 815
Ser Pro Val Ala Pro Ala Ala Phe Thr Asn Thr Ser Thr Asn Ser Asn
                820                 825                 830
Asn Trp Ala Asp Phe Ser Ser Thr Trp Pro Thr Asn Asn Thr Asp Lys
            835                 840                 845
Val Glu Ser Asp Asn Trp Asp Thr Trp Ala Ala Gln Pro Ser Leu Thr
        850                 855                 860
Val Pro Ser Ala Gly Gln His Arg Gln Arg Ser Ala Phe Thr Pro Ala
865                 870                 875                 880
Thr Val Thr Gly Ser Ser Pro Ser Pro Val Leu Gly Gln Gly Glu Lys
                885                 890                 895
Val Glu Gly Leu Gln Ala Gln Ala Leu Tyr Pro Trp Arg Ala Lys Lys
            900                 905                 910
Asp Asn His Leu Asn Phe Asn Lys Asn Asp Val Ile Thr Val Leu Glu
        915                 920                 925
Gln Gln Asp Met Trp Trp Phe Gly Glu Val Gln Gly Gln Lys Gly Trp
    930                 935                 940
Phe Pro Lys Ser Tyr Val Lys Leu Ile Ser Gly Pro Leu Arg Lys Ser
945                 950                 955                 960
Thr Ser Ile Asp Ser Thr Ser Ser Glu Ser Pro Ala Ser Leu Lys Arg
                965                 970                 975
Val Ser Ser Pro Ala Phe Lys Pro Ala Ile Gln Gly Glu Glu Tyr Ile
                980                 985                 990
Ser Met Tyr Thr Tyr Glu Ser Asn Glu Gln Gly Asp Leu Thr Phe Gln
                995                1000                1005
Gln Gly Asp Leu Ile Val Val Ile Lys Lys Asp Gly Asp Trp Trp Thr
        1010                1015                1020
Gly Thr Val Gly Glu Lys Thr Gly Val Phe Pro Ser Asn Tyr Val Arg
1025                1030                1035                1040
Pro Lys Asp Ser Glu Ala Ala Gly Ser Gly Gly Lys Thr Gly Ser Leu
                1045                1050                1055
```

-continued

```
Gly Lys Lys Pro Glu Ile Ala Gln Val Ile Ala Ser Tyr Ala Ala Thr
            1060                1065                1070

Ala Pro Glu Gln Leu Thr Leu Ala Pro Gly Gln Leu Ile Leu Ile Arg
        1075                1080                1085

Lys Lys Asn Pro Gly Gly Trp Trp Glu Gly Glu Leu Gln Ala Arg Gly
1090                1095                1100

Lys Lys Arg Gln Ile Gly Trp Phe Pro Ala Asn Tyr Val Lys Leu Leu
1105                1110                1115                1120

Ser Pro Gly Thr Asn Lys Ser Thr Pro Thr Glu Pro Pro Lys Pro Thr
                1125                1130                1135

Ser Leu Pro Pro Thr Cys Gln Val Ile Gly Met Tyr Asp Tyr Ile Ala
            1140                1145                1150

Gln Asn Asp Asp Glu Leu Ala Phe Ser Lys Gly Gln Val Ile Asn Val
        1155                1160                1165

Leu Asn Lys Glu Asp Pro Asp Trp Trp Lys Gly Glu Leu Asn Gly His
    1170                1175                1180

Val Gly Leu Phe Pro Ser Asn Tyr Val Lys Leu Thr Thr Asp Met Asp
1185                1190                1195                1200

Pro Ser Gln Gln Phe Arg Leu Gly Val Lys Pro Ala Gly Gly Ile Pro
                1205                1210                1215

Ala Thr Gly Asp Arg Pro Phe Ile Leu Phe Pro Phe Arg Asp Gly Pro
            1220                1225                1230

Ser Leu Leu Pro Asn Ala Phe Gln Ala Pro Leu Ser Val Val Met
        1235                1240                1245

Ile Lys Phe Arg Cys Phe Thr Ala Pro Arg Phe Cys Pro Asp Met Asn
    1250                1255                1260

Val Lys Tyr Ile Asn Ile
1265                1270

<210> SEQ ID NO 108
<211> LENGTH: 1094
<212> TYPE: PRT
<213> ORGANISM: Drosophila sp.

<400> SEQUENCE: 108

Met Asn Ser Ala Val Asp Ala Trp Ala Val Thr Pro Arg Glu Arg Leu
1               5                   10                  15

Lys Tyr Gln Glu Gln Phe Arg Ala Leu Gln Pro Gln Ala Gly Phe Val
            20                  25                  30

Thr Gly Ala Gln Ala Lys Gly Phe Phe Leu Gln Ser Gln Leu Pro Pro
        35                  40                  45

Leu Ile Leu Gly Gln Ile Trp Ala Leu Ala Asp Thr Asp Ser Asp Gly
    50                  55                  60

Lys Met Asn Ile Asn Glu Phe Ser Ile Ala Cys Lys Leu Ile Asn Leu
65                  70                  75                  80

Lys Leu Arg Gly Met Asp Val Pro Lys Val Leu Pro Pro Ser Leu Leu
                85                  90                  95

Ser Ser Leu Thr Gly Asp Val Pro Ser Met Thr Pro Arg Gly Ser Thr
            100                 105                 110

Ser Ser Leu Ser Pro Leu Asp Pro Leu Lys Gly Ile Val Pro Ala Val
        115                 120                 125

Ala Pro Val Val Pro Val Val Ala Pro Val Ala Val Ala Thr Val
    130                 135                 140

Ile Ser Pro Pro Gly Val Ser Val Pro Ser Gly Pro Thr Pro Pro Thr
```

```
            145                 150                 155                 160
Ser Asn Pro Pro Ser Arg His Thr Ser Ile Ser Glu Arg Ala Pro Ser
                    165                 170                 175
Ile Glu Ser Val Asn Gln Gly Glu Trp Ala Val Gln Ala Ala Gln Lys
                    180                 185                 190
Arg Lys Tyr Thr Gln Val Phe Asn Ala Asn Asp Arg Thr Arg Ser Gly
                    195                 200                 205
Tyr Leu Thr Gly Ser Gln Ala Arg Gly Val Leu Val Gln Ser Lys Leu
                    210                 215                 220
Pro Gln Val Thr Leu Ala Gln Ile Trp Thr Leu Ser Asp Ile Asp Gly
225                 230                 235                 240
Asp Gly Arg Leu Asn Cys Asp Glu Phe Ile Leu Ala Met Phe Leu Cys
                    245                 250                 255
Glu Lys Ala Met Ala Gly Glu Lys Ile Pro Val Thr Leu Pro Gln Glu
                    260                 265                 270
Trp Val Pro Pro Asn Leu Arg Lys Ile Lys Ser Arg Pro Gly Ser Val
                    275                 280                 285
Ser Gly Val Val Ser Arg Pro Gly Ser Gln Pro Ala Ser Arg His Ala
                    290                 295                 300
Ser Val Ser Ser Gln Ser Gly Val Gly Val Val Asp Ala Asp Pro Thr
305                 310                 315                 320
Ala Gly Leu Pro Gly Gln Thr Ser Phe Glu Asp Lys Arg Lys Glu Asn
                    325                 330                 335
Tyr Val Lys Gly Gln Ala Glu Leu Asp Arg Arg Arg Lys Ile Met Glu
                    340                 345                 350
Asp Gln Gln Arg Lys Glu Arg Glu Glu Arg Glu Arg Lys Glu Arg Glu
                    355                 360                 365
Glu Ala Asp Lys Arg Glu Lys Ala Arg Leu Glu Ala Glu Arg Lys Gln
                    370                 375                 380
Gln Glu Glu Leu Glu Arg Gln Leu Gln Arg Gln Arg Glu Ile Glu Met
385                 390                 395                 400
Glu Lys Glu Glu Gln Arg Lys Arg Glu Leu Glu Ala Lys Glu Ala Ala
                    405                 410                 415
Arg Lys Glu Leu Glu Lys Gln Arg Gln Glu Trp Glu Gln Ala Arg
                    420                 425                 430
Ile Ala Glu Met Asn Ala Gln Lys Glu Arg Glu Gln Glu Arg Val Leu
                    435                 440                 445
Lys Gln Lys Ala His Asn Thr Gln Leu Asn Val Glu Leu Ser Thr Leu
                    450                 455                 460
Asn Glu Lys Ile Lys Glu Leu Ser Gln Arg Ile Cys Asp Thr Arg Ala
465                 470                 475                 480
Gly Val Thr Asn Val Lys Thr Val Ile Asp Gly Met Arg Thr Gln Arg
                    485                 490                 495
Asp Thr Ser Met Ser Glu Met Ser Gln Leu Lys Ala Arg Ile Lys Glu
                    500                 505                 510
Gln Asn Ala Lys Leu Leu Gln Leu Thr Gln Glu Arg Ala Lys Trp Glu
                    515                 520                 525
Ala Lys Ser Lys Ala Ser Gly Ala Ala Leu Gly Gly Glu Asn Ala Gln
                    530                 535                 540
Gln Glu Gln Leu Asn Ala Ala Phe Ala His Lys Gln Leu Ile Ile Asn
545                 550                 555                 560
Gln Ile Lys Asp Lys Val Glu Asn Ile Ser Lys Glu Ile Glu Ser Lys
                    565                 570                 575
```

-continued

```
Lys Glu Asp Ile Asn Thr Asn Asp Val Gln Met Ser Glu Leu Lys Ala
            580                 585                 590
Glu Leu Ser Ala Leu Ile Thr Lys Cys Glu Asp Leu Tyr Lys Glu Tyr
        595                 600                 605
Asp Val Gln Arg Thr Ser Val Leu Glu Leu Lys Tyr Asn Arg Lys Asn
    610                 615                 620
Glu Thr Ser Val Ser Ser Ala Trp Asp Thr Gly Ser Ser Ser Ala Trp
625                 630                 635                 640
Glu Glu Thr Gly Thr Thr Val Thr Asp Pro Tyr Ala Val Ala Ser Asn
                645                 650                 655
Asp Ile Ser Ala Leu Ala Ala Pro Val Asp Leu Gly Gly Pro Ala
            660                 665                 670
Pro Glu Gly Phe Val Lys Tyr Gln Ala Val Tyr Glu Phe Asn Ala Arg
        675                 680                 685
Asn Ala Glu Glu Ile Thr Phe Val Pro Gly Asp Ile Ile Leu Val Pro
    690                 695                 700
Leu Glu Gln Asn Ala Glu Pro Gly Trp Leu Ala Gly Glu Ile Asn Gly
705                 710                 715                 720
His Thr Gly Trp Phe Pro Glu Ser Tyr Val Glu Lys Leu Glu Val Gly
                725                 730                 735
Glu Val Ala Pro Val Ala Ala Val Glu Ala Pro Val Asp Ala Gln Val
            740                 745                 750
Ala Asp Thr Tyr Asn Asp Asn Ile Asn Thr Ser Ser Ile Pro Ala Ala
        755                 760                 765
Ser Ala Asp Leu Thr Ala Ala Gly Asp Val Glu Tyr Tyr Ile Ala Ala
    770                 775                 780
Tyr Pro Tyr Glu Ser Ala Glu Glu Gly Asp Leu Ser Phe Ser Ala Gly
785                 790                 795                 800
Glu Met Val Met Val Ile Lys Lys Glu Gly Glu Trp Trp Thr Gly Thr
                805                 810                 815
Ile Gly Ser Arg Thr Gly Met Phe Pro Ser Asn Tyr Val Gln Lys Ala
            820                 825                 830
Asp Val Gly Thr Ala Ser Thr Ala Ala Ala Glu Pro Val Glu Ser Leu
        835                 840                 845
Asp Gln Glu Thr Thr Leu Asn Gly Asn Ala Ala Tyr Thr Ala Ala Pro
    850                 855                 860
Val Glu Ala Gln Glu Gln Val Tyr Gln Pro Leu Pro Val Gln Glu Pro
865                 870                 875                 880
Ser Glu Gln Pro Ile Ser Ser Pro Gly Val Gly Ala Glu Glu Ala His
                885                 890                 895
Glu Asp Leu Asp Thr Glu Val Ser Gln Ile Asn Thr Gln Ser Lys Thr
            900                 905                 910
Gln Ser Ser Glu Pro Ala Glu Ser Tyr Ser Arg Pro Met Ser Arg Thr
        915                 920                 925
Ser Ser Met Thr Pro Gly Met Arg Ala Lys Arg Ser Glu Ile Ala Gln
    930                 935                 940
Val Ile Ala Pro Tyr Glu Ala Thr Ser Thr Glu Gln Leu Ser Leu Thr
945                 950                 955                 960
Arg Gly Gln Leu Ile Met Ile Arg Lys Lys Thr Asp Ser Gly Trp Trp
                965                 970                 975
Glu Gly Glu Leu Gln Ala Lys Gly Arg Arg Gln Ile Gly Trp Phe
            980                 985                 990
```

-continued

```
Pro Ala Thr Tyr Val Lys Val Leu Gln Gly Gly Arg Asn Ser Gly Arg
        995                 1000                1005

Asn Thr Pro Val Ser Gly Ser Arg Ile Glu Met Thr Glu Gln Ile Leu
    1010                1015                1020

Asp Lys Val Ile Ala Leu Tyr Pro Tyr Lys Ala Gln Asn Asp Asp Glu
1025                1030                1035                1040

Leu Ser Phe Asp Lys Asp Asp Ile Ile Ser Val Leu Gly Arg Asp Glu
                1045                1050                1055

Pro Glu Trp Trp Arg Gly Glu Leu Asn Gly Leu Ser Gly Leu Phe Pro
                1060                1065                1070

Ser Asn Tyr Val Gly Pro Phe Val Thr Ser Gly Lys Pro Ala Lys Ala
        1075                1080                1085

Asn Gly Thr Thr Lys Lys
    1090

<210> SEQ ID NO 109
<211> LENGTH: 520
<212> TYPE: PRT
<213> ORGANISM: Homo sapiens

<400> SEQUENCE: 109

Met Glu Ala Glu Arg Leu Lys Gln Lys Glu Gln Glu Arg Lys Ile Ile
  1               5                  10                  15

Glu Leu Glu Lys Gln Lys Glu Ala Gln Arg Arg Ala Gln Glu Arg
             20                  25                  30

Asp Lys Gln Trp Leu Glu His Val Gln Gln Glu Asp Glu His Gln Arg
         35                  40                  45

Pro Arg Lys Leu His Glu Glu Lys Leu Lys Arg Glu Glu Ser Val
     50                  55                  60

Lys Lys Lys Asp Gly Glu Glu Lys Gly Lys Gln Glu Ala Gln Asp Lys
 65                  70                  75                  80

Leu Gly Arg Leu Phe His Gln His Gln Glu Pro Ala Lys Pro Ala Val
                 85                  90                  95

Gln Ala Pro Trp Ser Thr Ala Glu Lys Gly Pro Leu Thr Ile Ser Ala
            100                 105                 110

Gln Glu Asn Val Lys Val Val Tyr Tyr Arg Ala Leu Tyr Pro Phe Glu
        115                 120                 125

Ser Arg Ser His Asp Glu Ile Thr Ile Gln Pro Gly Asp Ile Val Met
    130                 135                 140

Val Asp Glu Ser Gln Thr Gly Glu Pro Gly Trp Leu Gly Gly Glu Leu
145                 150                 155                 160

Lys Gly Lys Thr Gly Trp Phe Pro Ala Asn Tyr Ala Glu Lys Ile Pro
                165                 170                 175

Glu Asn Glu Val Pro Ala Pro Val Lys Pro Val Thr Asp Ser Thr Ser
            180                 185                 190

Ala Pro Ala Pro Lys Leu Ala Leu Arg Glu Thr Pro Ala Pro Leu Ala
        195                 200                 205

Val Thr Ser Ser Glu Pro Ser Thr Thr Pro Asn Asn Trp Ala Asp Phe
    210                 215                 220

Ser Ser Thr Trp Pro Thr Ser Thr Asn Glu Lys Pro Glu Thr Asp Asn
225                 230                 235                 240

Trp Asp Ala Trp Ala Ala Gln Pro Ser Leu Thr Val Pro Ser Ala Gly
                245                 250                 255

Gln Leu Arg Gln Arg Ser Ala Phe Thr Pro Ala Thr Ala Thr Gly Ser
            260                 265                 270
```

-continued

```
Ser Pro Ser Pro Val Leu Gly Gln Gly Glu Lys Val Glu Gly Leu Gln
        275                 280                 285

Ala Gln Ala Leu Tyr Pro Trp Arg Ala Lys Lys Asp Asn His Leu Asn
        290                 295                 300

Phe Asn Lys Asn Asp Val Ile Thr Val Leu Glu Gln Gln Asp Met Trp
305                 310                 315                 320

Trp Phe Gly Glu Val Gln Gly Gln Lys Gly Trp Phe Pro Lys Ser Tyr
                325                 330                 335

Val Lys Leu Ile Ser Gly Pro Ile Arg Lys Ser Thr Ser Met Asp Ser
                340                 345                 350

Gly Ser Ser Glu Ser Pro Ala Ser Leu Lys Arg Val Ala Ser Pro Ala
        355                 360                 365

Ala Lys Pro Val Val Ser Gly Glu Glu Ile Ala Gln Val Ile Ala Ser
        370                 375                 380

Tyr Thr Ala Thr Gly Pro Glu Gln Leu Thr Leu Ala Pro Gly Gln Leu
385                 390                 395                 400

Ile Leu Ile Arg Lys Lys Asn Pro Gly Gly Trp Trp Glu Gly Glu Leu
                405                 410                 415

Gln Ala Arg Gly Lys Lys Arg Gln Ile Gly Trp Phe Pro Ala Asn Tyr
                420                 425                 430

Val Lys Leu Leu Ser Pro Gly Thr Ser Lys Ile Thr Pro Thr Glu Pro
        435                 440                 445

Pro Lys Ser Thr Ala Leu Ala Ala Val Cys Gln Val Ile Gly Met Tyr
        450                 455                 460

Asp Tyr Thr Ala Gln Asn Asp Asp Glu Leu Ala Phe Asn Lys Gly Gln
465                 470                 475                 480

Ile Ile Asn Val Leu Asn Lys Glu Asp Pro Asp Trp Trp Lys Gly Glu
                485                 490                 495

Val Asn Gly Gln Val Gly Leu Phe Pro Ser Asn Tyr Val Lys Leu Thr
        500                 505                 510

Thr Asp Met Asp Pro Ser Gln Gln
        515                 520
```